United States Patent
Elmer et al.

(10) Patent No.: US 10,307,389 B2
(45) Date of Patent: *Jun. 4, 2019

(54) SUCCINATE PRODRUGS FOR USE IN THE TREATMENT OF LACTIC ACIDOSIS OR DRUG-INDUCED SIDE-EFFECTS DUE TO COMPLEX I-RELATED IMPAIRMENT OF MITOCHONDRIAL OXIDATIVE PHOSPHORYLATION

(71) Applicant: NEUROVIVE PHARMACEUTICAL AB, Lund (SE)

(72) Inventors: Eskil Elmer, Lund (SE); Magnus Joakim Hansson, Landskrona (SE); Karl Henrik Johannes Ehinger, Lund (SE); Sarah Piel, Lund (SE); Steven Moss, Blasham (GB)

(73) Assignee: NEUROVIVE PHARMACEUTICAL AB, Lund (SE)

( * ) Notice: Subject to any disclaimer, the term of this patent is extended or adjusted under 35 U.S.C. 154(b) by 0 days.

This patent is subject to a terminal disclaimer.

(21) Appl. No.: 15/128,496

(22) PCT Filed: Apr. 8, 2015

(86) PCT No.: PCT/EP2015/057615
§ 371 (c)(1),
(2) Date: Sep. 23, 2016

(87) PCT Pub. No.: WO2015/155238
PCT Pub. Date: Oct. 15, 2015

(65) Prior Publication Data
US 2017/0100359 A1 Apr. 13, 2017

(30) Foreign Application Priority Data

Apr. 8, 2014 (DK) .................................. 2014 70185
Apr. 8, 2014 (DK) .................................. 2014 70187
Apr. 8, 2014 (DK) .................................. 2014 70190

(51) Int. Cl.
*A61K 31/225* (2006.01)
*A61K 45/06* (2006.01)
*A61K 31/155* (2006.01)

(52) U.S. Cl.
CPC .......... *A61K 31/225* (2013.01); *A61K 31/155* (2013.01); *A61K 45/06* (2013.01)

(58) Field of Classification Search
CPC ..... A61K 31/225; A61K 31/155; A61K 45/06
See application file for complete search history.

(56) References Cited

FOREIGN PATENT DOCUMENTS

| EP | 0583480 | | 2/1994 | |
|----|---------|---|--------|---|
| EP | 1558220 | * | 6/2010 | ............... A61K 9/20 |
| JP | 2014024772 | | 2/2014 | |
| KR | 100791844 | | 1/2008 | |
| WO | 97/47584 | | 12/1997 | |
| WO | 02/28345 | | 4/2002 | |
| WO | 2008/054059 | | 5/2008 | |
| WO | 2008/118948 | | 10/2008 | |
| WO | 2012/011063 | | 1/2012 | |
| WO | 2014/053857 | | 4/2014 | |
| WO | 2015/155230 | | 10/2015 | |
| WO | 2015/155231 | | 10/2015 | |

OTHER PUBLICATIONS

Protti (Critical Care 2013, vol. 17 Suppl 2, p. S1, S167, S168).*
Kubinyi (3D QSAR in Drug Design: Ligand-Protein Interactions and Molecular Similarity, vol. 2-3, Springer, 1998, 800 pages). pp. 243-244 provided.*
Wermuth, The Practice of Medicinal Chemsitry, 2d ed. (2003), 768 pages. Chapters 9-10 provided.*
Ehinger et al. (Nat Commun. 2016; 7: 12317, p. 1-18).*
Globa, O.V., et al., "Succinate Treatment in Children with Lactic Acidosis," European Collaboration: Towards Drug Development and Rational Drug Therapy, Proceedings of the Sixth Congress of the European Association for Clinical Pharmacology and Therapeutics, Istanbul, Jun. 24-28, 2003, Eds. Tulunay and Orme, Springer-Verlag Berlin Heidelberg GmbH, 2003, p. 130.
Klug, E., et al., "AGI-1067 Improves Glycemic Control when Added to Current Regimens in Patients with Type 2 Diabetes" Diabetes (2008) 57(S1):A132 [Abstract].
Kruidering, M., et al., "Cispltain-Induced Nephrotoxicity in Porcine Proximal Tubular Cells: Mitochondruial Dysfunction by Inhibition of Complexes I to IV of the Respiratory Chain," J. Pharmacol. Exper. Therap. (1997) 280:638-649.
Moore, S.A., et al., "Model Reactions for CoA Transferase Involving Thiol Transfer. Anhydride Formation from Thiol Esters and Carboxylic Acids," J. Biol. Chem. (1982) 257:10882-10892.
Nudelman, A., et al., "The Role of Intracellularly Released Formaldehyde and Butyric Acid in the Anticancer Activity of Acyloxyalkyl Esters," J. Med. Chem. (2005) 48:1042-1054.

* cited by examiner

*Primary Examiner* — Robert H Havlin
(74) *Attorney, Agent, or Firm* — Robert C. Netter, Jr.; Dann, Dorfman, Herrell & Skillman

(57) ABSTRACT

The present invention relates to a succinate prodrug for use in the treatment or prevention of lactic acidosis.

4 Claims, 7 Drawing Sheets

Figure 1:
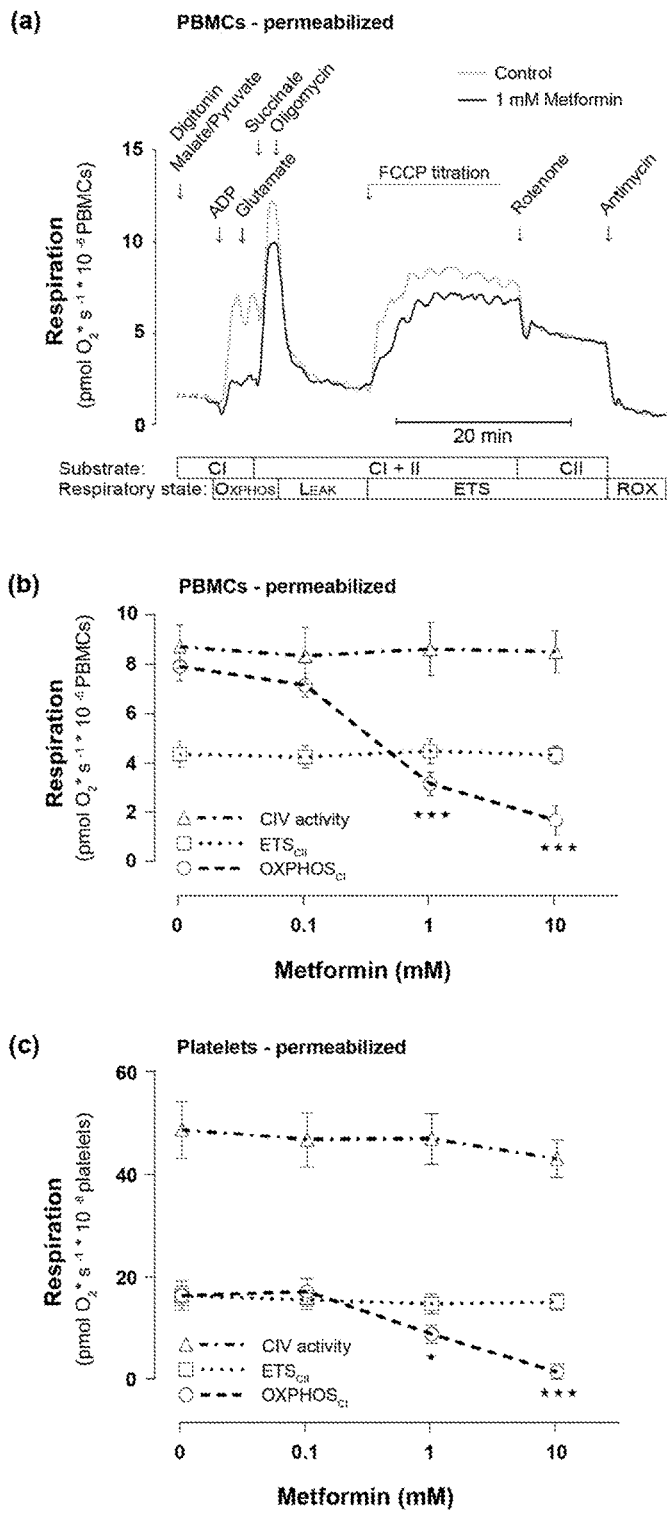

SUCCINATE PRODRUGS FOR USE IN THE TREATMENT OF LACTIC ACIDOSIS OR DRUG-INDUCED SIDE-EFFECTS DUE TO COMPLEX I-RELATED IMPAIRMENT OF MITOCHONDRIAL OXIDATIVE PHOSPHORYLATION

This application is a § 371 application of PCT/EP2015/057615, filed Apr. 8, 2015, which in turn claims priority to DK Application PA 2014 70185, filed Apr. 8, 2014, DK Application PA 2014 70187, filed Apr. 8, 2014, and DK Application PA 2014 70190, filed Apr. 8, 2014. The entire disclosure of each of the foregoing applications is incorporated by reference herein.

FIELD OF THE INVENTION

The present invention relates to the use of succinate prodrugs for the treatment of mitochondria-related disorders, in particular disorders relating to Complex I of the respiratory chain. In particular the invention relates to the use of succinate prodrugs for the treatment of lactic acidosis.

BACKGROUND OF THE INVENTION

Mitochondrial toxicity induced by drugs may be a part of the desired therapeutic effect (e.g. mitochondrial toxicity induced by cancer drugs), but in most case mitochondrial toxicity induced by drugs is an unwanted effect. Mitochondrial toxicity can markedly increase glycolysis to compensate for cellular loss of mitochondrial ATP formation by oxidative phosphorylation. This can result in increased lactate plasma levels, which if excessive results in lactic acidosis, which can be lethal. Type A lactic acidosis is primarily associated with tissue hypoxia, whereas type B aerobic lactic acidosis is associated with drugs, toxin or systemic disorders such as liver diseases, diabetes, cancer and inborn errors of metabolism (e.g. mitochondrial genetic defects).

Many known drug substances negatively influence mitochondrial respiration (e.g. anti-psychotics, local anaesthetics and anti-diabetics) and, accordingly, there is a need to identify or develop means that either can be used to circumvent or alleviate the negative mitochondrial effects induced by the use of such a drug substance.

DESCRIPTION OF THE INVENTION

The present invention provides succinate prodrugs for use in the prevention or treatment of lactic acidosis and of mitochondrial-related drug-induced side effects. In particular the succinate prodrugs are used in the prevention or treatment of a mitochondrial-related drug-induced side effects at or up-stream of Complex I, or expressed otherwise, the invention provides succinate prodrugs for the prevention or treatment of drug-induced direct inhibition of Complex I or of any drug-induced effect that limits the supply of NADH to Complex I (such as, but not limited to, effects on Krebs cycle, glycolysis, beta-oxidation, pyruvate metabolism and even drugs that effects the transport or levels of glucose or other substrates). Side-effects related to a Complex I defect, inhibition or malfunction, and iii) side-effects related to defect, inhibition or malfunction in aerobic metabolism upstream of complex I, defect, malfunction or dysfunction of mitochondria can be recognized by use of the method described in WO 2014 053617.

As mentioned above, increased lactate plasma levels are often observed in patients treated with drugs that may have mitochondrial-related side effects. The present invention is based on experimental results showing that metformin (first-line treatment for type 2 diabetes and which has been associated with lactic acidosis as a rare side-effect) inhibits mitochondrial function of human peripheral blood cells at Complex I in a time- and dose-dependent fashion at concentrations relevant for metformin intoxication. Metformin further causes a significant increase in lactate production by intact platelets over time. The use of succinate prodrugs significantly reduced lactate production in metformin-exposed intact platelets. Exogenously applied succinate, the substrate itself, did not reduce the metformin-induced production of lactate.

In another study, the production of lactate was observed over several hours in rotenone-inhibited platelets (i.e. a condition where the function of complex I is impaired). The use of succinate prodrugs (but not succinate) attenuated the rotenone-induced lactate production of intact human platelets. Respirometric experiments were repeated in human fibroblasts and human heart muscle fibres, and confirmed the findings seen in blood cells.

Accordingly, the invention provides succinate prodrugs for use in the prevention of treatment of lactic acidosis. However, as the results reported herein are based on lactic acidosis related to direct inhibition of Complex I or associated with a defect at or up-stream of Complex I, it is contemplated that the succinate prodrugs are suitable for use in the prevention or treatment of a mitochondrial-related drug-induced side-effects at or up-stream of Complex I. The succinate prodrugs would also counteract drug effects disrupting metabolism upstream of complex I (indirect inhibition of Complex I, which would encompass any drug effect that limits the supply of NADH to Complex I, e.g. effects on Krebs cycle, glycolysis, beta-oxidation, pyruvate metabolism and even drugs that affect the levels of glucose or other substrates).

It is contemplated that the succinate prodrugs also can be used in industrial applications, e.g. in vitro to reduce or inhibit formation of lactate. Examples include the use in cell culture, in organ preservation, etc.

Succinate Prodrugs

It is contemplated that any succinate prodrug can be used in accordance with the present invention, provided it can permeate through the cell membrane or otherwise enter through the cytoplasmic membrane. The term "succinate prodrug" is used synonymous with the term "protected succinate". In the present context, a succinate prodrug is a derivative of succinic acid, which either by hydrolysis, enzymatic degradation or otherwise can release succinate (or succinic acid) in vivo after administration or in vitro after application. The pro-moiety serves the purpose of changing the characteristic of succinate from being non-permeable through the cytoplasmic membrane to being permeable or serves the purpose of making succinate otherwise available to mitochondria. Normally, the pro-moiety of a prodrug is regarded as a therapeutically inert moiety. However, in the present context the pro-moiety may be inert, or it may have some activity as long as it is a desired activity or an activity that does not create any harm to the patient.

Of particular interest are protected succinates according to Formula A:

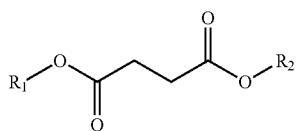

(A)

wherein $R_1$ and $R_2$ are same or different and selected from formula (B)

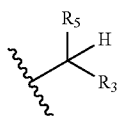

(B)

and wherein the drug-induced mitochondrial side effect is direct or indirect Complex I inhibition and wherein $R_3$ is selected from H, or optionally substituted $C_1$-$C_3$ alkyl such as e.g. methyl, ethyl, propyl or iso-propyl and wherein $R_5$ is —OC(=O)$R_a$, wherein $R_a$ is methyl or formula (C)

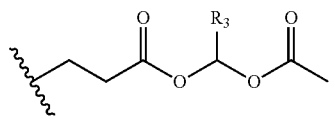

(C)

In a specific aspect, $R_1$ and $R_2$ are same of different and selected from formula (II), wherein $R_3$ is H or methyl and $R_a$ is methyl or formula (C).

The protected succinates are used in the treatment or prevention of drug-induced mitochondrial-related side-effects. Especially, they are used in the treatment or prevention of direct or indirect drug-induced Complex I mitochondrial-related side-effects. In particular, they are used in the treatment or prevention of lactic acidosis, such as lactic acidosis induced by a drug substance.

The invention also relates to a combination of a protected succinate and a drug substance that may induce a mitochondrial-related side-effect, in particular a side-effect that is caused by direct or indirect impairment of Complex I by the drug substance. Such combination can be used as prophylactic prevention of a mitochondrial-related side-effect or, in case the side-effect appears, in alleviating and/or treating the mitochondrial-related side effect.

It is contemplated that succinate prodrugs as described below will be effective in treatment or prevention of drug-induced side-effects, in particular in side-effects related to direct or indirect inhibition of Complex I. Examples of compounds for use according to the present invention are given in the following list of items:

1. A protected succinate of formula (I)

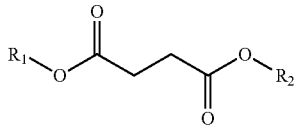

wherein $R_1$ is H, a pharmaceutically acceptable salt, an optionally substituted alkyl group or a group of formula (II) and $R_2$ is independently a group according to formula (II) where formula (II) is

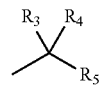

wherein $R_3$ is H, optionally substituted $C_1$-$C_3$ alkyl, or is linked together with $R_5$ by a group of formula COO(CR'R")O to form a ring, where R' and R" are independently H, optionally substituted $C_1$-$C_3$ alkyl, or are linked together to form a ring;
$R_4$ is H;
$R_5$ is OCOR$_a$, OCOOR$_b$, OCONR$_c$R$_d$, SO$_2$R$_e$, OPO(OR$_f$)(OR$_g$), CONR$_c$R$_d$ or is linked to $R_3$ by a group of formula COO(CR'R")O to form a ring, where R' and R" are independently H, optionally substituted $C_1$-$C_3$ alkyl, or are linked together to form a ring; where
$R_a$ is methyl, ethyl, CH(CH$_3$)$_2$ or C(CH$_3$)$_3$ or cycloalkyl;
$R_b$ is methyl, ethyl, CH(CH$_3$)$_2$ or C(CH$_3$)$_3$ or cycloalkyl;
$R_c$ and $R_d$ are independently H, methyl or ethyl or are linked together to form a ring which may contain one or more further heteroatoms;
$R_e$ is optionally substituted alkyl; and
$R_f$ and $R_g$ are independently, H, methyl, ethyl or are linked together to form a ring.

2. A protected succinate according to item 1, wherein $R_1$ is a $C_1$-$C_3$ alkyl group or a group of formula (II) and $R_2$ is independently a group according to formula (II) where formula (II) is

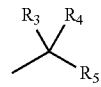

wherein $R_3$ is H, $C_1$-$C_3$ alkyl, or is linked together with $R_5$ by a group of formula COO(CR'R")O to form a ring, where R' and R" are independently optionally substituted $C_1$-$C_3$ alkyl;
$R_4$ is H;
$R_5$ is OCOR$_a$, OCOOR$_b$, or CONR$_c$R$_d$
where
$R_a$ is methyl, ethyl or $^t$Bu;
$R_b$ is methyl, ethyl or $^t$Bu;
$R_c$ and $R_d$ are independently methyl or ethyl.

3. The protected succinate according to items 1-2 wherein $R_3$ is methyl or ethyl.
4. The protected succinate according to items 1-2 wherein $R_3$ is H.
5. The protected succinate according to items 1-2 wherein $R_1$ is methyl.
6. The protected succinate according to items 1-2 where $R_5$ is an optionally substituted methyl or ethyl ester.

7. The protected succinate of items 1-2 represented by formula IV

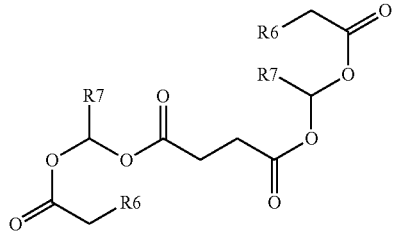

wherein each $R_7$ is independently H, methyl or ethyl and each $R_6$ is independently H or methyl.

8. The protected succinate of items 1-2 wherein $R_c$ and $R_d$ are methyl or ethyl.

9. The protected succinate according to items 1-2, wherein R' and R" are independently methyl or ethyl.

10. The protected succinate according to items 1-2 wherein $R_3$ and $R_5$ are linked together by a group of formula COO(CR'R")O to form a ring of formula (V)

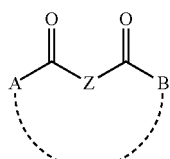

wherein $R_4$ is H and R' and R" are independently H, optionally substituted $C_1$-$C_3$ alkyl, or are linked together to form a ring.

11. The protected succinate of item 11 according to formula (Va)

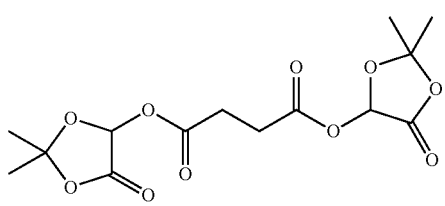

12. A protected succinate of formula (XIII)

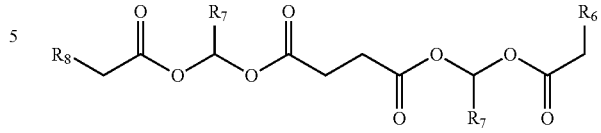

wherein each $R_7$ is independently H, methyl or ethyl and $R_6$ is independently H or methyl and $R_8$ is H, methyl or a moiety according to formula (XIV)

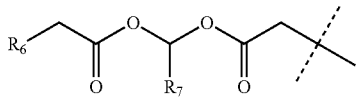

where $R_7$ is independently H, methyl or ethyl and $R_6$ is independently H or methyl.

13. A protected di-succinate of formula (XV)

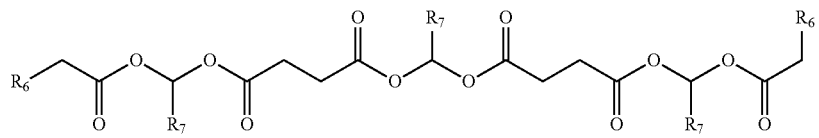

wherein each $R_7$ is independently H, methyl or ethyl and each $R_6$ is independently H or methyl 14. A protected succinate according to any previous items wherein the compound is selected from compound Nos. 3, 5, 8, 10, 13, 14, 16, 17 or 18.

15. A protected succinate according to any previous items wherein the compound is selected from compound Nos. 3, 5, 13, 14, 17 or 18.

16. A protected succinate as defined in any of items 1-15 for use in stimulating mitochondrial energy production.

Another class of succinate analogs is given in the following list A:

1 A. A compound according to the invention is given by Formula (I)

(I)

or a pharmaceutically acceptable salt thereof, wherein the dotted bond between A and B denotes an optional bond so as to form a ring closed structure, and wherein Z is selected from —CH$_2$—CH$_2$— or >CH(CH$_3$),
A is selected from —SR, —OR and NHR, and R is

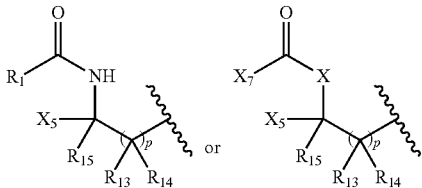

B is selected from —O—R', —NHR'', —SR''' or —OH; and R' is selected from the formula (II) to (IX) below:

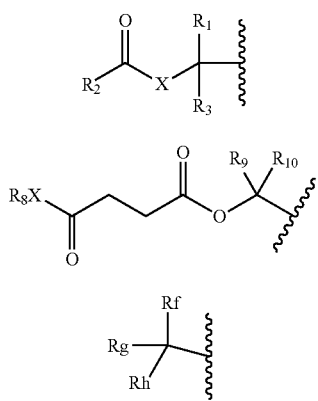

(II)

(V)

(IX)

R', R'' and R''' are independently different or identical and is selected from formula (IV-VIII) below:

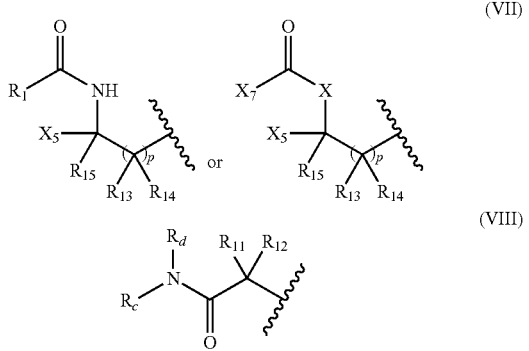

(VII)

(VIII)

R$_1$ and R$_3$ are independently different or identical and are selected from H, Me, Et, propyl, i-propyl, butyl, iso-butyl, t-butyl, O-acyl, O-alkyl, N-acyl, N-alkyl, Xacyl, CH$_2$Xalkyl, CH$_2$X-acyl, F, CH$_2$COOH, CH$_2$CO$_2$alkyl, X is selected from O, NH, NR$_6$, S, R$_2$ is selected from Me, Et, propyl, i-propyl, butyl, iso-butyl, t-butyl, C(O)CH$_3$, C(O)CH$_2$C(O)CH$_3$, C(O)CH$_2$CH(OH)CH$_3$, p is an integer and is 1 or 2

R$_6$ is selected from H, Me, Et, propyl, i-propyl, butyl, iso-butyl, t-butyl, acetyl, acyl, propionyl, benzoyl, or formula (II), or formula (VIII)

X$_5$ is selected from —H, Me, Et, propyl, i-propyl, butyl, iso-butyl, t-butyl, —COOH, —C(=O)XR$_6$, CONR$_1$R$_3$ or is formula

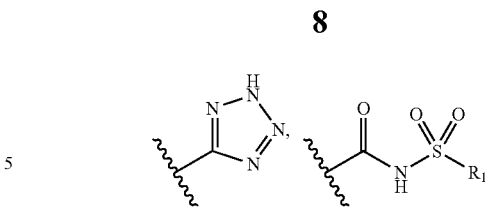

X$_7$ is selected from R$_1$, —NR$_1$R$_3$,

R$_9$ is selected from H, Me, Et or O$_2$CCH$_2$CH$_2$COXR$_8$

R$_{10}$ is selected from Oacyl, NHalkyl, NHacyl, or O$_2$CCH$_2$CH$_2$COX$_6$R$_8$ X$_6$ is selected from O, NR$_8$, NR$_6$R$_8$, wherein R$_6$ and R$_8$ are independently different or identical and are is selected from H, alkyl, Me, Et, propyl, i-propyl, butyl, iso-butyl, t-butyl, acetyl, acyl, propionyl, benzoyl, or formula (II), or formula (VIII), R$_{11}$ and R$_{12}$ are independently different or identical and are selected from H, Me, Et, propyl, i-propyl, butyl, iso-butyl, t-butyl, acetyl, propionyl, benzoyl, —CH$_2$Xalkyl, —CH$_2$Xacyl, where X is O, NR$_6$ or S, R$_c$ and R$_d$ are independently different or identical and are selected from CH$_2$Xalkyl, CH$_2$Xacyl, where X=O, NR$_6$ or S, R$_{13}$, R$_{14}$ and R$_{15}$ are independently different or identical and are selected from H, Me, Et, propyl, i-propyl, butyl, iso-butyl, t-butyl, —COOH, O-acyl, O-alkyl, N-acyl, N-alkyl, Xacyl, CH$_2$Xalkyl;

Substituents on R13 and R14 or R13 and R15 may bridge to form a cyclic system,

R$_f$, R$_g$ and R$_h$ are independently different or identical and are selected from Xacyl, —CH$_2$Xalkyl, —CH$_2$X-acyl and R$_9$, alkyl is selected from Me, Et, propyl, i-propyl, butyl, iso-butyl, t-butyl, acyl is selected from formyl, acetyl, propionyl, isopropionyl, byturyl, tert-butyryl, pentanoyl, benzoyl, acyl and/or alkyl may be optionally substituted, and when the dotted bond between A and B is present, the compound according to formula (I) is

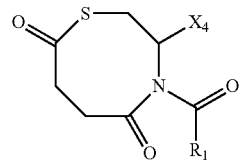

wherein X$_4$ is selected from —COOH, —C(=O)XR$_6$,

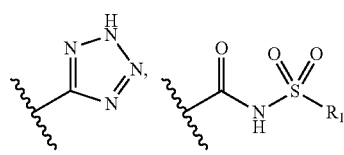

2A. A compound according to item 1A having Formula (IA)

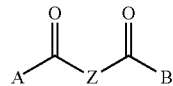
(IA)

or a pharmaceutically acceptable salt thereof, wherein thereof, wherein

Z is —CH$_2$—CH$_2$—,

A is selected from —SR, —OR and NHR, and R is

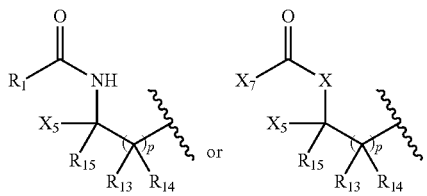

B is selected from —O—R', —NHR", —SR''' or —OH; and

R', R" and R''' are independently different or identical and is selected from one or the formulas below:

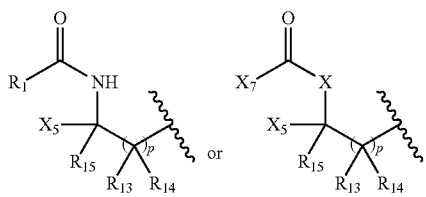
(VII)

R$_1$ and R$_3$ are independently different or identical and are selected from H, Me, Et, propyl, O-Me, O-Et, O-propyl, X is selected from O, NH, S, p is an integer and is 1, R$_6$ is selected from H, Me, Et, X$_5$ is selected from —H, Me, Et, —COOH, —C(=O)XR$_6$, CONR$_1$R$_3$, X$_7$ is selected from R$_1$, —NR$_1$R$_3$, R$_{13}$, R$_{14}$ and R$_{15}$ are independently different or identical and are selected from H, Me, Et, propyl, i-propyl, butyl, iso-butyl, t-butyl, —COOH, O-acyl, O-alkyl, N-acyl, N-alkyl, Xacyl, CH$_2$Xalkyl, wherein alkyl and acyl are as defined herein before.

3A. A compound according to item 1A or 2A having Formula (IA)

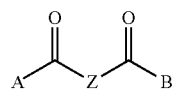
(IA)

or a pharmaceutically acceptable salt thereof, wherein

Z is —CH$_2$—CH$_2$—,

A is selected from —SR, —OR and NHR, and R is

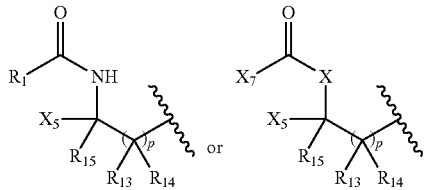

B is selected from —O—R', —NHR", —SR''' or —OH; and

R', R" and R''' are independently different or identical and is selected from one or the formulas below:

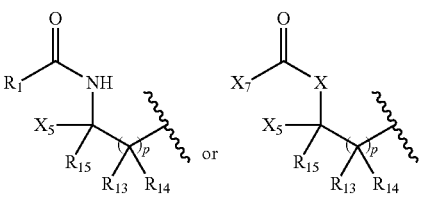
(VII)

R$_1$ and R$_3$ are independently different or identical and are selected from H, Me, Et, propyl, O-Me, O-Et, O-propyl, X is selected from O, NH, S, p is an integer and is 1, R$_6$ is selected from H, Me, Et, X$_5$ is selected from —H, Me, Et, —COOH, —C(=O)OR$_6$, CONR$_1$R$_3$, X$_7$ is selected from R$_1$, —NR$_1$R$_3$, R$_{13}$, R$_{14}$ and R$_{15}$ are independently different or identical and are selected from H, Me, Et, —COOH.

4A. A compound according to any one of the preceding items, wherein Z is —CH$_2$OH$_2$— and A is —SR.

5A. A compound according to any one of the preceding items, wherein Z is —CH$_2$CH$_2$—, A is —SR, and B is OH or SR'''.

6A. A compound according to any one of the preceding items, wherein Z is —CH$_2$CH$_2$—, A is —SR, B is OH or SR''', where R''' is

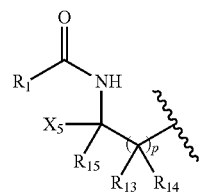

7A. A compound according to any one of the preceding items, wherein Z is —CH$_2$CH$_2$— and A is SR and B is OH.

8A. A compound according to any one of item 1A-6A, wherein Z is

—CH$_2$CH$_2$—, A is SR, B is OH or SR''', where R''' is

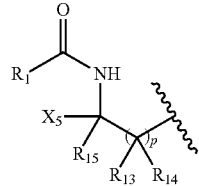

9A. A compound according to any one of item 1A-3A, wherein Z is

—CH$_2$CH$_2$—, A is NR, B is OH and R is

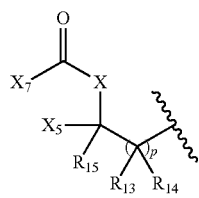

and X is S.

10A. A compound according to any of the preceding items, wherein R and/or R''' is

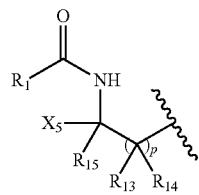

and p=1 and X$_5$ is —H such that formula (VII) is

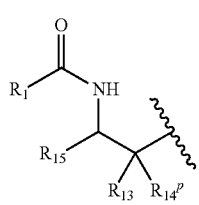
(VII)

11A. A compound according to any of items 1A-9A, wherein R and/or R''' is

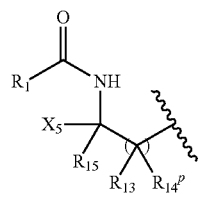

and p=1 and X$_5$ is COXR$_6$ such that formula (VII) is

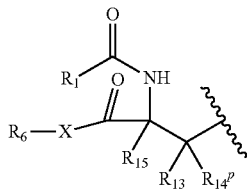
(VII)

12A. A compound according to any of items 1A-9A, wherein R and/or R''' is

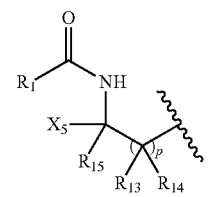

and p=1 and X$_5$ is CONR$_1$R$_3$ such that formula (VII) is

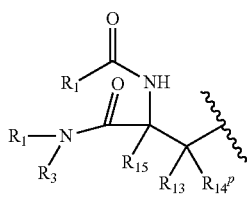
(VII)

13A. A compound according to any one of the preceding items, wherein the compound is selected from:

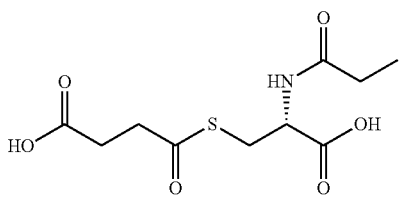

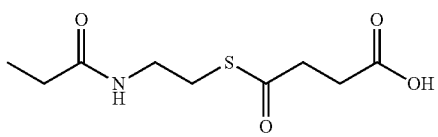

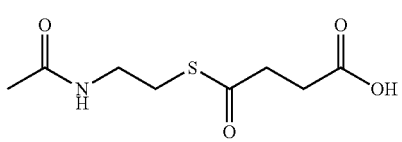

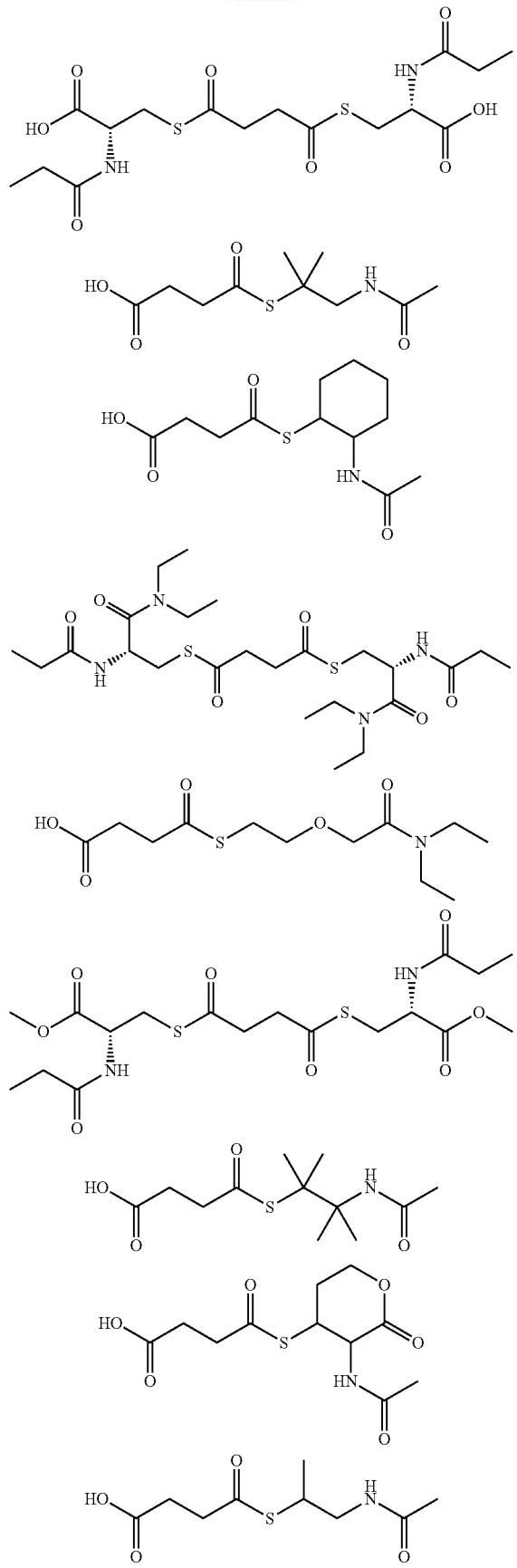
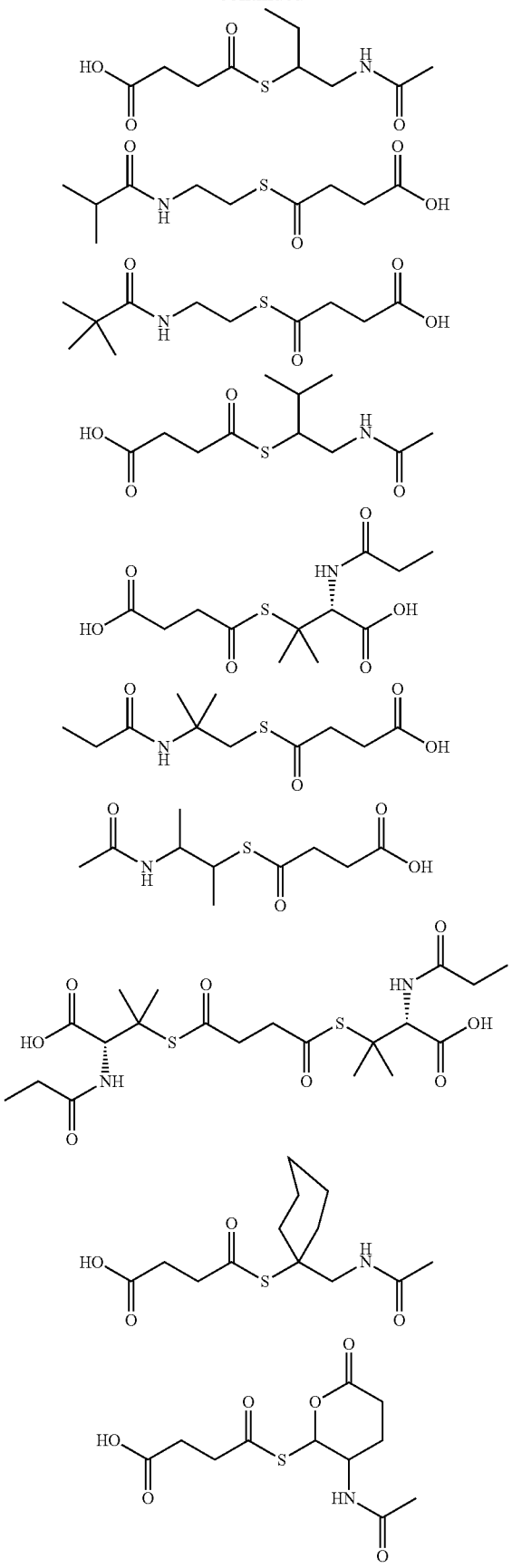

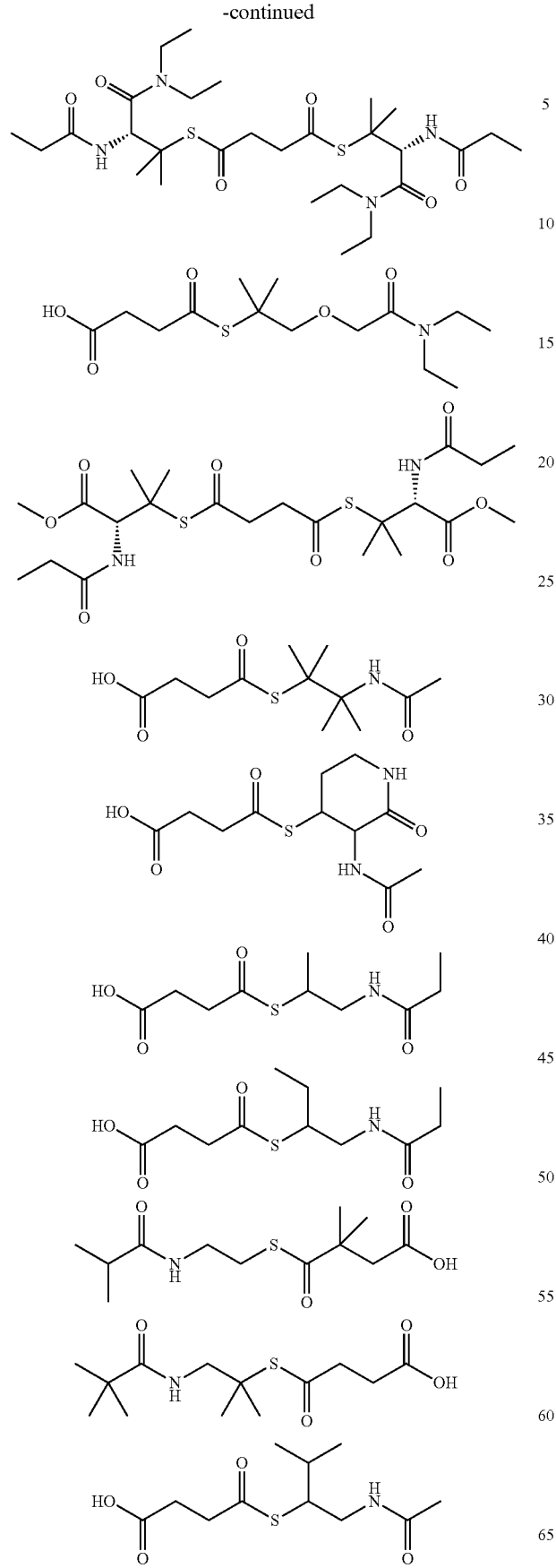
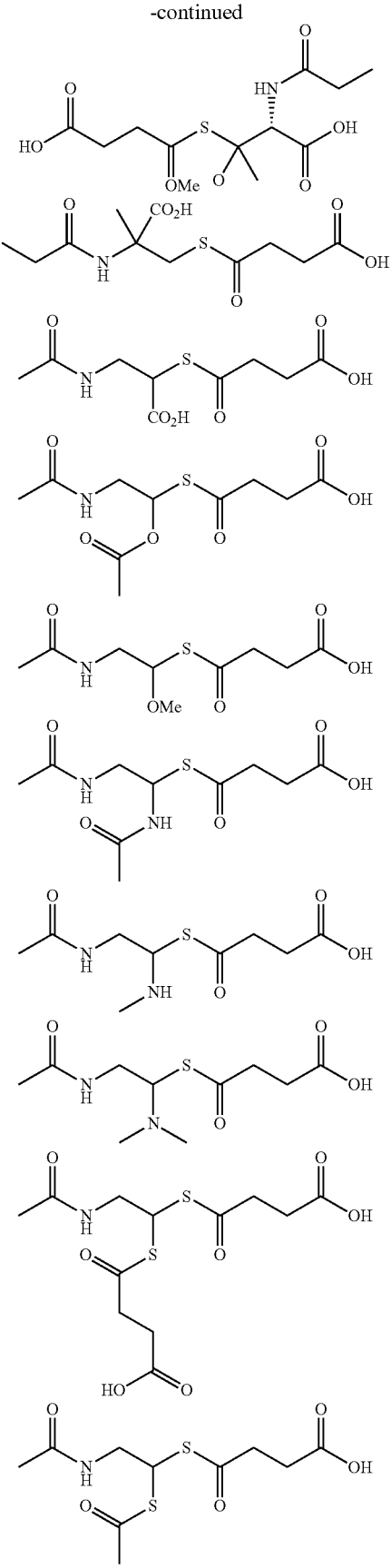

Other suitable compounds are seen from the following list (B)
1. A compound according to Formula (I)

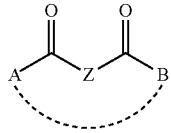
(I)

or a pharmaceutically acceptable salt thereof, where the dotted bond denotes an optional bond between A and B to form a cyclic structure, and wherein Z is selected from —$CH_2$—$CH_2$— or >CH($CH_3$), A and B are independently different or the same and are selected from —OR, —O—R', —NHR", —SR'" or —OH, both A and B are not —OH, wherein R is

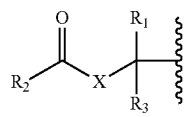

R' is selected from the formula (II), (V) or (IX) below:

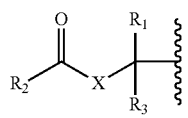
(II)

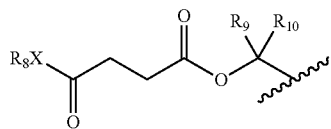
(V)

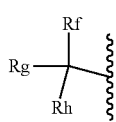
(IX)

R', R" and R'" are independently different or identical and is selected from formula (VII-VIII) below:

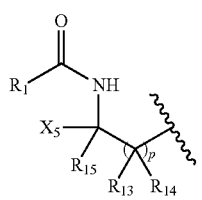
(VII)

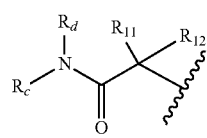
(VIII)

$R_1$ and $R_3$ are independently different or identical and are selected from H, Me, Et, propyl, i-propyl, butyl, iso-butyl, t-butyl, O-acyl, O-alkyl, N-acyl, N-alkyl, Xacyl, $CH_2$Xalkyl, $CH_2CH_2CH_2OC(=O)CH_2CH_2COX_6R_8$ or

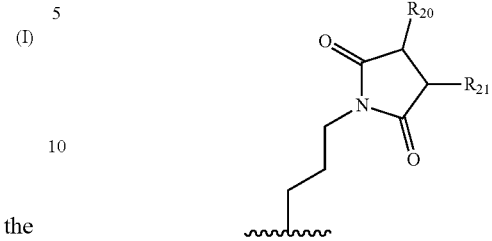

X is selected from O, NH, $NR_6$, S, $R_2$ is selected from Me, Et, propyl, i-propyl, butyl, iso-butyl, t-butyl, $C(O)CH_3$, $C(O)CH_2C(O)CH_3$, $C(O)CH_2CH(OH)CH_3$, p is an integer and is 1 or 2, $R_6$ is selected from H, alkyl, Me, Et, propyl, i-propyl, butyl, iso-butyl, t-butyl, acetyl, acyl, propionyl, benzoyl, or formula (II), or formula (VIII)

$X_5$ is selected from —H, —COOH, —C(=O)$XR_6$, $CONR_1R_3$ or one of the formulas

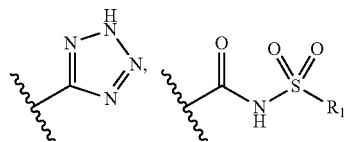

$R_9$ is selected from H, Me, Et or $O_2CCH_2CH_2COXR_8$, $R_{10}$ is selected from Oacyl, NHalkyl, NHacyl, or $O_2CCH_2CH_2CO\,X_6R_8$, $X_6$ is O or $NR_8$, and $R_8$ is selected from H, alkyl, Me, Et, propyl, i-propyl, butyl, iso-butyl, t-butyl, acetyl, acyl, propionyl, benzoyl, or formula (II), or formula (VIII), $R_{11}$ and $R_{12}$ are independently the same or different and are selected from H, alkyl, Me, Et, propyl, i-propyl, butyl, iso-butyl, t-butyl, acetyl, acyl, propionyl, benzoyl, acyl, —$CH_2$Xalkyl, —$CH_2$Xacyl, where X is selected from O, $NR_6$ or S, $R_{13}$, $R_{14}$ and $R_{15}$ are independently different or identical and are selected from H, Me, Et, propyl, i-propyl, butyl, iso-butyl, t-butyl, —COOH, O-acyl, O-alkyl, N-acyl, N-alkyl, Xacyl, $CH_2$Xalkyl $R_c$ and $R_d$ are independently $CH_2$Xalkyl, $CH_2$Xacyl, where X=O, $NR_6$ or S, and alkyl is e.g. H, Me, Et, propyl, i-propyl, butyl, iso-butyl, t-butyl, and acyl is e.g. formyl, acetyl, propionyl, isopropionyl, byturyl, tert-butyryl, pentanoyl, benzoyl or the like, $R_f$, Rg and Rh are independently selected from Xacyl, —$CH_2$Xalkyl, —$CH_2$X-acyl and $R_9$, alkyl is selected from methyl, ethyl, propyl, isopropyl, n-butyl, isobutyl, sec-butyl, tert-butyl, n-pentyl, neopentyl, isopentyl, hexyl, isohexyl, heptyl, octyl, nonyl or decyl, and acyl is selected from formyl, acetyl, propionyl, butyryl pentanoyl, benzoyl and the like, $R_{20}$ and $R_{21}$ are independently different or identical and are selected from H, lower alkyl, i.e. $C_1$-$C_4$ alkyl or $R_{20}$ and $R_{21}$ together may form a $C_4$-$C_7$ cycloalkyl or an aromatic group, both of which may optionally be substituted with halogen, hydroxyl or a lower alkyl, or $R_{20}$ and $R_{21}$ may be

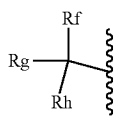

or

CH$_2$X-acyl, F, CH$_2$COOH, CH$_2$CO$_2$alkyl, and when there is a cyclic bond present between A and B the compound is

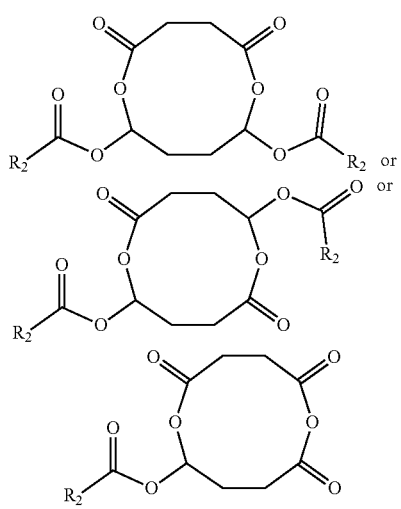

and acyls and alkyls may be optionally substituted.

2B. A compound according to item 1B, wherein Z is selected from —CH$_2$—CH$_2$— or >CH(CH$_3$), A is -selected from —O—R, wherein R is

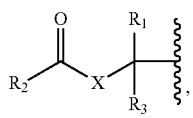

B is selected from —O—R', —NHR'', —SR''' or —OH; wherein R' is selected from the formula (II), (V) or (IX) above, R', R'' and R''' are independently different or identical and are selected from formula (VII) or formula (VIII) above.

3B. A compound according to item 1B or 2B, wherein Z is —CH$_2$CH$_2$— and A is —OR.

4B. A compound according to any of the preceding items, wherein A is —OR, and B is selected from —OR', —NHR'', —SR''' or —OH; and R', R', R'' and R''' being as described above.

5B. A compound according to any of the preceding items, wherein A is selected from —O—R, wherein R is

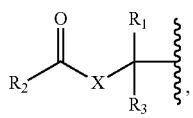

and R$_1$ or R$_3$ is CH$_2$CH$_2$CH$_2$OC(=O)CH$_2$CH$_2$COX$_6$R$_8$, and B is —OR' or —OH.

6B. A compound according to any of items 1B-4B, wherein A is —OR, and B is —OH or —OR', and wherein R' is selected from formula (VII) or formula (VIII) as defined above.

7B. A compound according to any of items 1B-4B, wherein A is selected from —O—R, wherein R is

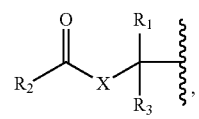

and R$_1$ or R$_3$ is

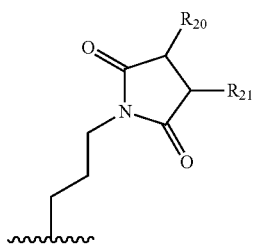

and B is —OR' or —OH.

8B. A compound according to any of the preceding items, wherein Z is —CH$_2$CH$_2$—.

9B. A compound according to any of the preceding items, wherein Z is —CH$_2$CH$_2$— and A is —OR and B is —OH.

10B. A compound according to any of the preceding items, wherein A is —OR and R is formula (II):

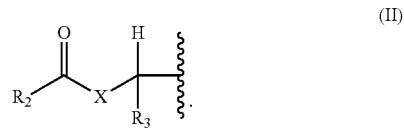

(II)

11B. A compound according to any of the preceding items, wherein formula (VII) is

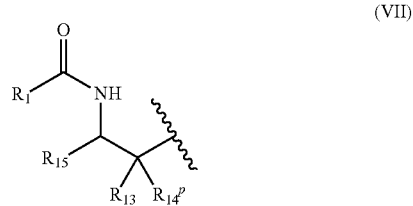

(VII)

12B. A compound according to any of the preceding items, wherein at least one of R$_f$, R$_g$, R$_h$ in formula (IX) is —H or alkyl, with alkyl as defined herein.

13B. A compound according to any of the preceding items, wherein A is —OR and R$_1$ or R$_3$ is

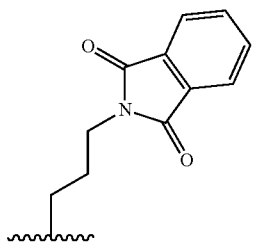 [SMILES: *CCCN1C(=O)c2ccccc2C1=O]

or R$_1$ or R$_3$ is CH$_2$CH$_2$CH$_2$OC(=O)CH$_2$CH$_2$COX$_6$R$_8$.

Definitions

The articles "a" and "an" are used herein to refer to one or to more than one (i.e. at least one) of the grammatical objects of the article. By way of example "an analogue" means one analogue or more than one analogue.

The term "succinate prodrug" is used herein to refer to a substance that i) can release succinic acid or succinate e.g. by hydrolysis or enzymatic degradation, or ii) can be converted to succinate e.g. by an enzyme. The terms "protected succinate" and precursors of succinate" are used synonymously with the term "succinate prodrug". As explained herein cell-permeable succinate prodrugs are preferred.

As used herein, the term "bioavailability" refers to the degree to which or rate at which a drug or other substance is absorbed or becomes available at the site of biological activity after administration. This property is dependent upon a number of factors including the solubility of the compound, rate of absorption in the gut, the extent of protein binding and metabolism etc. Various tests for bioavailability that would be familiar to a person of skill in the art are described herein (see also Trepanier et al, 1998, Gallant-Haidner et al, 2000).

As used herein the terms "impairment", inhibition", "defect" used in relation to Complex I of the respiratory chain is intended to denote that a given drug substance have negative effect on Complex I or on mitochondrial metabolism upstream of Complex I, which could encompass any drug effect that limits the supply of NADH to Complex I, e.g. effects on Krebs cycle, glycolysis, beta-oxidation, pyruvate metabolism and even drugs that effect the transport or levels of glucose or other complex I-related substrates). As described herein, an excess of lactate in a subject is often an indication of a negative effect on aerobic respiration including Complex I.

As used herein the term "side-effect" used in relation to the function of Complex I of the respiratory chain may be a side-effect relating to lactic acidosis or it may be a side-effect relating to idiosyncratic drug organ toxicity e.g. hepatotoxicity, neurotoxicity, cardiotoxicity, renal toxicity and muscle toxicity encompassing, but not limited to, e.g. ophthalmoplegia, myopathy, sensorineural hearing impairment, seizures, stroke, stroke-like events, ataxia, ptosis, cognitive impairment, altered states of consciousness, neuropathic pain, polyneuropathy, neuropathic gastrointestinal problems (gastroesophageal reflux, constipation, bowel pseudo-obstruction), proximal renal tubular dysfunction, cardiac conduction defects (heart blocks), cardiomyopathy, hypoglycemia, gluconeogenic defects, nonalcoholic liver failure, optic neuropathy, visual loss, diabetes and exocrine pancreatic failure, fatigue, respiratory problems including intermittent air hunger.

As used herein the term "drug-induced" in relation to the term "side-effect" is to be understood in a broad sense. Thus, not only does it include drug substances, but also other substances that may lead to unwanted presence of lactate. Examples are herbicides, toxic mushrooms, berries etc.

The pharmaceutically acceptable salts of succinate prodrugs include conventional salts formed from pharmaceutically acceptable inorganic or organic acids or bases as well as quaternary ammonium acid addition salts. More specific examples of suitable acid salts include hydrochloric, hydrobromic, sulfuric, phosphoric, nitric, perchloric, fumaric, acetic, propionic, succinic, glycolic, formic, lactic, maleic, tartaric, citric, palmoic, malonic, hydroxymaleic, phenylacetic, glutamic, benzoic, salicylic, fumaric, toluenesulfonic, methanesulfonic, naphthalene-2-sulfonic, benzenesulfonic hydroxynaphthoic, hydroiodic, malic, steroic, tannic and the like. Other acids such as oxalic, while not in themselves pharmaceutically acceptable, may be useful in the preparation of salts useful as intermediates in obtaining the compounds of the invention and their pharmaceutically acceptable salts. More specific examples of suitable basic salts include sodium, lithium, potassium, magnesium, aluminium, calcium, zinc, N,N'-dibenzylethylenediamine, chloroprocaine, choline, diethanolamine, ethylenediamine, N-methylglucamine and procaine salts.

As used herein the term "alkyl" refers to any straight or branched chain composed of only sp3 carbon atoms, fully saturated with hydrogen atoms such as e.g. —C$_n$H$_{2n+1}$ for straight chain alkyls, wherein n can be in the range of 1 and 10 such as e.g. methyl, ethyl, propyl, isopropyl, n-butyl, isobutyl, sec-butyl, tert-butyl, n-pentyl, neopentyl, iso-pentyl, hexyl, isohexyl, heptyl, octyl, nonyl or decyl. The alkyl as used herein may be further substituted.

As used herein the term "cycloalkyl" refers to a cyclic/ring structured carbon chains having the general formula of —C$_n$H$_{2n-1}$ where n is between 3-10, such as e.g. cyclopropyl, cyclobytyl, cyclopentyl, cyclohexyl, cycloheptyl or cyclooctyl, bicycle[3.2.1]octyl, spiro[4,5]decyl, norpinyl, norbonyl, norcapryl, adamantly and the like.

As used herein, the term "alkene" refers to a straight or branched chain composed of carbon and hydrogen atoms wherein at least two carbon atoms are connected by a double bond such as e.g. C$_{2-10}$ alkenyl unsaturated hydrocarbon chain having from two to ten carbon atoms and at least one double bond. C$_{2-6}$ alkenyl groups include, but are not limited to, vinyl, 1-propenyl, allyl, iso-propenyl, n-butenyl, n-pentenyl, n-hexenyl and the like.

The term "C$_{1-10}$ alkoxy" in the present context designates a group —O—C$_{1-6}$ alkyl used alone or in combination, wherein C$_{1-10}$ alkyl is as defined above. Examples of linear alkoxy groups are methoxy, ethoxy, propoxy, butoxy, pentoxy and hexoxy. Examples of branched alkoxy are iso-propoxy, sec-butoxy, tert-butoxy, iso-pentoxy and iso-hexoxy. Examples of cyclic alkoxy are cyclopropyloxy, cyclobutyloxy, cyclopentyloxy and cyclohexyloxy.

The term "C$_{3-7}$ heterocycloalkyl" as used herein denotes a radical of a totally saturated heterocycle like a cyclic hydrocarbon containing one or more heteroatoms selected from nitrogen, oxygen and sulphur independently in the cycle. Examples of heterocycles include, but are not limited to, pyrrolidine (1-pyrrolidine, 2-pyrrolidine, 3-pyrrolidine, 4-pyrrolidine, 5-pyrrolidine), pyrazolidine (1-pyrazolidine, 2-pyrazolidine, 3-pyrazolidine, 4-pyrazolidine, 5-pyrazolidine), imidazolidine (1-imidazolidine, 2-imidazolidine, 3-imidazolidine, 4-imidazolidine, 5-imidazolidine), thiazolidine (2-thiazolidine, 3-thiazolidine, 4-thiazolidine, 5-thiazolidine), piperidine (1-piperidine, 2-piperidine, 3-piperidine, 4-piperidine, 5-piperidine, 6-piperidine), piperazine (1-piperazine, 2-piperazine, 3-piperazine, 4-piperazine, 5-piperazine, 6-piperazine), morpholine (2-morpholine, 3-morpholine, 4-morpholine, 5-morpholine, 6-morpholine), thiomorpholine (2-thiomorpholine, 3-thiomorpholine, 4-thiomorpholine, 5-thiomorpholine, 6-thiomorpholine), 1,2-oxathiolane (3-(1,2-oxathiolane), 4-(1,2-oxathiolane), 5-(1,2-oxathiolane)), 1,3-dioxolane (2-(1,3-dioxolane), 3-(1,3-dioxolane), 4-(1,3-dioxolane)), tetrahydropyrane (2-tetrahydropyrane, 3-tetrahydropyrane, 4-tetrahydropyrane, 5-tetrahydropyrane, 6-tetrahydropyrane), hexahydropyradizine, (1-(hexahydropyradizine), 2-(hexahydropyradizine), 3-(hexahydropyradizine), 4-(hexahydropyradizine), 5-(hexahydropyradizine), 6-(hexahydropyradizine)).

The term "$C_{1-10}$alkyl-$C_{3-10}$cycloalkyl" as used herein refers to a cycloalkyl group as defined above attached through an alkyl group as defined above having the indicated number of carbon atoms.

The term "$C_{1-10}$ alkyl-$C_{3-7}$ heterocycloalkyl" as used herein refers to a heterocycloalkyl group as defined above attached through an alkyl group as defined above having the indicated number of carbon atoms.

The term "aryl" as used herein is intended to include carbocyclic aromatic ring systems. Aryl is also intended to include the partially hydrogenated derivatives of the carbocyclic systems enumerated below.

The term "heteroaryl" as used herein includes heterocyclic unsaturated ring systems containing one or more heteroatoms selected among nitrogen, oxygen and sulphur, such as furyl, thienyl, pyrrolyl, and is also intended to include the partially hydrogenated derivatives of the heterocyclic systems enumerated below.

The terms "aryl" and "heteroaryl" as used herein refers to an aryl, which can be optionally unsubstituted or mono-, di- or tri substituted, or a heteroaryl, which can be optionally unsubstituted or mono-, di- or tri substituted. Examples of "aryl" and "heteroaryl" include, but are not limited to, phenyl, biphenyl, indenyl, naphthyl (1-naphthyl, 2-naphthyl), N-hydroxytetrazolyl, N-hydroxytriazolyl, N-hydroxyimidazolyl, anthracenyl (1-anthracenyl, 2-anthracenyl, 3-anthracenyl), phenanthrenyl, fluorenyl, pentalenyl, azulenyl, biphenylenyl, thiophenyl (1-thienyl, 2-thienyl), furyl (1-furyl, 2-furyl), furanyl, thiophenyl, isoxazolyl, isothiazolyl, 1,2,3-triazolyl, 1,2,4-triazolyl, pyranyl, pyridazinyl, pyrazinyl, 1,2,3-triazinyl, 1,2,4-triazinyl, 1,3,5-triazinyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, tetrazolyl, thiadiazinyl, indolyl, isoindolyl, benzofuranyl, benzothiophenyl (thianaphthenyl), indolyl, oxadiazolyl, isoxazolyl, quinazolinyl, fluorenyl, xanthenyl, isoindanyl, benzhydryl, acridinyl, benzisoxazolyl, purinyl, quinazolinyl, quinolizinyl, quinolinyl, isoquinolinyl, quinoxalinyl, naphthyridinyl, phteridinyl, azepinyl, diazepinyl, pyrrolyl (2-pyrrolyl), pyrazolyl (3-pyrazolyl), 5-thiophene-2-yl-2H-pyrazol-3-yl, imidazolyl (1-imidazolyl, 2-imidazolyl, 4-imidazolyl, 5-imidazolyl), triazolyl (1,2,3-triazol-1-yl, 1,2,3-triazol-2-yl, 1,2,3-triazol-4-yl, 1,2,4-triazol-3-yl), oxazolyl (2-oxazolyl, 4-oxazolyl, 5-oxazolyl), thiazolyl (2-thiazolyl, 4-thiazolyl, 5-thiazolyl), pyridyl (2-pyridyl, 3-pyridyl, 4-pyridyl), pyrimidinyl (2-pyrimidinyl, 4-pyrimidinyl, 5-pyrimidinyl, 6-pyrimidinyl), pyrazinyl, pyridazinyl (3-pyridazinyl, 4-pyridazinyl, 5-pyridazinyl), isoquinolyl (1-isoquinolyl, 3-isoquinolyl, 4-isoquinolyl, 5-isoquinolyl, 6-isoquinolyl, 7-isoquinolyl, 8-isoquinolyl), quinolyl (2-quinolyl, 3-quinolyl, 4-quinolyl, 5-quinolyl, 6-quinolyl, 7-quinolyl, 8-quinolyl), benzo[b]furanyl (2-benzo[b]furanyl, 3-benzo[b]furanyl, 4-benzo[b]furanyl, 5-benzo[b]furanyl, 6-benzo[b]furanyl, 7-benzo[b]furanyl), 2,3-dihydro-benzo[b]furanyl (2-(2,3-dihydro-benzo[b]furanyl), 3-(2,3-dihydro-benzo[b]furanyl), 4-(2,3-dihydro-benzo[b]furanyl), 5-(2,3-dihydro-benzo[b]furanyl), 6-(2,3-dihydro-benzo[b]furanyl), 7-(2,3-dihydro-benzo[b]furanyl)), benzo[b]thiophenyl (2-benzo[b]thiophenyl, 3-benzo[b]thiophenyl, 4-benzo[b]thiophenyl, 5-benzo[b]thiophenyl, 6-benzo[b]thiophenyl, 7-benzo[b]thiophenyl), 2,3-dihydro-benzo[b]thiophenyl (2-(2,3-dihydro-benzo[b]thiophenyl), 3-(2,3-dihydro-benzo[b]thiophenyl), 4-(2,3-dihydro-benzo[b]thiophenyl), 5-(2,3-dihydro-benzo[b]thiophenyl), 6-(2,3-dihydro-benzo[b]thiophenyl), 7-(2,3-dihydro-benzo[b]thiophenyl)), indolyl (1-indolyl, 2-indolyl, 3-indolyl, 4-indolyl, 5-indolyl, 6-indolyl, 7-indolyl), indazolyl (1-indazolyl, 2-indazolyl, 3-indazolyl, 4-indazolyl, 5-indazolyl, 6-indazolyl, 7-indazolyl), benzimidazolyl, (1-benzimidazolyl, 2-benzimidazolyl, 4-benzimidazolyl, 5-benzimidazolyl, 6-benzimidazolyl, 7-benzimidazolyl, 8-benzimidazolyl), benzoxazolyl (1-benzoxazolyl, 2-benzoxazolyl), benzothiazolyl (1-benzothiazolyl, 2-benzothiazolyl, 4-benzothiazolyl, 5-benzothiazolyl, 6-benzothiazolyl, 7-benzothiazolyl), carbazolyl (1-carbazolyl, 2-carbazolyl, 3-carbazolyl, 4-carbazolyl). Non-limiting examples of partially hydrogenated derivatives are 1,2,3,4-tetrahydronaphthyl, 1,4-dihydronaphthyl, pyrrolinyl, pyrazolinyl, indolinyl, oxazolidinyl, oxazolinyl, oxazepinyl and the like.

As used herein the term "acyl" refers to a carbonyl group —C(=O) R wherein the R group is any of the above defined groups. Specific examples are formyl, acetyl, propionyl, byturyl pentanoyl, benzoyl and the likes.

Exemplary compounds are shown below as Nos. 1-18. Other exemplary compounds are given in the lists herein:

1 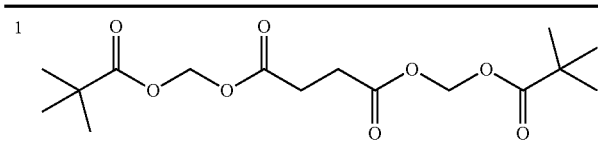

Succinic acid bis (2,2-dimethylpropionyloxymethyl) ester; compound AN-192 in WO0228345

2 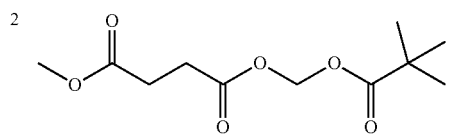

Succinic acid 2,2-dimethylpropionyloxymethyl ester methyl ester

3 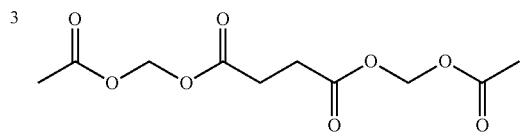

Succinic acid diacetoxymethyl ester (NV 118)

-continued

| | | |
|---|---|---|
| 4 | 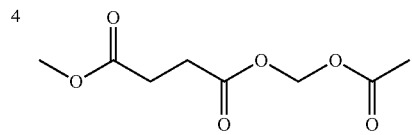 | Succinic acid acetoxy-methyl ester methyl ester |
| 5 | 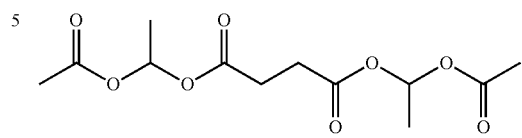 | Succinic acid bis-(1-acetoxy-ethyl) ester (NV 189) |
| 6 | 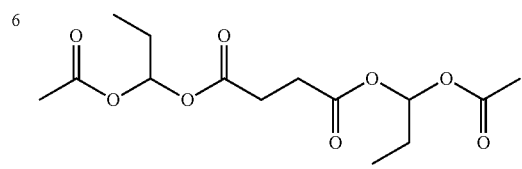 | Succinic acid 1-acetoxy-ethyl ester methyl ester |
| 7 | 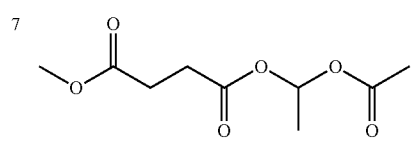 | Succinic acid bis-(1-acetoxy-propyl) ester |
| 8 | 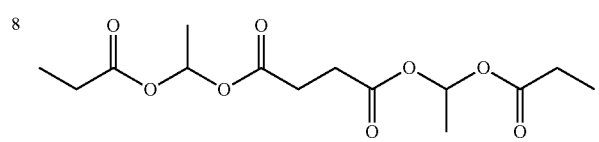 | Succinic acid bis-(1-propionyloxy-ethyl) ester |
| 9 | 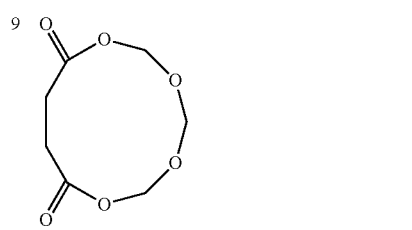 | 1,3,5,7-Tetraoxa-cycloundecane-8,11-dione |
| 10 | 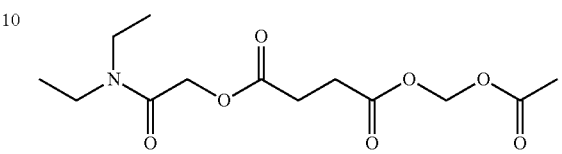 | Succinic acid acetoxy-methyl ester diethylcarbamoylmethyl ester |
| 11 | 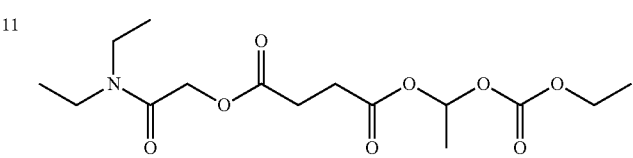 | Succinic acid diethylcarbamoylmethyl ester 1-ethoxycarbonyloxy-ethyl ester |
| 12 | 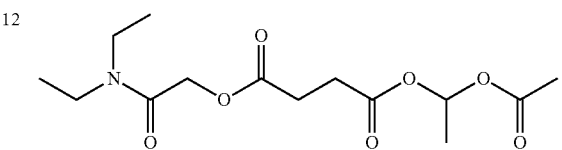 | Succinic acid 1-acetoxy-ethyl ester diethylcarbamoylmethyl ester |
| 13 | 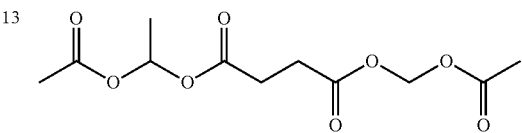 | Succinic acid 1-acetoxy-ethyl ester acetoxymethyl ester (NV 241) |

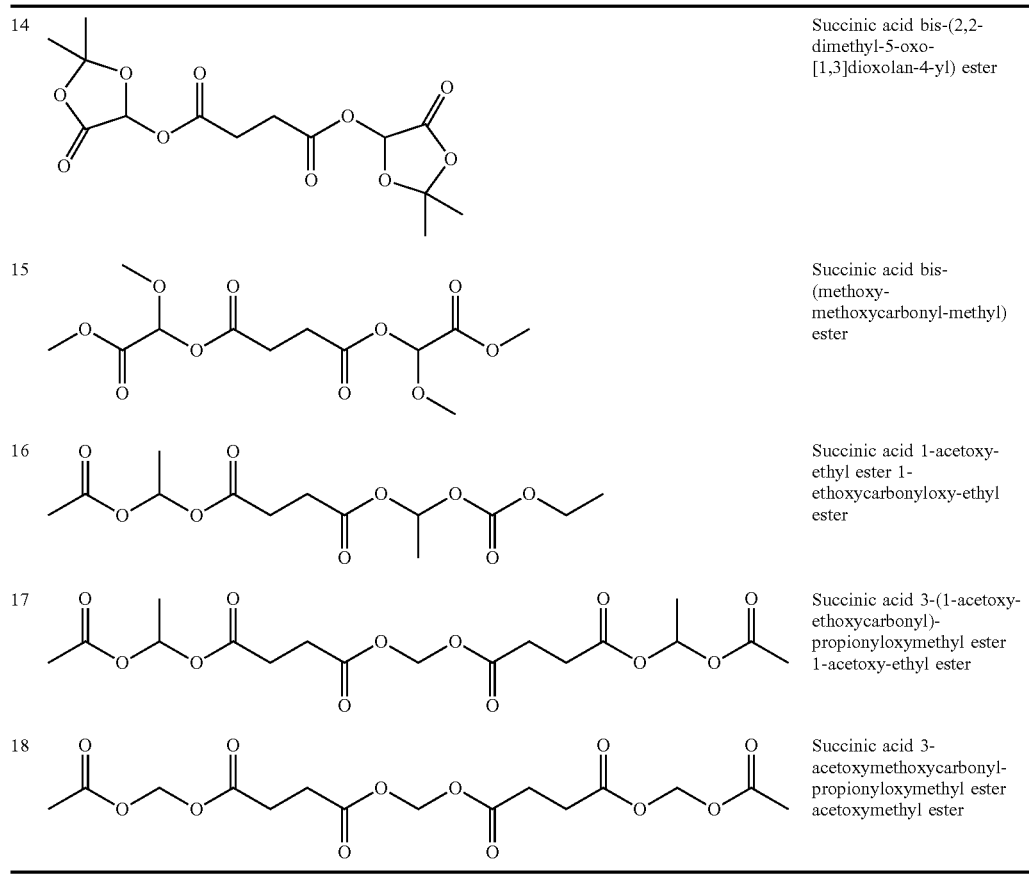

| | | |
|---|---|---|
| 14 | | Succinic acid bis-(2,2-dimethyl-5-oxo-[1,3]dioxolan-4-yl) ester |
| 15 | | Succinic acid bis-(methoxy-methoxycarbonyl-methyl) ester |
| 16 | | Succinic acid 1-acetoxy-ethyl ester 1-ethoxycarbonyloxy-ethyl ester |
| 17 | | Succinic acid 3-(1-acetoxy-ethoxycarbonyl)-propionyloxymethyl ester 1-acetoxy-ethyl ester |
| 18 | | Succinic acid 3-acetoxymethoxycarbonyl-propionyloxymethyl ester acetoxymethyl ester |

Drug substances that are known to give rise in Complex I defects, malfunction or impairment and/or are known to have lactic acidosis as side-effect are:

Analgesics including acetaminophen, capsaicin
Antianginals including amiodarone, perhexiline
Antibiotics including linezolid, trovafloxacin, gentamycin
Anticancer drugs including quinones including mitomycin C, adriamycin
Anti-convulsant drugs including valproic acid
Anti-diabetics including metformin, phenformin, butyl-biguanide, troglitazone and rosiglitazone, pioglitazone
Anti-Hepatitis B including fialuridine
Antihistamines
Anti-Parkinson including tolcapone
Anti-psycotics Risperidone,
Anti-schizoprenia zotepine, clozapine
Antiseptics, quaternary ammonium compounds (QAC)
Anti-tuberculosis including isoniazid
Fibrates including clofibrate, ciprofibrate, simvastatin
Hypnotics including Propofol
Immunosupressive disease-modifying antirheumatic drug (DMARD) Leflunomide
Local anaesthetics including bupivacaine, diclofenac, indomethacin, and lidocaine
Muscle relaxant including dantrolene
Neuroleptics including antipsycotic neuroleptics like chlorpromazine, fluphenazine and haloperidol
NRTI (Nucleotide reverse Transcriptase Inhibitors) including efavirenz, tenofovir, emtricitabine, zidovudine, lamivudine, rilpivirine, abacavir, didanosine
NSAIDs including nimesulfide, mefenamic acid, sulindac
Barbituric acids.

Other drug substances that are known to have lactic acidosis as side-effects include beta2-agonists, epinephrine, theophylline. Alcohols and cocaine can also result in lactic acidosis.

Moreover, it is contemplated that the succinate prodrugs also may be effective in the treatment or prevention of lactic acidosis even if it is not related to a Complex I defect.

Combination of Drugs and Succinate Prodrugs

The present invention also relates to a combination of a drug substance and a succinate prodrug for use in the treatment and/or prevention of a drug-induced side-effect selected from lactic acidosis and side-effect related to a Complex I defect, inhibition or malfunction, wherein i) the drug substance is used for treatment of a disease for which the drug substance is indicated, and ii) the succinate prodrug is used for prevention or alleviation of the side effects induced or inducible by the drug substance, wherein the side-effects are selected from lactic acidosis and side-effects related to a Complex I defect, inhibition or malfunction.

Any combination of such a drug substance with any succinate prodrug is within the scope of the present invention. Accordingly, based on the disclosure herein a person skilled in the art will understand that the gist of the invention is the findings of the valuable properties of succinate prodrugs to avoid or reduce the side-effects described herein. Thus, the potential use of succinate prodrugs capable of entering cells and deliver succinate and possibly other active moeities in combination with any drug substance that has or potentially have the side-effects described herein is evident from the present disclosure.

The invention further relates to i) a composition comprising a drug substance and a succinate prodrug, wherein the drug substance has a potential drug-induced side-effect selected from lactic acidosis and side-effects related to a Complex I defect, inhibition or malfunction, ii) a composition as described above under i), wherein the succinate prodrug is used for prevention or alleviation of side effects induced or inducible by the drug substance, wherein the side-effects are selected from lactic acidosis and side-effects related to a Complex I defect, inhibition or malfunction.

The composition may be in the form of two separate packages:

A first package containing the drug substance or a composition comprising the drug substance and a second package containing the succinate prodrug or a composition comprising the succinate prodrug. The composition may also be a single composition comprising both the drug substance and the succinate prodrug.

In the event that the composition comprises two separate packages, the drug substance and the succinate prodrug may be administered by different administration routes (e.g. drug substance via oral administration and succinate prodrug by parenteral or mucosal administration) and/or they may be administered essentially at the same time or the drug substance may be administered before the succinate prodrug or vice versa.

The succinate prodrugs, combinations or compositions thereof may be administered by any conventional method for example but without limitation parenterally, orally, topically (including buccal, sublingual or transdermal), via a medical device (e.g. a stent), by inhalation or via injection (subcutaneous or intramuscular). The treatment may consist of a single dose or a plurality of doses over a period of time.

Whilst it is possible for the compound of the invention to be administered alone, it is preferable to present it as a pharmaceutical formulation, together with one or more acceptable carriers. The carrier(s) must be "acceptable" in the sense of being compatible with the compound of the invention and not deleterious to the recipients thereof. Examples of suitable carriers are described in more detail below.

The compositions may conveniently be presented in unit dosage form and may be prepared by any of the methods well known in the art of pharmacy. Such methods include the step of bringing into association the active ingredient (succinate prodrug and, optionally a drug substance as described herein) with the carrier which constitutes one or more accessory ingredients. In general the formulations are prepared by uniformly and intimately bringing into association the active ingredient with liquid carriers or finely divided solid carriers or both, and then, if necessary, shaping the product.

The succinate prodrugs, combinations or compositions thereof will normally be administered intravenously, orally or by any parenteral route, in the form of a pharmaceutical formulation comprising the active ingredient, optionally in the form of a non-toxic organic, or inorganic, acid, or base, addition salt, in a pharmaceutically acceptable dosage form. Depending upon the disorder and patient to be treated, as well as the route of administration, the compositions may be administered at varying doses.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability.

The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), vegetable oils, and suitable mixtures thereof.

For example, the compound of the invention can be administered orally, buccally or sublingually in the form of tablets, capsules, ovules, elixirs, solutions or suspensions, which may contain flavouring or colouring agents, for immediate-, delayed- or controlled-release applications.

Solutions or suspensions of the compound of the invention suitable for oral administration may also contain excipients e.g. N,N-dimethylacetamide, dispersants e.g. polysorbate 80, surfactants, and solubilisers, e.g. polyethylene glycol, Phosal 50 PG (which consists of phosphatidylcholine, soya-fatty acids, ethanol, mono/diglycerides, propylene glycol and ascorbyl palmitate).

Such tablets may contain excipients such as microcrystalline cellulose, lactose (e.g. lactose monohydrate or lactose anhydrous), sodium citrate, calcium carbonate, dibasic calcium phosphate and glycine, butylated hydroxytoluene (E321), crospovidone, hypromellose, disintegrants such as starch (preferably corn, potato or tapioca starch), sodium starch glycollate, croscarmellose sodium, and certain complex silicates, and granulation binders such as polyvinylpyrrolidone, hydroxypropylmethylcellulose (HPMC), hydroxypropylcellulose (HPC), macrogol 8000, sucrose, gelatin and acacia. Additionally, lubricating agents such as magnesium stearate, stearic acid, glyceryl behenate and talc may be included. Hydroxypropylmethylcellulose acetate succinate is also available as an excipient. However, this substance is not encompassed within the present invention as it appears only to release succinate at temperatures above body temperature.

Solid compositions of a similar type may also be employed as fillers in gelatin capsules. Preferred excipients in this regard include lactose, starch, a cellulose, milk sugar or high molecular weight polyethylene glycols. For aqueous suspensions and/or elixirs, the compounds of the invention may be combined with various sweetening or flavouring agents, colouring matter or dyes, with emulsifying and/or suspending agents and with diluents such as water, ethanol, propylene glycol and glycerin, and combinations thereof.

A tablet may be made by compression or moulding, optionally with one or more accessory ingredients. Compressed tablets may be prepared by compressing in a suitable machine the active ingredient in a free-flowing form such as a powder or granules, optionally mixed with a binder (e.g. povidone, gelatin, hydroxypropylmethyl cellulose), lubricant, inert diluent, preservative, disintegrant (e.g. sodium starch glycolate, cross-linked povidone, cross-linked sodium carboxymethyl cellulose), surface-active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein using, for example, hydroxypropylmethylcellulose in varying proportions to provide desired release profile.

Formulations in accordance with the present invention suitable for oral administration may be presented as discrete units such as capsules, cachets or tablets, each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

Formulations suitable for topical administration in the mouth include lozenges comprising the active ingredient in a flavoured basis, usually sucrose and acacia or tragacanth; pastilles comprising the active ingredient in an inert basis such as gelatin and glycerin, or sucrose and acacia; and mouth-washes comprising the active ingredient in a suitable liquid carrier.

It should be understood that in addition to the ingredients particularly mentioned above the formulations of this invention may include other agents conventional in the art having regard to the type of formulation in question, for example those suitable for oral administration may include flavouring agents.

Pharmaceutical compositions adapted for topical administration may be formulated as ointments, creams, suspensions, lotions, powders, solutions, pastes, gels, impregnated dressings, sprays, aerosols or oils, transdermal devices, dusting powders, and the like. These compositions may be prepared via conventional methods containing the active agent. Thus, they may also comprise compatible conventional carriers and additives, such as preservatives, solvents to assist drug penetration, emollient in creams or ointments and ethanol or oleyl alcohol for lotions. Such carriers may be present as from about 1% up to about 98% of the composition. More usually they will form up to about 80% of the composition. As an illustration only, a cream or ointment is prepared by mixing sufficient quantities of hydrophilic material and water, containing from about 5-10% by weight of the compound, in sufficient quantities to produce a cream or ointment having the desired consistency.

Pharmaceutical compositions adapted for transdermal administration may be presented as discrete patches intended to remain in intimate contact with the epidermis of the recipient for a prolonged period of time. For example, the active agent may be delivered from the patch by iontophoresis.

For applications to external tissues, for example the mouth and skin, the compositions are preferably applied as a topical ointment or cream. When formulated in an ointment, the active agent may be employed with either a paraffinic or a water-miscible ointment base.

Alternatively, the active agent may be formulated in a cream with an oil-in-water cream base or a water-in-oil base.

For parenteral administration, fluid unit dosage forms are prepared utilizing the active ingredient and a sterile vehicle, for example but without limitation water, alcohols, polyols, glycerine and vegetable oils, water being preferred. The active ingredient, depending on the vehicle and concentration used, can be either suspended or dissolved in the vehicle. In preparing solutions the active ingredient can be dissolved in water for injection and filter sterilised before filling into a suitable vial or ampoule and sealing.

The compositions may contain additives such as viscosity-adjusting agents, pH-adjusting agents, tonicity-adjusting agent, stabilizing agents, preservatives etc.

Advantageously, agents such as local anaesthetics, preservatives and buffering agents can be dissolved in the vehicle. To enhance the stability, the composition can be frozen after filling into the vial and the water removed under vacuum. The dry lyophilized powder is then sealed in the vial and an accompanying vial of water for injection may be supplied to reconstitute the liquid prior to use.

Parenteral suspensions are prepared in substantially the same manner as solutions, except that the active ingredient is suspended in the vehicle instead of being dissolved and sterilization cannot be accomplished by filtration. The active ingredient can be sterilised by exposure to ethylene oxide before suspending in the sterile vehicle. Advantageously, a surfactant or wetting agent is included in the composition to facilitate uniform distribution of the active ingredient.

It will be recognized by one of skill in the art that the optimal quantity and spacing of individual dosages of a compound of the invention will be determined by the nature and extent of the condition being treated, the form, route and site of administration, and the age and condition of the particular subject being treated, and that a physician will ultimately determine appropriate dosages to be used. This dosage may be repeated as often as appropriate. If side effects develop the amount and/or frequency of the dosage can be altered or reduced, in accordance with normal clinical practice.

Kits

The invention also provides a kit comprising i) a first container comprising a drug substance, which has a potential drug-induced side-effect selected from lactic acidosis and side-effects related to a Complex I defect, inhibition or malfunction, and ii) a second container comprising a succinate prodrug, which has the potential for prevention or alleviation of the side effects induced or inducible by the drug substance, wherein the side-effects are selected from lactic acidosis and side-effects related to a Complex I defect, inhibition or malfunction.

Method for Treatment/Prevention

The invention also relates to a method for treating a subject suffering from a drug-induced side-effect selected from lactic acidosis and side-effect related to a Complex I defect, inhibition or malfunction, the method comprises administering an effective amount of a succinate prodrug to the subject, and to a method for preventing or alleviating a drug-induced side-effect selected from lactic acidosis and side-effect related to a Complex I defect, inhibition or malfunction in a subject, who is suffering from a disease that is treated with a drug substance, which potentially induce a side-effect selected from lactic acidosis and side-effect related to a Complex I defect, inhibition or malfunction, the method comprises administering an effective amount of a succinate prodrug to the subject before, during or after treatment with said drug substance.

Details and particulars described for one aspect of the invention apply mutatis mutandis to all other aspects of the invention.

In the following the invention is illustrated by use of the drug substance metformin and the examples herein. It is not intended to limit the invention in any way.

Metformin

Metformin is an anti-diabetic drug belonging to the class of biguanides. It's the first line treatment for type 2 diabetes, which accounts for around 90% of diabetes cases in the USA (Golan et al., 2012, Protti et al., 2012b). The anti-diabetic effect has been attributed to decreasing hepatic glucose production, increasing the biological effect of insulin through increased glucose uptake in peripheral tissues and decreasing uptake of glucose in the intestine, but the exact mechanisms of action have not been completely elucidated (Kirpichnikov et al., 2002, Golan et al., 2012). Despite its advantages over other anti-diabetics it has been related to rare cases of lactic acidosis (LA) as side effect (Golan et al., 2012). LA is defined as an increased anion gap, an arterial blood lactate level above 5 mM and a pH 5 7.35 (Lalau, 2010). Although the precise pathogenesis of metformin-associated LA is still not completely revealed, an inhibition of gluconeogenesis and resulting accumulation of gluconeogenic precursors, such as alanine, pyruvate and lactate, has been suggested (Salpeter et al., 2010). Others, however, propose an interference of the drug with mitochondrial function being the key factor for both the primary therapeutic, glucose-lowering effect (Owen et al., 2000, El-Mir, 2000) as well as for the development of metformin-associated LA (Protti et al., 2012b, Dykens et al., 2008, Brunmair et al., 2004). As a consequence of mitochondrial inhibition, the cell would partly shift from aerobic to anaerobic metabolism, promoting glycolysis with resulting elevated lactate levels (Owen et al., 2000). Phenformin, another anti-diabetic agent of the same drug class as metformin, has been withdrawn from the market in most countries due to a high incidence of LA (4 cases per 10000 treatment-years). In comparison, the incidence of LA for metformin is about a tenth of that for phenformin, and it is therefore considered a rather safe therapeutic agent (Sogame et al., 2009, Salpeter et al., 2010). Metformin-associated LA is seen mostly in patients who have additional predisposing conditions affecting the cardiovascular system, liver or kidneys. Under these conditions, the drug clearance from the body is impaired which, if not detected in time, results in escalating blood concentrations of metformin (Lalau, 2010, Kirpichnikov et al., 2002). Since the use of metformin is expected to rise due to increasing prevalence of type 2 diabetes (Protti et al., 2012b) the research on metformin-induced mitochondrial toxicity and LA becomes a current and urgent issue. Research on the mitochondrial toxicity of metformin reports inconsistent results. Kane et al. (2010) did not detect inhibition of basal respiration and maximal respiratory capacities by metformin in vivo in skeletal muscle from rats and neither did Larsen et al. (2012) in muscle biopsies of metformin-treated type 2 diabetes patients. In contrast, others have described toxic effects of metformin and phenformin on mitochondria and its association with LA in animal tissues (Owen et al., 2000, Brunmair et al., 2004, Carvalho et al., 2008, El-Mir, 2000, Dykens et al., 2008, Kane et al., 2010). Data on human tissue are scarce, especially ex vivo or in vivo. Most human data on metformin and LA are based on retrospective studies due to the difficulty of obtaining human tissue samples. Protti et al. (2010), however, reported decreased systemic oxygen consumption in patients with biguanide-associated LA and both Protti et al. (2012b) and Larsen et al. (2012) described mitochondrial dysfunction in vitro in response to metformin exposure at ≤10 mM in human skeletal muscle and platelets, respectively. Protti et al. (2012b) further reported on increased lactate release in human platelets in response to metformin exposure at 1 mM (Protti et al., 2012b). Although metformin is not found at this concentration at therapeutic conditions, it has been shown to approach these levels in the blood during intoxication and it is known to accumulate 7 to 10-fold in the gastrointestinal tract, kidney, liver, salivary glands, lung, spleen and muscle as compared to plasma (Graham et al., 2011, Bailey, 1992, Schulz and Schmoldt, 2003, Al-Abri et al., 2013, Protti et al., 2012b, Scheen, 1996).

In the study reported herein the aim was to assess mitochondrial toxicity of metformin and phenformin in human blood cells using high-resolution respirometry. Phenformin was included to compare activity of the two similarly structured drugs and to study the relation between mitochondrial toxicity and the incidence of LA described in human patients. In order to investigate membrane permeability and the specific target of toxicity of these biguanides, a model for testing drug toxicity was applied using both intact and permeabilized blood cells with sequential additions of respiratory complex-specific substrates and inhibitors.

LEGENDS TO FIGURES

FIG. 1 Effect of metformin on mitochondrial respiration in permeabilized human peripheral blood mononuclear cells (PBMCs) and platelets. (a) Representative traces of simultaneously measured $O_2$ consumption of metformin-(1 mM, black trace) or vehicle-treated ($H_2O$, grey trace) permeabilized PBMCs assessed by applying sequential additions of indicated respiratory complex-specific substrates and inhibitors. The stabilization phase of the traces, disturbances due to reoxygenation of the chamber and complex IV substrate administration have been omitted (dashed lines). Boxes below traces state the respiratory complexes utilized for respiration during oxidation of the given substrates, complex I (CI), complex II (CII) or both (CI+II), as well as the respiratory states at the indicated parts of the protocol. Respiratory rates at three different respiratory states and substrate combinations are illustrated for PBMCs (b) and platelets (c) for control ($H_2O$) and indicated concentrations of metformin: oxidative phosphorylation capacity supported by complex I substrates ($OXPHOS_{CI}$), complex II-dependent maximal flux through the electron transport system ($ETS_{CII}$) following titration of the protonophore FCCP, and complex IV (CIV) capacity. Values are depicted as mean±SEM. *=$P<0.05$, =$P<0.01$ and *=$P<0.001$ using one-way ANOVA with Holm-Sidak's multiple comparison method, n=5. OXPHOS=oxidative phosphorylatation. ETS=electron transport system. ROX=residual oxygen concentration.

Figure 2:
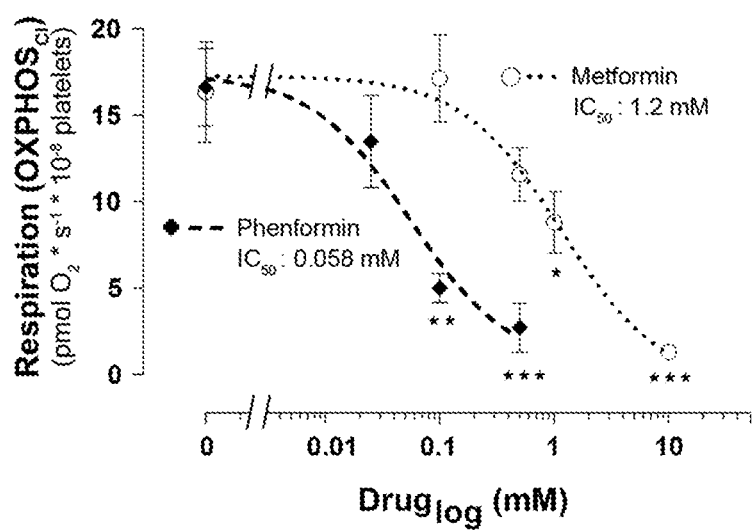

FIG. 2 Dose-response comparison of the toxicity displayed by metformin and phenformin on mitochondrial respiratory capacity during oxidative phosphorylation supported by complex I-linked substrates ($OXPHOS_{CI}$) in permeabilized human platelets. Rates of respiration are presented as mean±SEM and standard non-linear curve fitting was applied to obtain half maximal inhibitory concentration ($IC_{50}$) values for metformin and phenformin. *=$P<0.05$, =$P<0.01$ and *=$P<0.001$ compared to control using one-way ANOVA with Holm-Sidak's multiple comparison method, n=5.

Figure 3:
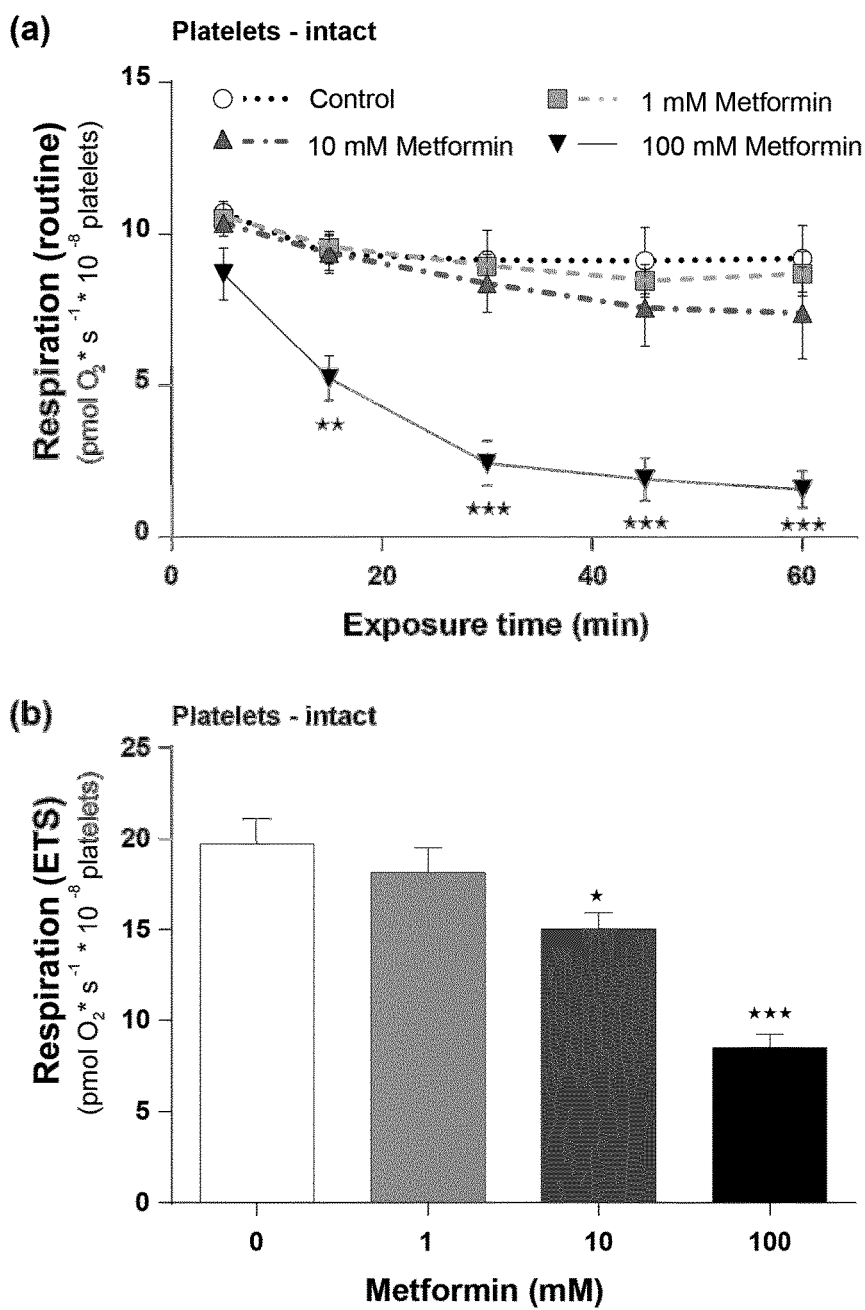

FIG. 3 Time- and dose-dependent effects of metformin on mitochondrial respiration in intact human platelets. (a) Routine respiration of platelets, i.e. respiration of the cells with their endogenous substrate supply and ATP demand, was monitored during 60 min incubation of indicated concentrations of metformin or vehicle ($H_2O$), which was followed by (b) maximal respiratory capacity induced by titration of the protonophore FCCP to determine maximal flux through the electron transport system (ETS) of the intact cells. Data are expressed as mean±SEM, n=5. *=$P<0.05$, =$P<0.01$ and *=P<0.001 using one-way ANOVA (b) and two-way ANOVA (a) with Holm-Sidak's post-hoc test.

Figure 4:
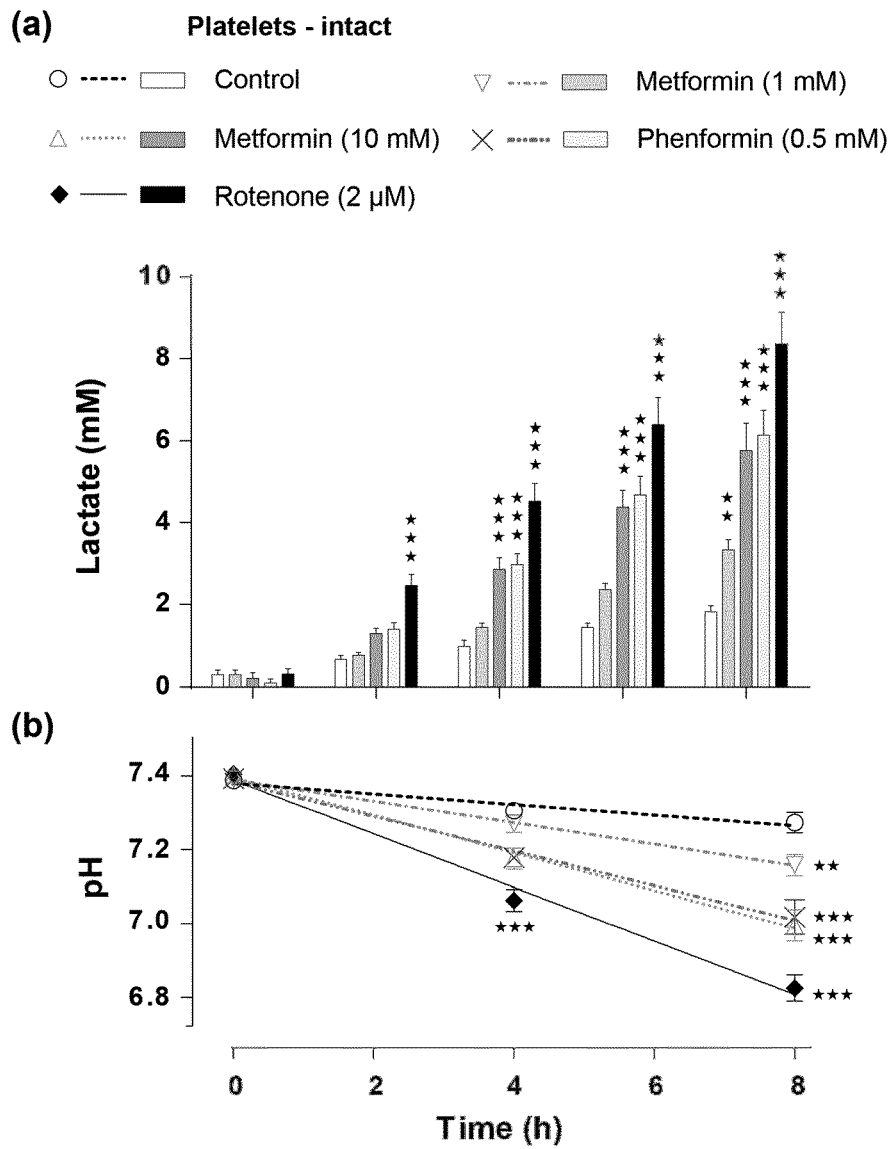

FIG. 4 Effect of metformin and phenformin on lactate production and pH in suspensions of intact human platelets. Platelets were incubated in phosphate buffered saline containing glucose (10 mM) for 8 h with either metformin (10 mM, 1 mM), phenformin (0.5 mM), the complex I inhibitor rotenone (2 µM), or vehicle (DMSO, control). (a) Lactate levels were determined every 2 h (n=5), and (b) pH was measured every 4 h (n=4). Data are expressed as mean±SEM. *=P<0.05, =P<0.01 and *=P<0.001 using two-way ANOVA with Holm-Sidak's post-hoc test.

Figure 5:
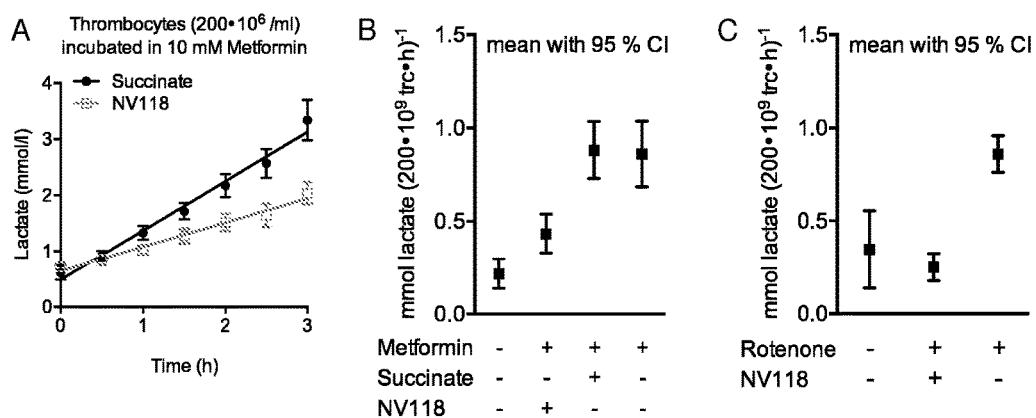

FIG. 5 Human intact thrombocytes ($200·10^6$/ml) incubated in PBS containing 10 mM glucose. (A) Cells incubated with 10 mM metformin were treated with either succinate or NV118 (compound 3) in consecutive additions of 250 µM each 30 minutes. Prior to addition of NV118 at time 0 h, cells have been incubated with just metformin or vehicle for 1 h to establish equal initial lactate levels (data not shown). Lactate concentrations were sampled each 30 minutes. (B) Lactate production was calculated with a non-linear fit regression and 95% confidence intervals for the time lactate curves were calculated. Cells incubated with metformin had a significantly higher production of lactate than control, and succinate additions did not change this. Lactate production was significantly decreased when NV118 was added to the cells incubated with metformin. (C) Lactate production induced by rotenone could similarly be attenuated by repeated additions of NV118.

Figure 6:
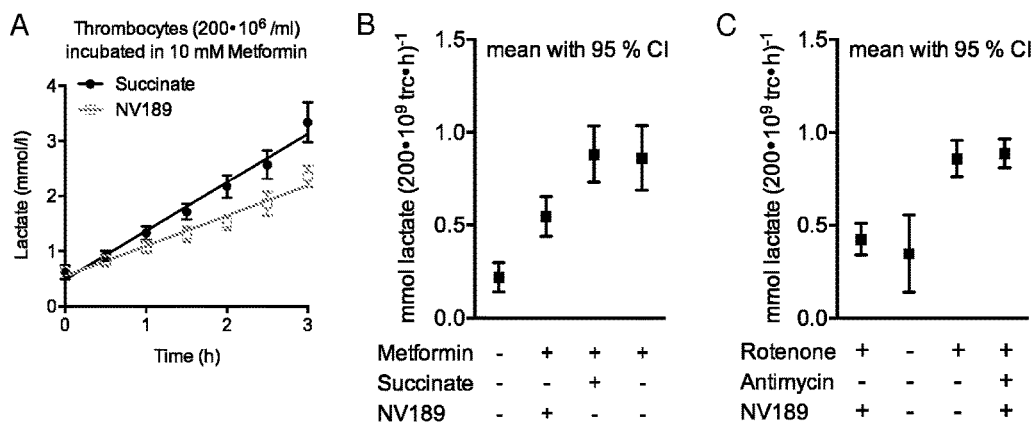

FIG. 6 Human intact thrombocytes ($200·10^6$/ml) incubated in PBS containing 10 mM glucose. (A) Cells incubated with 10 mM metformin were treated with either succinate or NV189 (compound 5) in consecutive additions of 250 µM each 30 minutes. Prior to addition of NV189 at time 0 h, cells have been incubated with just metformin or vehicle for 1 h to establish equal initial lactate levels (data not shown). Lactate concentrations were sampled each 30 minutes. (B) Lactate production was calculated with a non-linear fit regression and 95% confidence intervals for the time lactate curves were calculated. Cells incubated with metformin had a significantly higher production of lactate than control, and succinate additions did not change this. Lactate production was significantly decreased when NV189 was added to the cells incubated with metformin. (C) Lactate production induced by rotenone could similarly be attenuated by repeated additions of NV189. When antimycin also was added, the effect of NV189 on complex 2 was abolished by antimycin's inhibitory effect on complex III.

Figure 7:
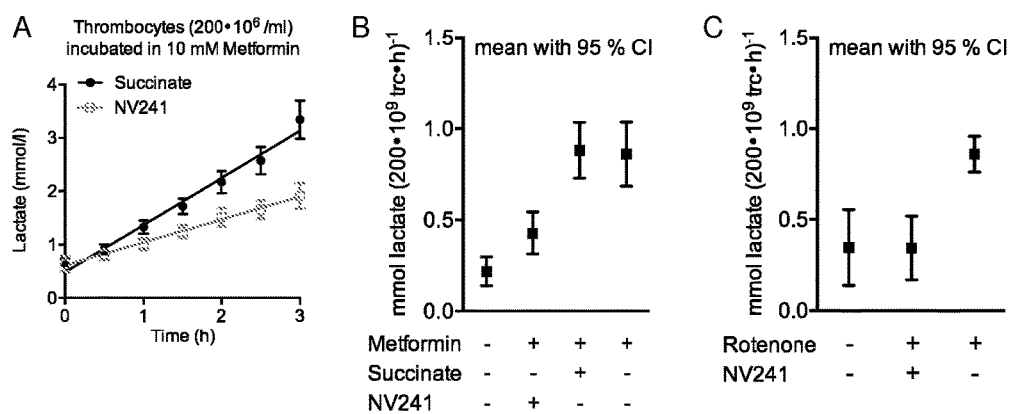

FIG. 7 Human intact thrombocytes ($200·10^6$/ml) incubated in PBS containing 10 mM glucose. (A) Cells incubated with 10 mM metformin were treated with either succinate or NV241 (compound 15) in consecutive additions of 250 µM each 30 minutes. Prior to addition of NV241 at time 0 h, cells have been incubated with just metformin or vehicle for 1 h to establish equal initial lactate levels (data not shown). Lactate concentrations were sampled each 30 minutes. (B) Lactate production was calculated with a non-linear fit regression and 95% confidence intervals for the time lactate curves were calculated. Cells incubated with metformin had a significantly higher production of lactate than control, and succinate additions did not change this. Lactate production was significantly decreased when NV241 was added to the cells incubated with metformin. (C) Lactate production induced by rotenone could similarly be attenuated by repeated additions of NV241.

Figure 8:
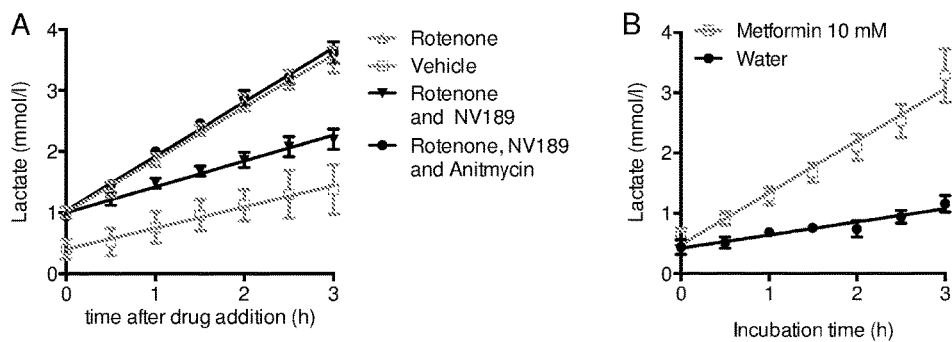

FIG. 8 Thrombocytes ($200·10^6$/ml) incubated in PBS containing 10 mM of glucose with sampling of lactate concentrations every 30 minutes. (A) During 3 hour incubation, cells treated with either rotenone (2 µM) or its vehicle is monitored for change in lactate concentration in media over time. Also, cells were incubated with rotenone together with NV189 and cells with rotenone, NV189 and the complex III inhibitor antimycin (1 µg/mL) are monitored. Prior to addition of NV189 at time 0 h, cells have been incubated with just rotenone or vehicle for 1 h to establish equal initial lactate levels (data not shown). Rotenone increase the lactate production of the cells, but this is brought back to normal (same curve slope) by co-incubation with NV189 (in consecutive additions of 250 µM each 30 minutes). When antimycin also is present, NV189 cannot function at complex II level, and lactate production is again increased to the same level as with only rotenone present. (B) A similar rate of lactate production as with rotenone can be induced by incubation with Metformin at 10 mM concentration.

Figure 9:
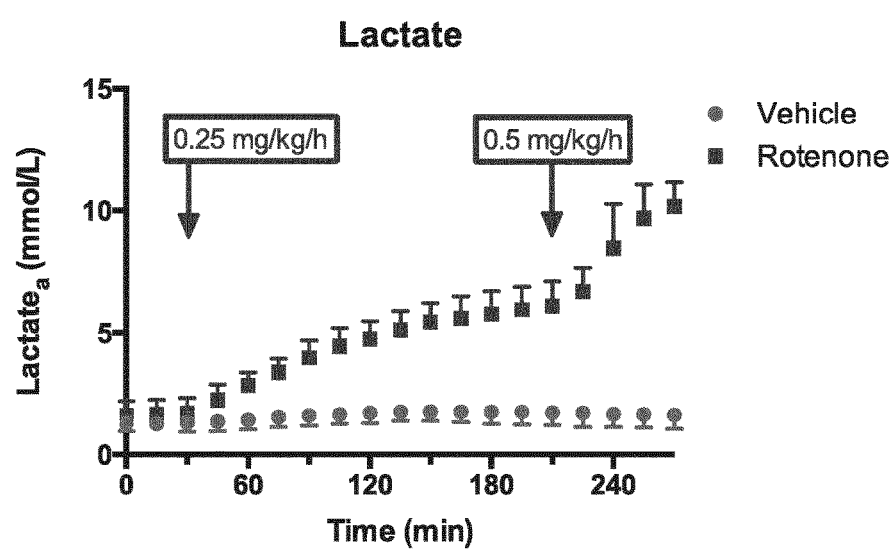

FIG. 9 Lactate accumulation in an acute metabolic crisis model in pig. In the animal model, mitochondrial function is repressed by infusion of the respiratory complex I inhibitor rotenone. As the cells shift to glycolysis lactate is accumulated in the body. Mean arterial lactate concentrations are demonstrated for rotenone and vehicle treated animals at indicated infusion rates. Drug candidates are evaluated in rotenone treated animals and decreased rate of lactate accumulation indicates restoration of mitochondrial ATP production.

EXPERIMENTAL

Materials and Methods

Unless otherwise stated, methods for assessing respiratory function of human PBMCs and platelets were according to Sjövall et al. (2013a, 2013b).

Chemicals and Materials

Lymphoprep™ was purchased from Axis-Shield PoC AS (Oslo, Norway). All remaining chemicals were obtained from Sigma-Aldrich (St. Louis, Mo., USA).

Sample Acquisition and Preparation

The study was performed with approval of the regional ethical review board of Lund University, Sweden (ethical review board permit no. 2013/181). Venous blood from 18 healthy adults (11 males and 7 females) was drawn in $K_2EDTA$ tubes (BD Vacutainer® Brand Tube with dipotassium EDTA, BD, Plymouth, UK) according to clinical standard procedure after written informed consent was acquired. For platelet isolation the whole blood was centrifuged (Multifuge 1 S-R Heraeus, Thermo Fisher Scientifics, Waltham, USA) at 500 g at room temperature (RT) for 10 min. Platelet-rich plasma was collected to 15 mL falcon tubes and centrifuged at 4600 g at RT for 8 min. The resulting pellet was resuspended in 1-2 mL of the donor's own plasma. PBMCs were isolated using Ficol gradient centrifugation (Boyum, 1968). The blood remaining after isolation of platelets was washed with an equal volume of physiological saline and layered over 3 mL of Lymphoprep™. After centrifugation at 800 g at RT (room temperature) for 30 min the PBMC layer was collected and washed with physiological saline. Following a centrifugation at 250 g at RT for 10 min the pellet of PBMCs was resuspended in two parts of physiological saline and one part of the donor's own plasma. Cell count for both PBMCs and platelets were performed using an automated hemocytometer (Swelab Alfa, Boule Medical AB, Stockholm, Sweden).

I. Assays for Evaluating Enhancement and Inhibition of Mitochondrial Energy Producing Function in Intact Cells High Resolution Respirometry—A—General Method Measurement of mitochondrial respirationise performed in a high-resolution oxygraph (Oxygraph-2k, Oroboros Instruments, Innsbruck, Austria) at a constant temperature of 37° C. Isolated human platelets, white blood cells, fibroblasts, human heart muscle fibers or other cell types containing live mitochondria are suspended in a 2 mL glass chamber at a concentration sufficient to yield oxygen consumption in the medium of 10 pmol $O_2$ $s^{-1}$ $mL^{-1}$.

High-Resolution Respirometry—B (Used in Lactate Studies)

Real-time respirometric measurements were performed using high-resolution oxygraphs (Oxygraph-2k, Oroboros Instruments, Innsbruck, Austria). The experimental conditions during the measurements were the following: 37° C., 2 mL active chamber volume and 750 rpm stirrer speed. Chamber concentrations of $O_2$ were kept between 200-50 µM with reoxygenation of the chamber during the experiments as appropriate (Sjövall et al., 2013a). For data recording, DatLab software version 4 and 5 were used (Oroboros Instruments, Innsbruck, Austria). Settings, daily calibration and instrumental background corrections were conducted according to the manufacturer's instructions. Respiratory measurements were performed in either a buffer containing 0.5 mM EGTA, 3 mM $MgCl_2$, 60 mM K-lactobionate, 20 mM Taurine, 10 mM $KH_2PO_4$, 20 mM HEPES, 110 mM sucrose and 1 g/L bovine serum albumin (MiR05) or phosphate buffered saline (PBS) with glucose (5 mM) and EGTA (5 mM), as indicated in the corresponding sections. Respiratory values were corrected for the oxygen solubility factor both media (0.92) (Pesta and Gnaiger, 2012). Lactate production of intact human platelets was determined in PBS containing 10 mM glucose. All measurements were performed at a platelet concentration of $200\times10^6$ cells per mL or a PBMC concentration of $5\times10^6$ cells per mL.

Biological Evaluation of Compounds (not used in the Lactate Studies)

Four typical evaluation protocols in intact cells are utilized.

(1) Assay for Enhancement of Mitochondrial Energy Producing Function in Cells with Inhibited Respiratory Complex I Cells are placed in a buffer containing 110 mM sucrose, HEPES 20 mM, taurine 20 mM, K-lactobionate 60 mM, $MgCl_2$ 3 mM, $KH_2PO_4$ 10 mM, EGTA 0.5 mM, BSA 1 g/l, pH 7.1. After baseline respiration with endogenous substrates is established, complex I is inhibited with Rotenone 2 µM. Compounds dissolved in DMSO are titrated in a range of 10 µM to 10 mM final concentration. Subsequently, cell membranes are permeabilised with digitonin (1 mg/1*$10^6$ plt) to allow entry of extracellularly released energy substrate or cell impermeable energy substrates. After stabilized respiration, Succinate 10 mM is added as a reference to enable respiration downstream of complex I. After the respiration stabilized the experiment is terminated by addition of Antimycin at final concentration 1 µg/mL and any residual non-mitochondrial oxygen consumption is measured. An increase in respiration rate in the described protocol is tightly coupled to ATP synthesis by oxidative phosphorylation unless cells are uncoupled (i.e. proton leak without production of ATP). Uncoupling is tested for by addition of the ATP synthase inhibitor oligomycin (1-2 µg $mL^{-1}$) in a protocol 3 where the extent of uncoupling corresponds to the respiratory rate following oligomycin addition.

(2) Assay for Enhancement and Inhibition of Mitochondrial Energy Producing Function in Intact Cells In the second protocol the same buffer is used as described above. After basal respiration is established, the mitochondrial uncoupler FCCP is added at a concentration of 2 nM to increase metabolic demand. Compounds dissolved in DMSO are titrated in several steps from 10 µM to 10 mM final concentration in order to evaluate concentration range of enhancement and/or inhibition of respiration. The experiment is terminated by addition of 2 µM Rotenone to inhibit complex I, revealing remaining substrate utilization downstream of this respiratory complex, and 1 µg/mL of the complex III inhibitor Antimycin to measure non-mitochondrial oxygen consumption.

(3) Assay to Assess Uncoupling in Intact Cells

In the third protocol, the same buffer as described above is used. After basal respiration is established, 1 mM of compound dissolved in DMSO is added. Subsequently, the ATP-synthase-inhibitor Oligomycin is added. A reduction in respiration is a measure of how much of the oxygen consumption that is coupled to ATP synthesis. No, or only a slight, reduction indicate that the compound is inducing a proton leak over the inner mitochondrial membrane. The uncoupler FCCP is then titrated to induce maximum uncoupled respiration. Rotenone (2 µM) is then added to inhibit complex I, revealing remaining substrate utilization downstream of this respiratory complex. The experiment is terminated by the addition of 1 µg/mL of the complex III inhibitor Antimycin to measure non-mitochondrial oxygen consumption.

(4) Assay for Enhancement of Mitochondrial Energy Producing Function in Cells with Inhibited Respiratory Complex I in Human Plasma Intact human blood cells are incubated in plasma from the same donor. After baseline respiration with endogenous substrates is established, complex I is inhibited with Rotenone 2 µM. Compounds dissolved in DMSO are titrated in a range of 10 µM to 10 mM final concentration. The experiment is terminated by addition of Antimycin at final concentration 1 µg/mL and any residual non-mitochondrial oxygen consumption is measured.

Properties of Desired Compound in Respiration Assays

The ideal compound stimulates respiration in the described protocols in intact cells at low concentration without inhibitory effect on either succinate stimulated respiration after permeabilization in protocol 1 or the endogenous respiration in protocol 2. The concentration span between maximal stimulatory effect and inhibition should be as wide as possible. After inhibition of respiration with mitochondrial toxins at or downstream of complex III, respiration should be halted. Please refer to FIG. 1 and the listing below.

Desired properties of compounds:
maximum value of a reached at low drug concentration.
a substantially more than a'
a approaches b'
c approaches c'
d approaches d'

Compounds impermeable to the cellular membrane are identified in the assay as:
a approaches a'

Non mitochondrial oxygen consumption induced by drug candidate is identified when
d more than d'

II. Assay for Prevention of Lactate Accumulation in Cells Exposed to a Mitochondrial Complex I Inhibitor Intact human platelets, white blood cells, fibroblasts, or other cell types containing live mitochondria are incubated in phosphate buffered saline containing 10 mM glucose for 8 h with either of the complex I inhibiting drugs metformin (10 mM), phenformin (0.5 mM) or rotenone (2 µM). The inhibition of mitochondrial ATP production through oxidative phosphorylation by these compounds increases lactate accumulation by glycolysis. Lactate levels are determined every 30 min using the Lactate Pro™ 2 blood lactate test meter (Arkray, Alere A B, Lidingö, Sweden) or similar types of measurements. Incubation is performed at 37° C. pH is measured at start, after 4 and after 8 h (or more frequently) of incubation using a Standard pH Meter, e.g. PHM210 (Radiometer, Copenhagen, Denmark). Drug candidates are added to the assay from start or following 30-60 min at concentrations within the range 10 µM-5 mM. The prevention of lactate accumulation is compared to parallel experiments with compound vehicle only, typically DMSO. In order to evaluate the specificity of the drug candidate, it is also tested in combination with a down-stream inhibitor of respiration such as the complex III inhibitor Antimycin at 1 µg/mL, which should abolish the effect of the drug candidate and restore the production of lactate. The use of antimycin is therefore also a control for undue effects of drug candidates on the lactate producing ability of the cells used in the assay (FIGS. 5, 6 and 7).

Properties of Desired Compound in Cellular Lactate Accumulation Assay (1) The ideal compound prevents the lactate accumulation induced by complex I inhibition, i.e. the lactate accumulation approaches a similar rate as that in non complex I-inhibited cells. (2) The prevention of lactate accumulation is abolished by a down-stream respiratory inhibitor such as Antimycin.

III. Assay for Prevention of Lactate Accumulation and Energetic Inhibition in an Acute Metabolic Crisis Model in Pig Lead drug candidates will be tested in a proof of concept in vivo model of metabolic crisis due to mitochondrial dysfunction at complex I. The model mimics severe conditions that can arise in children with genetic mutations in mitochondrial complex I or patients treated and overdosed with clinically used medications such as metformin, which inhibits complex I when accumulated in cells and tissues.

Female landrace pigs are used in the study. They are anaesthetized, taken to surgery in which catheters are placed for infusions and monitoring activities. A metabolic crisis is induced by infusion of the mitochondrial complex I inhibitor rotenone at a rate of 0.25 mg/kg/h during 3 h followed by 0.5 mg/kg/h infused during one hour (vehicle consisting of 25% NMP/4% polysorbate 80/71% water). Cardiovascular parameters such as arterial blood pressure is measured continuously through a catheter placed in the femoral artery. Cardiac output (CO) is measured and recorded every 15 minutes by thermo-dilution, and pulmonary artery pressure (PA, systolic and diastolic), central venous pressure (CVP), and $SvO_2$ is recorded every 15 min and pulmonary wedge pressure (PCWP) every 30 min from a Swan-Ganz catheter. Indirect calorimetry is performed e.g. by means of a Quark RMR ICU option (Cosmed, Rome, Italy) equipment. Blood gases and electrolytes are determined in both arterial and venous blood collected from the femoral artery and Swan-Ganz catheters and analysed with use of an ABL725 blood gas analyser (Radiometer Medical Aps, Brønshøj, Denmark). Analyses include pH, BE, Hemoglobin, $HCO_3$, $pO_2$, $pCO_2$, $K^+$, $Na^+$, Glucose and Lactate (FIG. 9).

Data Analysis

Statistical analysis was performed using Graph Pad PRISM software (GraphPad Software version 6.03, La Jolla, Calif., USA). All respiratory, lactate and pH data are expressed as mean±SEM. Ratios are plotted as individuals and means. One-way ANOVA was used for one-factor comparison of three or more groups (concentration of drugs) and two-way mixed model ANOVA was used for two-factor comparison (time and concentration of drugs/treatment) of three or more groups. Post-hoc tests to compensate for multiple comparisons were done according to Holm-Sidak. Correlations were expressed as $r^2$ and P-values. Standard non-linear curve fitting was applied to calculate half maximal inhibitory concentration ($IC_{50}$) values. Results were considered statistically significant for $P<0.05$.

Properties of Desired Compound in a Proof of Concept In Vivo Model of Metabolic Crisis The ideal compound should reduce the lactate accumulation and pH decrease in pigs with metabolic crisis induced by complex I inhibition. The energy expenditure decrease following complex I inhibition should be attenuated. The compound should not induce any overt negative effects as measured by blood and hemodynamic analyses.

Metabolomics Method

White blood cells or platelets are collected by standard methods and suspended in a MiR05, a buffer containing 110 mM sucrose, HEPES 20 mM, taurine 20 mM, K-lactobionate 60 mM, $MgCl_2$ 3 mM, $KH_2PO_4$ 10 mM, EGTA 0.5 mM, BSA 1 g/l, with or without 5 mM glucose, pH 7.1. The sample is incubated with stirring in a high-resolution oxygraph (Oxygraph-2k, Oroboros Instruments, Innsbruck, Austria) at a constant temperature of 37° C.

After 10 minutes rotenone in DMSO is added (2 µM) and incubation continued. Following a further 5 minutes test compound in DMSO is added, optionally with further test compound after and a further period of incubation. During the incubation $O_2$ consumption is measured in real-time.

At the end of the incubation the cells are collected by centrifugation and washed in 5% mannitol solution and extracted into methanol. An aqueous solution containing internal standard is added and the resultant solution treated by centrifugation in a suitable microfuge tube with a filter.

The resulting filtrate is dried under vacuum before CE-MS analysis to quantify various primary metabolites by the method of Ooga et al (2011) and Ohashi et al (2008).

In particular the levels of metabolite in the TCA cycle and glycolysis are assessed for the impact of compounds of the invention.

Ooga et al, Metabolomic anatomy of an animal model revealing homeostatic imbalances in dyslipidaemia, Molecular Biosystems, 2011, 7, 1217-1223

Ohashi et al, Molecular Biosystems, 2008, 4, 135-147

EXAMPLES

Metformin Studies

In the metformin study the following compounds were used (and which are referred to in the figures)

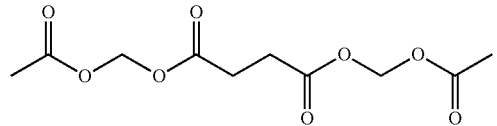 [SMILES: CC(=O)OCOC(=O)CCC(=O)OCOC(C)=O]
(NV118)

-continued

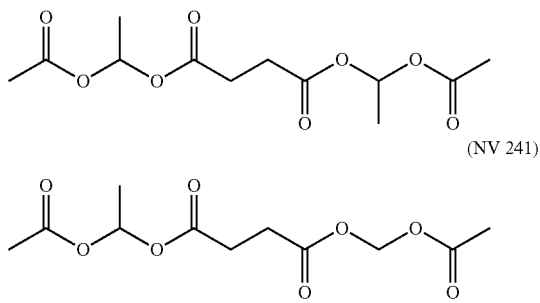

(NV 189)

(NV 241)

The compounds are prepared as described in WO 2014/053857.

Aim of Study Reported in Examples 1-2

Metformin Induces Lactate Production in Peripheral Blood Mononuclear Cells and Platelets through specific Mitochondrial Complex I Inhibition Metformin is a widely used anti-diabetic drug associated with the rare side-effect of lactic acidosis, which has been proposed to be linked to drug-induced mitochondrial dysfunction. Using respirometry, the aim of the study reported in Examples 1-2 was to evaluate mitochondrial toxicity of metformin to human blood cells in relation to that of phenformin, a biguanide analog withdrawn in most countries due to a high incidence of lactic acidosis.

Aim of the Study Reported in Example 3

The aim is to investigate the ability of succinate prodrugs to alleviate or circumvent undesired effects of metformin and phenformin.

Example 1A

Effects of Metformin and Phenformin on Mitochondrial Respiration in Permeabilized Human Platelets In order to investigate the specific target of biguanide toxicity, a protocol was applied using digitonin permeabilization of the blood cells and sequential additions of respiratory complex-specific substrates and inhibitors in MiR05 medium. After stabilization of routine respiration, i.e. respiration of the cells with their endogenous substrate supply and ATP demand, metformin, phenformin or their vehicle (double-deionized water) were added. A wide concentration range of the drugs was applied; 0.1, 0.5, 1, and 10 mM metformin and 25, 100 and 500 µM phenformin. After incubation with the drugs for 10 min at 37° C., the platelets were permeabilized with digitonin at a previously determined optimal digitonin concentration (1 µg $10^{-6}$ platelets) to induce maximal cell membrane permeabilization without disruption of the mitochondrial function and allowing measurements of maximal respiratory capacities (Sjövall et al. (2013a). For evaluation of complex 1-dependent oxidative phosphorylation capacity ($OXPHOS_{CI}$) first, the NADH-linked substrates pyruvate and malate (5 mM), then ADP (1 mM) and, at last, the additional complex I substrate glutamate (5 mM) were added sequentially. Subsequently the $FADH_2$-linked substrate succinate (10 mM) was given to determine convergent complex I- and II-dependent OXPHOS capacity ($OXPHOS_{CI+II}$). $LEAK_{I+II}$ state, a respiratory state where oxygen consumption is compensating for the back-flux of protons across the mitochondrial membrane (Gnaiger, 2008), was assessed by addition of the ATP-synthase inhibitor oligomycin (1 µg $mL^{-1}$). Maximal uncoupled respiratory electron transport system capacity supported by convergent input through complex I and II ($ETS_{CI+II}$) was evaluated by subsequent titration with the protonophore carbonylcyanide p-(trifluoromethoxy) phenylhydrazone (FCCP). Addition of the complex I inhibitor rotenone (2 µM) revealed complex II-dependent maximal uncoupled respiration ($ETS_{CII}$). The complex III inhibitor antimycin (1 µg $mL^{-1}$) was then given to reveal residual oxygen consumption (ROX). Finally, the artificial complex IV substrate N,N,N',N'-tetramethyl-p-phenylenediamine dihydrochloride (TMPD, 0.5 mM) was added and the complex IV inhibitor sodium azide (10 mM) was given to measure complex IV activity and chemical background, respectively. Complex IV activity was calculated by subtracting the sodium azide value from the TMPD value. With exception of complex IV activity, all respiratory states were measured at steady-state and corrected for ROX. Complex IV activity was measured after ROX determination and not at steady-state. The integrity of the outer mitochondrial membrane was examined by adding cytochrome c (8 µM) during $OXPHOS_{CI+II}$ in presence of vehicle, 100 mM metformin or 500 µM phenformin.

Example 1B

Effect of Metformin on Mitochondrial Respiration in Permeabilized Human Peripheral Blood Mononuclear Cells and on Mitochondrial Respiration in Intact Human Platelets For analysis of respiration of permeabilized PBMCs in response to metformin (0.1, 1 and 10 mM) the same protocol as for permeabilized platelets was used, except the digitonin concentration was adjusted to 6 µg $10^{-6}$ PBMCs (Sjövall et al., 2013b).

Results

Respiration using complex I substrates was dose-dependently inhibited by metformin in both permeabilized human PBMCs and platelets (FIG. 1). $OXPHOS_{CI}$ capacity decreased with increasing concentrations of metformin compared to controls with near complete inhibition at 10 mM (−81.47%, P<0.001 in PBMCs and −92.04%, P<0.001 in platelets), resulting in an $IC_{50}$ of 0.45 mM for PBMCs and 1.2 mM for platelets. Respiratory capacities using both complex I- and complex II-linked substrates, $OXPHOS_{CI+II}$ and $ETS_{CI+II}$, were decreased similarly to $OXPHOS_{CI}$ by metformin as illustrated by the representative traces of simultaneously measured $O_2$ consumption of vehicle-treated and 1 mM metformin-treated permeabilized PBMCs (FIG. 1a). In contrast, $ETS_{CII}$ capacity and complex IV activity did not change significantly in presence of metformin compared to controls in either cell type (FIG. 1b, c) and neither did $LEAK_{I+II}$ respiration (the respiratory state where oxygen consumption is compensating for the back-flux of protons across the mitochondrial membrane, traditionally denoted state 4 in isolated mitochondria, data not shown). The mitochondrial inhibition of complex I induced by metformin did not seem to be reversible upon extra- and intracellular removal of the drug by washing and permeabilizing the cells, respectively. Although the severity of the insult of complex I inhibition was attenuated by removal (probably attributed to a shorter exposure time of the drug) platelets did not regain routine and maximal mitochondrial function comparable to control (data not shown). Phenformin likewise inhibited $OXPHOS_{CI}$ (FIG. 2), $OXPHOS_{CI+II}$ and $ETS_{CI+II}$ but not $ETS_{CII}$ or respiration specific to complex IV (data not shown). Phenformin demonstrated a 20-fold more potent inhibition of $OXPHOS_{CI}$ in permeabilized platelets than metformin ($IC_{50}$ 0.058 mM and 1.2 mM, respectively) (FIG. 2). Metformin and phenformin did not induce increased respiration following administration of cytochrome c and hence did not disrupt the integrity of the outer mitochondrial membrane.

After stabilization of routine respiration in MiR05 medium, either vehicle (double-deionized water) or 1, 10 and 100 mM metformin was added. Routine respiration was followed for 60 min at 37° C. before the ATP-synthase inhibitor oligomycin (1 µg mL$^{-1}$) was added to assess LEAK respiration. Maximal uncoupled respiratory electron transport system capacity supported by endogenous substrates (ETS) was reached by titration of FCCP. Respiration was sequentially blocked by the complex I inhibitor rotenone (2 µM), the complex III inhibitor antimycin (1 µg mL$^{-1}$) and the complex IV inhibitor sodium azide (10 mM) to assess ROX, which all respiration values were corrected for. In an additional experiment, whole blood was incubated in $K_2$EDTA tubes with different metformin concentrations (0.1, 0.5 and 1 mM) over a period of 18 h prior to isolation of platelets and analyses of respiration.

Results

In intact human platelets, metformin decreased routine respiration in a dose- and time-dependent manner (FIG. 3a). When exposed to either metformin or vehicle the platelets showed a continuous decrease in routine respiration over time. After 60 min the routine respiration was reduced by −14.1% in control (P<0.05), by −17.27% at 1 mM (P<0.01), by −28.61% at 10 mM (P<0.001), and by −81.78% at 100 mM of metformin (P<0.001) compared to the first measurement after addition. Metformin at 100 mM decreased routine respiration significantly compared to control already after 15 min of exposure (−39.77%, P<0.01). The maximal uncoupled respiration of platelets (the protonophore-titrated ETS capacity) after 60 min incubation, was significantly inhibited by 10 mM (−23.86%, P<0.05) and 100 mM (−56.86%, P<0.001) metformin (FIG. 3b). LEAK respiration in intact cells was not significantly changed by metformin incubation (data not shown). When whole blood was incubated at a metformin concentrations of 1 mM over 18 h routine respiration of intact human platelets was reduced by 30.49% (P<0.05).

Example 2

Effect of Metformin and Phenformin on Lactate Production and pH of Intact Human Platelets Platelets were incubated for 8 h with either metformin (1 mM, 10 mM), phenformin (0.5 mM), rotenone (2 µM), or the vehicle for rotenone (DMSO). Lactate levels were determined every 2 h (n=5) using the Lactate Pro™ 2 blood lactate test meter (Arkray, Alere A B, Lidingö, Sweden) (Tanner et al., 2010). Incubation was performed at 37° C. at a stirrer speed of 750 rpm, and pH was measured at start, after 4 and after 8 h of incubation (n=4) using a PHM210 Standard pH Meter (Radiometer, Copenhagen, Denmark).

Results

Lactate production increased in a time- and dose-dependent manner in response to incubation with metformin and phenformin in human platelets (FIG. 4a). Compared to control, metformin-(1 and 10 mM), phenformin-(0.5 mM), and rotenone-(2 µM) treated platelets all produced significantly more lactate over 8 h of treatment. At 1 mM metformin, lactate increased from 0.30±0.1 to 3.34±0.2 over 8 h and at 10 mM metformin, lactate increased from 0.22±0.1 to 5.76±0.7 mM. The corresponding pH dropped from 7.4±0.01 in both groups to 7.16±0.03 and 7.00±0.04 for 1 mM and 10 mM metformin, respectively. Phenformin-treated platelets (0.5 mM) produced similar levels of lactate as 10 mM metformin-treated samples. The level of lactate increase correlated with the decrease in pH for all treatment groups. The increased lactate levels in metformin-treated intact platelets also correlated with decreased absolute $OXPHOS_{CI}$ respiratory values seen in metformin-treated permeabilized platelets ($r^2$=0.60, P<0.001). A limited set of experiments further demonstrated that intact PBMCs also show increased lactate release upon exposure to 10 mM metformin (data not shown).

Discussion of the Results from Examples 1-2

This study demonstrates a non-reversible toxic effect of metformin on mitochondria specific for complex I in human platelets and PBMCs at concentrations relevant for the clinical condition of metformin intoxication. In platelets, we further have shown a correlation between decreased Complex I respiration and increased production of lactate. The mitochondrial toxicity we observed for metformin developed over time in intact cells. Phenformin, a structurally related compound now withdrawn in most countries due to a high incidence of LA, induced lactate release and pH decline in platelets through a complex I specific effect at substantially lower concentration.

In the present study, using a model applying high-resolution respirometry to assess integrated mitochondrial function of human platelets, we have demonstrated that the mitochondrial toxicity of both metformin and phenformin is specific to respiratory complex I and that a similar specific inhibition also is present in PBMCs. Complex I respiration of permeabilized PBMCs was 2.6-fold more sensitive to metformin than that of permeabilized platelets. However, due to the time-dependent toxicity of metformin (see below), the $IC_{50}$ is possibly an underestimation and could be lower if determined after longer exposure time. These findings further strengthen that the mitochondrial toxicity of metformin is not limited to specific tissues, as shown previously by others, but rather a generalized effect on a subcellular level (Kane et al., 2010, Larsen et al., 2012, Owen et al., 2000, Dykens et al., 2008, Brunmair et al., 2004, Protti et al., 2012a). The metformin-induced complex IV inhibition in platelets reported by (Protti et al., 2012a, Froth et al., 2012b) has not been confirmed in this study or in an earlier study by Dykens et al. (2008) using isolated bovine mitochondria. Further, metformin and phenformin did not induce respiratory inhibition through any unspecific permeability changes of the inner or outer mitochondrial membranes as there were no evidence of uncoupling or stimulatory response following cytochrome c addition in presence of the drugs. High-resolution respirometry is a method of high sensitivity and allows $O_2$ measurements in the picomolar range. When applied to human blood cells ex vivo, it allows assessment of respiration in the fully-integrated state in intact cells, and permits exogenous supply and control of substrates to intact mitochondria in permeabilized cells. This is in contrast to enzymatic spectrophotometric assays which predominantly have been used in the research on mitochondrial toxicity of metformin, for instance by Dykens et al. (2008) and Owen et al. (2000). These assays measure the independent, not-integrated function of the single complexes and hence, are less physiological, which may contribute to the differences in results between our studies.

The results of the study demonstrated significant respiratory inhibition, lactate increase and pH decrease in intact platelet suspensions caused by metformin at concentrations relevant for intoxication already after 8-18 h. The time-dependent inhibition of mitochondrial respiration in combination with the lack of reversal following exchange of the extracellular buffer and dilution of intracellular content of soluble metformin by permeabilization of the cell point towards intramitochondrial accumulation being a key factor in the development of drug-induced mitochondrial dysfunction-related LA, as has been proposed by others (Chan et al., 2005, Lalau, 2010).

Phenformin's mitochondrial toxicity has been shown previously, for instance on HepG2 cells, a liver carcinoma cell line, and isolated mitochondria of rat and cow (Dykens et al., 2008). Here we have demonstrated specific mitochondrial toxicity also using human blood cells. Compared to metformin, phenformin had a stronger mitochondrial toxic potency on human platelets ($IC_{50}$ 1.2 mM and 0.058 mM, respectively). Phenformin and metformin show a 10 to 15-fold difference in clinical dosing (Scheen, 1996, Davidson and Peters, 1997, Kwong and Brubacher, 1998, Sogame et al., 2009) and 3 to 10-fold difference in therapeutic plasma concentration (Regenthal et al., 1999, Schulz and Schmoldt, 2003). In this study we have observed a 20-fold difference between phenformin and metformin in the potential to inhibit complex I. If translated to patients this difference in mitochondrial toxicity in relation to clinical dosing could potentially explain phenformin's documented higher incidence of phenformin-associated LA.

Standard therapeutic plasma concentrations of metformin are in the range of 0.6 and 6.0 µM and toxic concentrations lie between 60 µM and 1 mM (Schulz and Schmoldt, 2003, Protti et al., 2012b). In a case report of involuntary metformin intoxication, prior to hemodialysis, a serum level of metformin over 2 mM was reported (Al-Abri et al., 2013). Tissue distribution studies have further demonstrated that the metformin concentration under steady-state is lower in plasma/serum than in other organs. It has been shown to accumulate in 7 to 10-fold higher concentrations in the gastrointestinal tract, with lesser but still significantly higher amounts in the kidney, liver, salivary glands, lung, spleen and muscle as compared to plasma levels (Graham et al., 2011, Bailey, 1992, Scheen, 1996). Under circumstances where the clearance of metformin is impaired, such as predisposing conditions affecting the cardiovascular system, liver or kidneys, toxic levels can eventually be reached. The toxic concentration of metformin seen in the present study (1 mM) is thus comparable to what is found in the blood of metformin-intoxicated patients. Although metformin is toxic to blood cells, as shown in this study, it is unlikely that platelets and PBMCs are major contributors to the development of LA. As metformin is accumulated in other organs and additionally these organs are more metabolically active, increased lactate production is likely to be seen first in other tissues. Our results therefore strengthen what has been suggested by others (Brunmair et al., 2004, Protti et al., 2012b, Dykens et al., 2008), that systemic mitochondrial inhibition is the cause of metformin-induced LA.

Based on earlier studies and the present findings it is intriguing to speculate on the possibility that metformin's anti-diabetic effect may be related to inhibition of aerobic respiration. The decreased glucose levels in the liver and decreased uptake of glucose to the blood in the small intestine in metformin-treated diabetic patients (Kirpichnikov et al., 2002) might be due to partial complex I inhibition. Complex I inhibition causes reduced production of ATP, increased amounts of AMP, activation of the enzyme AMP-activated protein kinase (AMPK), and accelerated glucose turnover by increased glycolysis, trying to compensate for the reduced ATP production (Brunmair et al., 2004, Owen et al., 2000).

Until now, treatment measures for metformin-associated LA consist of haemodialysis and haemofiltration to remove the toxin, correct for the acidosis and increase renal blood flow (Lalau, 2010).

Example 3

Intervention on Metformin-Induced Increase in Lactate Production with Cell-Permeable Succinate Prodrugs Intervention of metformin-induced increase in lactate production in intact human platelets with newly developed and synthesized cell-permeable succinate prodrugs was done in PBS containing 10 mM glucose. The platelets were exposed to either rotenone alone (2 µM), rotenone (2 µM) and antimycin (1 µg/mL, only for cells treated with NV 189), or 10 mM metformin and after 60 min either vehicle (dmso, control), either of the cell-permeable succinate prodrugs (NV118, NV189 and NV241), or succinate were added at a concentration of 250 µM each 30 minutes. Lactate levels were measured in intervals of 30 min with the onset of the experiment. Additionally, pH was measured prior to the first addition of vehicle (dmso, control), the different cell-permeable succinate prodrugs (NV 118, NV 189, NV 241) or succinate and at the end of the experiment. The rate of lactate production was calculated with a nonlinear fit with a 95% Confidence interval (CI) of the lactate-time curve slope (FIGS. 5, 6, 7 and 8)

Results relating to Example 3 are based on the assays described herein

Lactate Production Due to Rotenone and Metformin Incubation in Thrombocytes is Attenuated by the Addition of Cell-Permeable Succinate Prodrugs The rate of lactate production in thrombocytes incubated with 2 µM Rotenone was 0.86 mmol lactate $(200 \cdot 10^6 trc \cdot h)^{-1}$ (95% Confidence Intervall [CI] 0.76-0.96) which was attenuated by NV118 (0.25 mmol [95% CI 0.18-0.33]), NV189 (0.42 mmol [95% CI 0.34-0.51]) and NV241 (0.34 mmol [95% CI 0.17-0.52]), which was not significantly different from cells not receiving rotenone (0.35 [95% CI 0.14-0.55]) (FIGS. 5, 6 and 7). Cells incubated with antimycin in addition to rotenone and NV189 had a lactate production comparable to rotenone-treated cell (0.89 mmol [0.81-0.97]), demonstrating the specific mitochondrial effect of the cell-permeable succinate prodrugs (FIG. 6).

Cells incubated with 10 mM Metformin produce lactate at a rate of 0.86 mmol lactate $(200 \cdot 10^9 trc \cdot h)^{-1}$ (95% CI 0.69-1.04) compared 0.22 mmol (95% CI 0.14-0.30) in vehicle (water) treated cells (FIG. 8). Co-incubating with either of the three succinate prodrugs attenuate the metformin effect resulting in 0.43 mmol production (95% CI 0.33-0.54) for NV118 (FIG. 5), 0.55 mmol (95% CI 0.44-0.65) for NV189 (FIG. 6), and 0.43 mmol (95% CI 0.31-0-54) for NV241 (FIG. 7).

Example 4

Results of Biological Experiments

The compounds given in the following table were subject to the assays (1)-(4) mentioned under the heading I. Assay for evaluating enhancement and inhibition of mitochondrial energy producing function in intact cells. In the following table the results are shown, which indicate that all compounds tested have suitable properties. Importantly, all compounds show specific effect on CII-linked respiration as seen from screening protocols 1 and 4, as well as a convergent effect, with CI-substrates available, as seen in assay 2.

Results from screening protocols 1-4

| Compound NV | Convergent (Routine) | Convergent (FCCP) | CII (plasma) | CII | Uncoupling | Toxicity |
|---|---|---|---|---|---|---|
| 01-193 | (++) | + | (+) | + | + | 5 mM |
| 01-188 | +++ | +++ | + | + | (+) | 5 mM |
| 01-185 | (+) | + | + | + | (+) | 2 mM |
| 01-205 | +++ | ++ | + | ++ | (+) | 5 mM |
| 01-114 | +++ | ++ | + | ++ | (+) | 10 mM |
| 01-041 | + | +++ | + | ++ | (+) | 5 mM |
| 01-108 | ++ | ++ | (+) | (++) | + | 10 mM |
| 01-150 | +++ | + | (+) | ++ | (+) | 2 mM |
| 01-134 | ++ | (+) | (+) | (+) | (+) | 10 mM |

Legend: Convergent (Routine)—the increase in mitochondrial oxygen consumption induced by the compound under conditions described in screening assay 3; Convergent (FCCP)—the increase in mitochondrial oxygen consumption induced by the compound under conditions described in screening assay 2 (uncoupled conditions); Convergent (plasma)—the increase in mitochondrial oxygen consumption induced by the compound in cells with inhibited complex I incubated in human plasma, as described in screening assay 4; CII—the increase in mitochondrial oxygen consumption induced by the compound in cells with inhibited complex I as described in screening assay 1; Uncoupling—the level of oxygen consumption after addition of oligomycin as described in screening assay 3. The response in each parameter is graded either +, ++ or +++ in increasing order of potency. Brackets [( )] indicate an intermediate effect, i.e. (+++) is between ++ and +++. Toxicity—the lowest concentration during compound titration at which a decrease in oxygen consumption is seen as described in screening assay 2.

Preparation of Succinate Prodrug/Protected Succinates

The skilled person will recognise that the protected succinates of the invention may be prepared, in known manner, in a variety of ways. The routes below are merely illustrative of some methods that can be employed for the synthesis of compounds of formula (I).

The present invention further provides a process for the preparation of a compound of formula (I) which comprises reacting succinic acid with compound of formula (VI)

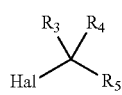

wherein Hal represents a halogen (e.g. F, Cl, Br or I) and $R_3$, $R_4$ and $R_5$ are as defined in formula (I).

The reaction of succinic acid and the compound for formula (VI) may conveniently be carried out in a solvent such as dichloromethane, acetone, acetonitrile or N,N-dimethylformamide with a suitable base such as triethylamine, diisopropylethylamine or caesium carbonate at a temperature, for example, in the range from −10° C. to 80° C., particularly at room temperature. The reaction may be performed with optional additives such as sodium iodide or tetraalkyl ammonium halides (e.g. tetrabutyl ammonium iodide).

For compounds of formula (I) wherein $R_1$ and $R_2$ are different groups of formula (II), the compound of formula (I) may be prepared by reacting a group of formula (VII)

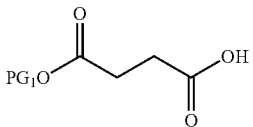

wherein $PG_1$ is a protecting group such as tert-butyl, benzyl or 4-methoxybenzyl, with a group of formula (VI) under the conditions outlined above followed by deprotection of the protecting group under appropriate conditions such as trifluoroacetic acid or hydrochloric acid in a solvent such as dichloromethane or by hydrogenation (aryl groups), followed by reaction of the resulting compound with a different group of formula (VI) under the conditions outlined above to react with the deprotected carboxylate. For compounds of formula (I) wherein $R_1$ is an optionally substituted alkyl group and $R_2$ is a group of formula (II), the compound of formula (I) may be prepared by reacting a group of formula (VIII)

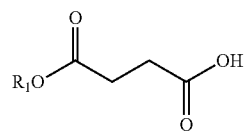

with a group of formula (VI) under the conditions outlined above.

Protected di-succinate compounds may conveniently be prepared by reaction of a group of formula (IX)

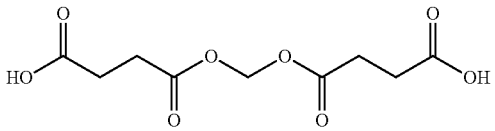

with a group of formula (VI) under the conditions outlined above. Compounds of formula (IX) may be conveniently prepared by reaction of a compound of formula (VII) with dichloromethane in a suitable solvent such as dichloromethane with a suitable additive such as tetrabutylhydrogensulfate. The resulting bis-ester may be subsequently hydrolysed by treatment with an acid such as trifluoroacetic acid or hydrochloric acid in a solvent such as dichloromethane to afford compounds of formula (IX).

Compounds of formula (VII) and (VIII) are either commercially available or may be conveniently prepared by literature methods such as those outlined in Journal of Organic Chemistry, 72(19), 7253-7259; 2007.

Compounds of formula (VI)

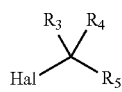

are either commercially available or may be conveniently prepared by literature methods such as those outlined in Journal of the American Chemical Society, 43, 660-7; 1921 or Journal of medicinal chemistry (1992), 35(4), 687-94.

Preparatory Examples

To illustrate methods for preparing protected succinates the following preparatory examples are given in which, unless stated otherwise:

(i) when given, $^1$H NMR spectra were recorded on Bruker Avance 300 (300 MHz) or Bruker Avance 400 (400 MHz). Either the central peaks of the chloroform-d (CDCl$_3$; $\delta_H$ 7.27 ppm), dimethylsulfoxide-d$_6$ (d$_6$-DMSO; $\delta_H$ 2.50 Ppm) or methanol-d$_4$ (CD$_3$OD; $\delta_H$ 3.31 ppm), or an internal standard of tetramethylsilane (TMS; $\delta_H$ 0.00 ppm) were used as references;

(ii) Mass spectra were recorded on an Agilent MSD (+ve and −ve electrospray) or a Fisons Instrument VG Platform following analytical HPLC. Where values for m/z are given, generally only ions which indicate the parent mass are reported, and the mass ions quoted are the positive and negative mass ions: [M+H]$^+$ or [M−H]$^-$;

(iii) The title and subtitle compounds of the examples and preparations were named using AutoNom.

(iv) Unless stated otherwise, starting materials were commercially available. All solvents and commercial reagents were of laboratory grade and were used as received. All operations were carried out at ambient temperature, i.e. in the range 16 to 28° C. and, where appropriate, under an atmosphere of an inert gas such as nitrogen;

(v) The following abbreviations are used:

| | |
|---|---|
| DCM | Dichloromethane |
| DMF | Dimethylformamide |
| DMSO | Dimethyl sulfoxide |
| HPLC | High Performance Liquid Chromatography |
| g | Gram(s) |
| h | Hour(s) |
| LCMS | Liquid Chromatography-Mass Spectroscopy |
| MPLC | Medium Pressure Liquid Chromatography |
| mmol | millimole |

Example 1: Succinic acid bis-(2,2-dimethyl-propionyloxymethyl) ester

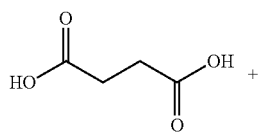

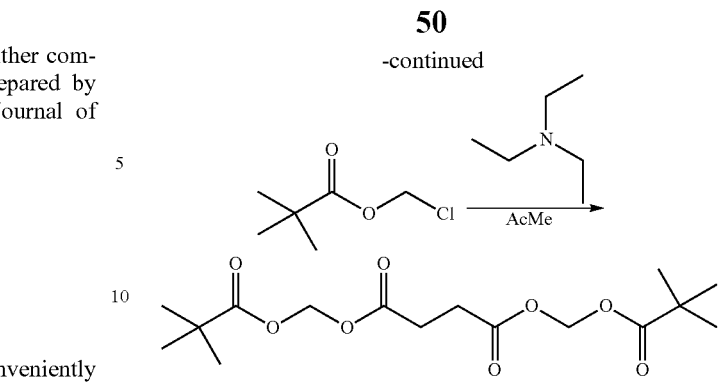

Succinic acid (1.2 g, 10 mmol) and chloromethyl pivalate (5.8 mL, 40 mmol) were added to acetone (4 mL) and the mixture cooled in ice. Triethylamine (3.3 mL, 24 mmol) was added portion-wise and the solution stirred overnight at room temperature.

The mixture was concentrated and partitioned between water and ethyl acetate. The ethyl acetate solution was washed with water then sodium bicarbonate solution. It was treated with decolourising charcoal, dried over potassium carbonate and concentrated to an oil.

Purification by MPLC chromatography (basic alumina, 10% ethyl acetate/90% cyclohexane) afforded 0.18 g succinic acid bis-(2,2-dimethyl-propionyloxymethyl) ester as an oil.

$^1$H NMR (CDCl$_3$, ppm) δ 1.23 (s, 18H), 2.71 (s, 4H), 5.77 (s, 4H).

Example 2: Succinic Acid 2,2-dimethyl-propionyloxymethyl ester methyl ester

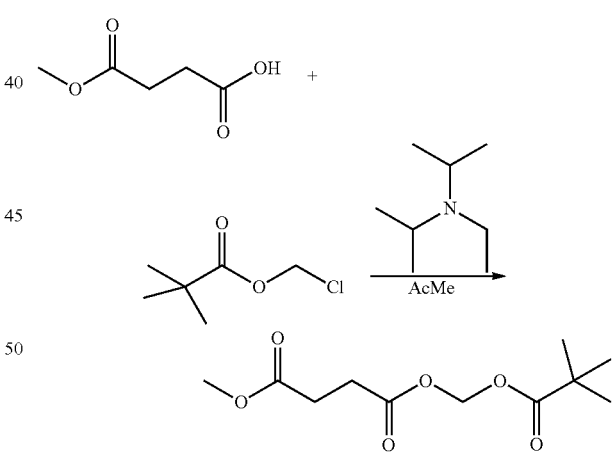

Methyl succinate (1.3 g, 10 mmol) and chloromethyl pivalate (2.9 mL, 20 mmol) were added to acetone (2 mL) and the mixture cooled in ice. Triethylamine (2.0 mL, 14 mmol) was added portion-wise and the solution stirred overnight at room temperature. The mixture was concentrated and partitioned between water and ethyl acetate. The ethyl acetate solution was washed with water then sodium bicarbonate solution, dried over potassium carbonate and concentrated to give 2.4 g succinic acid 2,2-dimethyl-propionyloxymethyl ester methyl ester as an oil.

$^1$H NMR (CDCl$_3$, ppm) δ 1.23 (s, 9H), 2.68 (m, 4H), 3.71 (s, 3H), 5.78 (s, 2H).

Example 3: Succinic acid diacetoxymethyl ester

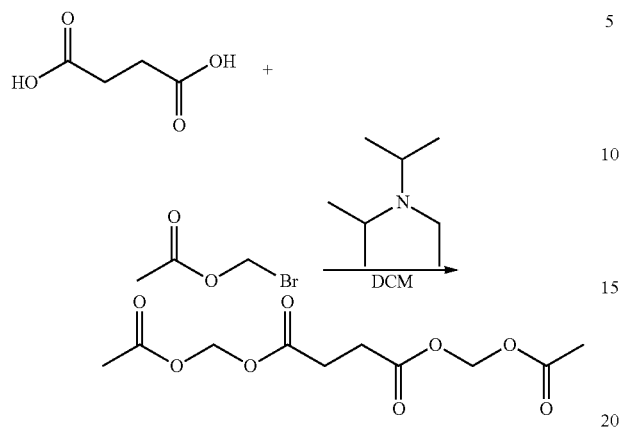

Succinic acid (58.6 g, 0.496 mol) was added to dichloromethane (2 L) and the mixture cooled to 0° C. Diisopropylethylamine (201 mL, 1.154 mol) was added during 20 minutes followed by bromomethyl acetate (159.4 g, 1.042 mol) during 30 minutes and the solution stirred overnight under an atmosphere of nitrogen.

The solution was cooled to 0° C. and washed successively with 1 L of cold 1% hydrochloric acid, 0.6% hydrochloric acid and water (×3). The solution was treated with decolourizing charcoal, dried with magnesium sulphate and concentrated to an oil which was crystallized from diethyl ether (200 mL)/isohexane (10 mL) to afford 92 g of succinic acid diacetoxymethyl ester as a white solid.

$^1$H NMR (CDCl$_3$, ppm) δ 2.13 (s, 6H), 2.72 (s, 4H), 5.76 (s, 4H).

A further 8 g of pure material was obtained from concentration of the liquors.

Example 4: Succinic acid acetoxymethyl ester methyl ester

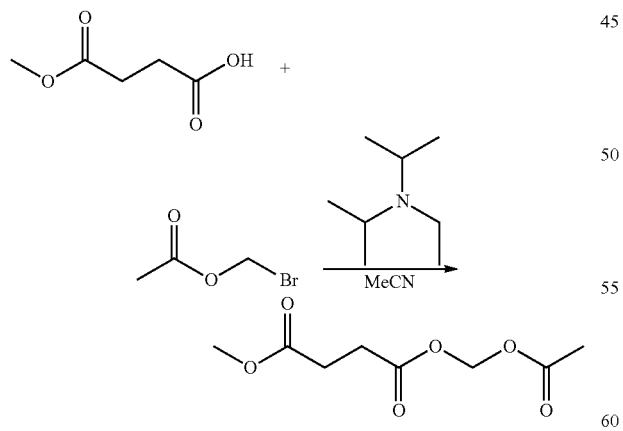

Methyl succinate (2.0 g, 15.1 mmol) was dissolved in acetonitrile (200 mL) and bromomethyl acetate (1.65 mL, 16.8 mmol) was added. The solution was cooled in cold water and diisopropylethylamine (3.16 mL, 18.2 mmol) was added. The solution was allowed to warm and stirred at room temperature for 70 minutes.

The solution was poured into ice/water (400 mL) and extracted with ethyl acetate. This ethyl acetate solution was washed with water, 1% hydrochloric acid, sodium bicarbonate solution and brine. It was dried with magnesium sulphate and concentrated to an oil.

Purification by MPLC (SiO$_2$, isohexane→20% ethyl acetate/80% isohexane) gave 0.91 g succinic acid acetoxymethyl ester methyl ester.

$^1$H NMR (CDCl$_3$, ppm) δ 2.13 (s, 3H), 2.69 (m, 4H), 3.71 (s, 3H), 5.77 (s, 2H).

Example 5: Succinic acid bis-(1-acetoxy-ethyl) ester

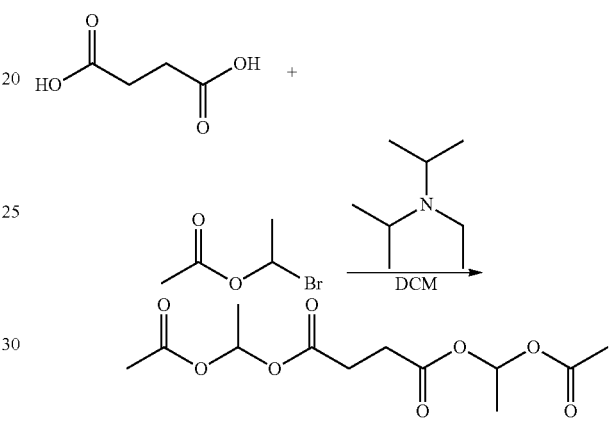

Succinic acid (58.6 g, 0.496 mol) was added to dichloromethane (2 L) and the mixture cooled to 0° C. Diisopropylethylamine (201 mL, 1.154 mol) was added during 20 minutes followed by 1-bromoethyl acetate (159.4 g, 1.042 mol) during 30 minutes and the solution stirred overnight under an atmosphere of nitrogen.

The solution was cooled to 0° C. and washed successively with cold (1.5 L quantities) of water, 1% hydrochloric acid (twice), sodium bicarbonate solution and water. The solution was dried with magnesium sulphate and concentrated to an oil which was crystallized from t-butylmethyl ether to afford 41 g of succinic acid diacetoxymethyl ester as a white solid.

$^1$H NMR (CDCl$_3$, ppm) δ 1.48 (d, J=5.4 Hz, 6H), 2.07 (s, 6H), 2.66 (m, 4H), 6.87 (q, J=5.5 Hz, 1H).

Example 6: Succinic acid 1-acetoxy-ethyl ester methyl ester

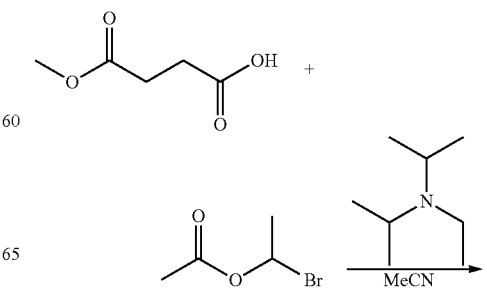

-continued

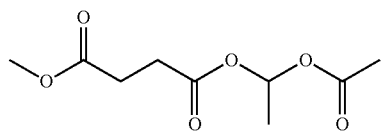

Methyl succinate (2.46 g, 18.6 mmol) was dissolved in acetonitrile (350 mL) and the solution cooled to −5° C. 1-Bromoethyl acetate (3.3 g, 19.8 mmol) and then diisopropylethylamine (4.0 mL, 23.3 mmol) were added. The solution was allowed to warm and stirred at room temperature for 3 days.

The solution was cooled and partitioned between cold water and ethyl acetate. This ethyl acetate solution was washed with 1% hydrochloric acid, sodium bicarbonate solution then twice with water. The solution was dried with magnesium sulphate and concentrated to an oil.

Purification by MPLC (SiO$_2$, isohexane→10% ethyl acetate/90% isohexane) gave 1.9 g succinic acid 1-acetoxyethyl ester methyl ester as an oil.

$^1$H NMR (CDCl$_3$, ppm) δ 1.48 (d, J=5.3 Hz, 3H), 2.07 (s, 3H), 2.65 (m, 4H), 3.70 (s, 3H), 6.86 (q, J=5.3 Hz, 1H).

Example 7: Succinic acid bis-(1-acetoxy-propyl) ester

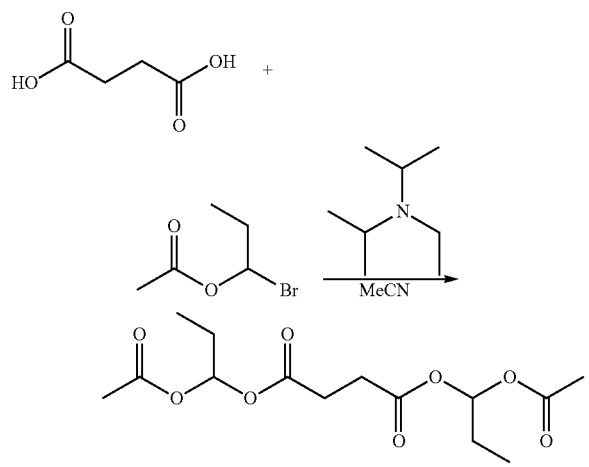

Succinic acid (2.0 g, 16.9 mmol) was dissolved in acetonitrile (350 mL) and the solution cooled to −5° C. 1-Bromopropyl acetate (6.7 g, 37.0 mmol) and then diisopropylethylamine (7.3 mL, 41.9 mmol) were added. The solution was stirred at room temperature for 3 days.

The solution was cooled and partitioned between cold water and ethyl acetate. This ethyl acetate solution was washed with cold 1% hydrochloric acid, sodium bicarbonate solution then water. It was dried with magnesium sulphate and concentrated to an oil. Purification by MPLC (SiO$_2$, isohexane→10% ethyl acetate/90% isohexane) gave 0.85 g succinic acid bis-(1-acetoxy-propyl) ester as an oil.

$^1$H NMR (CDCl$_3$, ppm) δ 0.97 (t, J=7.6 Hz, 6H), 1.81 (m, 4H), 2.09 (s, 6H), 2.68 (m, 4H), 6.77 (t, J=5.6 Hz, 2H).

Example 8: Succinic acid bis-(1-propionyloxy-ethyl) ester

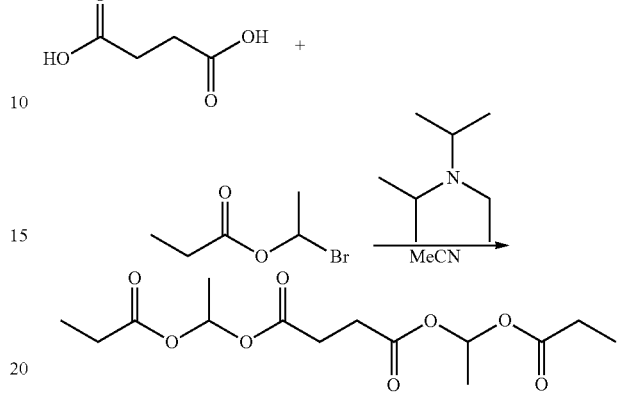

Succinic acid (2.0 g, 37.0 mmol) was dissolved in acetonitrile (350 mL) and the solution cooled to −5° C. 1-Bromoethyl propionate (6.7 g, 37.0 mmol) and then diisopropylethylamine (7.3 mL, 41.9 mmol) were added. The solution was allowed to warm and stirred at room temperature overnight.

The solution was cooled and partitioned between cold water and ethyl acetate. This ethyl acetate solution was washed with cold 1% hydrochloric acid, sodium bicarbonate solution and then twice with water. It was dried with magnesium sulphate and concentrated to an oil.

Purification by MPLC (SiO$_2$, isohexane→10% ethyl acetate/90% isohexane) gave 3.1 g succinic acid bis-(1-propionyloxy-ethyl) ester as an oil.

$^1$H NMR (CDCl$_3$, ppm) δ 1.15 (t, J=7.5 Hz, 6H), 1.49 (d, J=5.4 Hz, 6H), 2.36 (q, J=7.6 Hz, 4H), 2.66 (m, 4H), 6.90 (t, J=5.4 Hz, 2H).

Example 9: 1,3,5,7-Tetraoxa-cycloundecane-8,11-dione

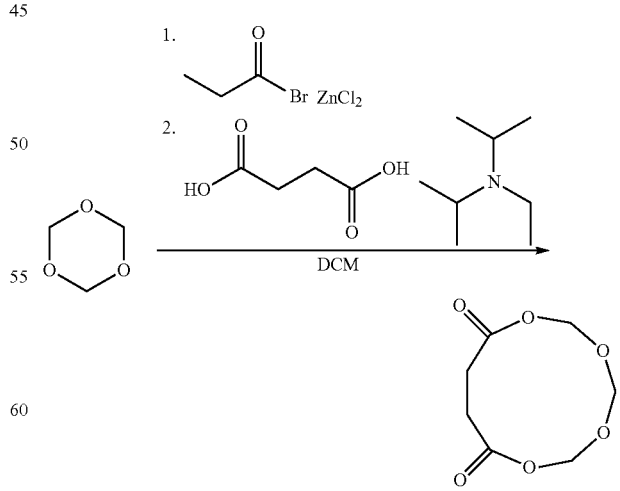

Propionyl bromide (8 mL, 89 mmol) was dissolved in dichloromethane (20 mL) and the solution cooled to −5° C. Zinc chloride (35 mg, 0.26 mmol) was added followed by trioxane (2.67 g, 29.7 mmol) portion wise during 30 minutes. The solution was stirred at 0° C. for 1 hour then at room temperature for a further hour. The solution was washed three times with cold water, dried with magnesium sulphate and concentrated to an oil. The crude product from this reaction (7.0 g) was added to a mixture of succinic acid (2.34 g, 19.8 mmol) and diisopropylethylamine (8.3 mL, 43.7 mmol) in dichloromethane (350 mL) cooled to −5° C. The solution was stirred at room temperature overnight then washed with cold 1% hydrochloric acid, sodium bicarbonate solution then three times with water. It was dried with magnesium sulphate and concentrated to an oil. Trituration with diethyl ether afforded 0.24 g 1,3,5,7-tetraoxa-cycloundecane-8,11-dione as a white solid.

$^1$H NMR (CDCl$_3$, ppm) δ 2.66 (s, 4H), 5.00 (s, 2H), 5.43 (s, 4H).

Example 10: Succinic acid acetoxymethyl ester diethylcarbamoylmethyl ester i) 2-Chloro-N,N-diethyl-acetamide

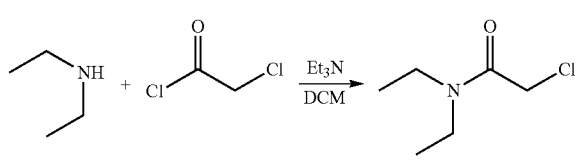

Diethylamine (10.0 mL, 97 mmol) and triethylamine (13.5 mL, 97 mmol) were diluted in dichloromethane (30 mL), the solution was cooled to 0° C. and chloroacetyl chloride (7.7 mL, 97 mmol) in DCM (10 ml) was added during 10 minutes, and the solution allowed to warm to room temperature and stirred overnight under an atmosphere of nitrogen. The solution was washed with water (2×10 mL). The organics were combined and the volatiles were removed in vacuo. The residue was purified by silica gel chromatography with a continuous gradient of iso-hexane/ethyl acetate 1:0 to 1:1 to afford the title compound (12.3 g) as a clear oil.

$^1$H NMR (300 MHz, CDCl$_3$) δ 1.11 (t, J=7.1 Hz, 3H), 1.21 (t, J=7.1 Hz, 3H), 3.35 (quint, J=6.9 Hz, 4H), 4.03 (s, 2H).

LCMS (m/z) 150.1-152.1 [M+H]$^+$.

ii) Succinic acid tert-butyl ester diethylcarbamoylmethyl ester

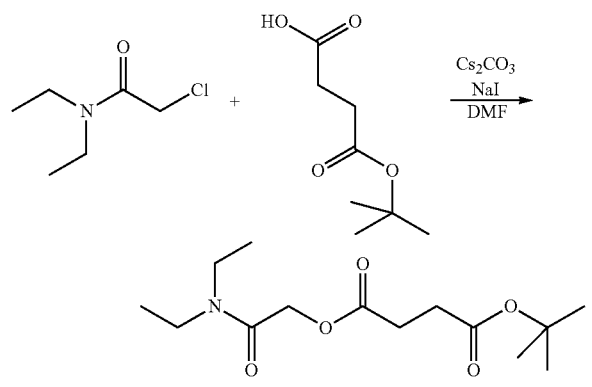

2-Chloro-N,N-diethyl-acetamide (Example 10, step (i), 1.71 g, 11.48 mmol), Succinic acid mono-tert-butyl ester (2.00 g, 11.48 mmol), caesium carbonate (2.67 g, 13.78 mmol), and sodium iodide (171 mg, 1.14 mmol), were suspended in DMF (20 mL) and the suspension stirred at 80° C. for 3 hours under an atmosphere of nitrogen. The suspension was cooled down to room temperature, diluted with ethyl acetate (40 mL) and washed with water (3×10 mL). The organics were combined and the volatiles were removed in vacuo. The residue was purified by silica gel chromatography with a continuous gradient of iso-hexane/ethyl acetate 1:0 to 0:1 to afford the title compound (3.29 g) as a clear oil.

$^1$H NMR (300 MHz, CDCl$_3$) δ 1.13 (t, J=7.1 Hz, 3H), 1.22 (t, J=7.1 Hz, 3H), 1.44 (s, 9H), 2.55-2.77 (m, 4H), 3.24 (q, J=7.1 Hz, 2H), 3.38 (q, J=7.1 Hz, 2H), 4.73 (s, 2H).

LCMS (m/z) 288.1 [M+H], Tr=2.07 min.

iii) Succinic acid monodiethylcarbamoylmethyl ester

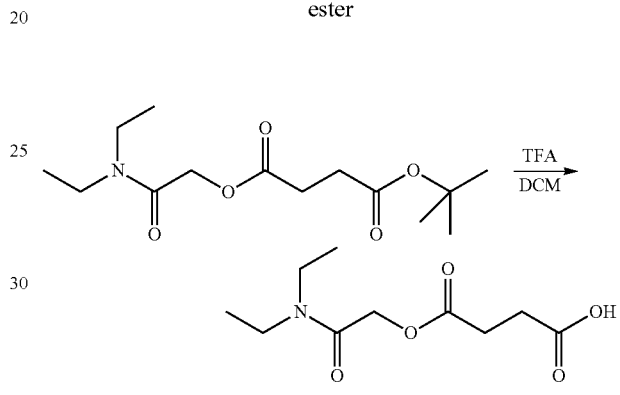

Succinic acid tert-butyl ester diethylcarbamoylmethyl ester (Example 10, step (ii), 3.29 g, 11.48 mmol) was dissolved in DCM (15 mL), the solution was cooled to 0° C. and trifluoroacetic acid (5 mL) was added. The solution was allowed to warm to room temperature and stirred overnight under an atmosphere of nitrogen. The volatiles were removed in vacuo the residue azeotroped with toluene (3×20 mL) to afford the title compound (3.19 g) as a clear oil.

$^1$H NMR (300 MHz, CDCl$_3$) δ 1.16 (t, J=7.1 Hz, 3H), 1.26 (t, J=7.1 Hz, 3H), 2.65-2.85 (m, 4H), 3.30 (q, J=7.1 Hz, 2H), 3.42 (q, J=7.1 Hz, 2H), 4.79 (s, 2H), 10.43 (br, 1H).

LCMS (m/z) 232.1 [M+H]$^+$, 230.1 [M−H]$^−$.

Example 10: Succinic acid acetoxymethyl ester diethylcarbamoylmethyl ester

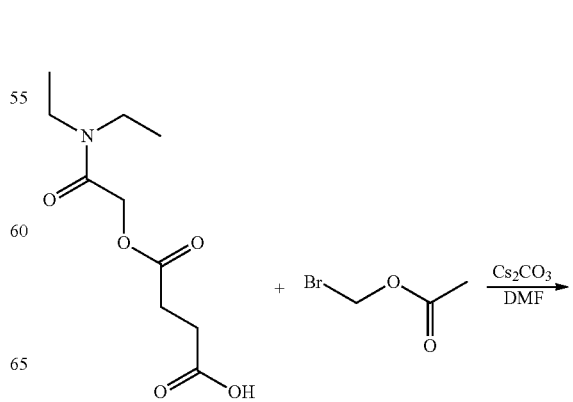

-continued

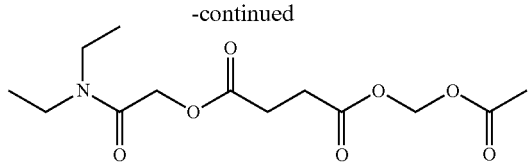

Succinic acid monodiethylcarbamoylmethyl ester (Example 10, step (iii), 850 mg, 3.68 mmol), acetic acid bromomethyl ester (671 mg, 4.42 mmol), caesium carbonate (1.78 g, 9.20 mmol), were suspended in DMF (10 mL) and the suspension stirred at 80° C. for 2 hours under an atmosphere of nitrogen. The suspension was cooled down to room temperature, diluted with ethyl acetate (30 mL) and washed with water (3×5 mL). The organics were combined and the volatiles were removed in vacuo. The residue was purified by silica gel chromatography with a continuous gradient of iso-hexane/ethyl acetate 1:0 to 0:1 to afford the title compound (334 mg) as a white solid.

$^1$H NMR (300 MHz, CDCl$_3$) δ 1.14 (t, J=7.1 Hz, 3H), 1.23 (t, J=7.1 Hz, 3H), 2.12 (s, 3H), 2.67-2.87 (m, 4H), 3.25 (q, J=7.1 Hz, 2H), 3.39 (q, J=7.1 Hz, 2H), 4.75 (s, 2H), 5.76 (s, 2H).

LCMS (m/z) 304.0 [M+H]$^+$.

Example 11: Succinic acid diethylcarbamoylmethyl ester 1-ethoxycarbonyloxy-ethyl ester

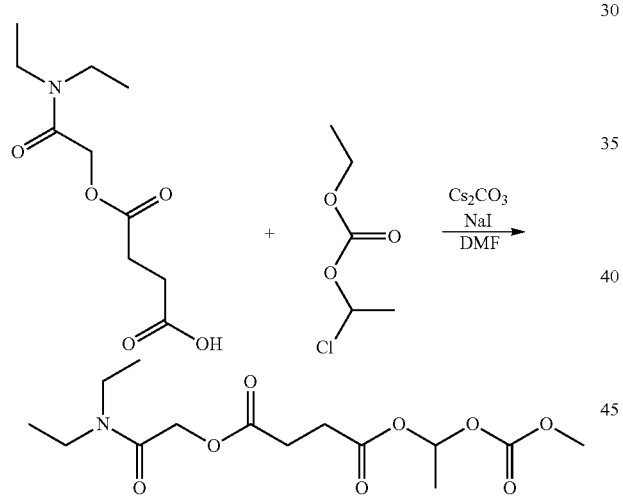

Succinic acid monodiethylcarbamoylmethyl ester (500 mg, 2.16 mmol), carbonic acid 1-chloro-ethyl ester ethyl ester (395 mg, 2.60 mmol), caesium carbonate (625 mg, 3.24 mmol), sodium iodide (32 mg, 0.21 mmol) were suspended In DMF (10 mL) and the suspension stirred at 80° C. for 3 hours under an atmosphere of nitrogen. The suspension was cooled down to room temperature, diluted with ethyl acetate (30 mL) and washed with water (3×5 mL). The organics were combined and the volatiles were removed in vacuo. The residue was purified by silica gel chromatography with a continuous gradient of iso-hexane/ethyl acetate 1:0 to 0:1 to afford the title compound (585 mg) as a clear oil.

$^1$H NMR (300 MHz, CDCl$_3$) δ 1.14 (t, J=7.1 Hz, 3H), 1.23 (t, J=7.1 Hz, 3H), 1.32 (t, J=7.1 Hz, 3H), 1.53 (d, J=5.5 Hz 3H), 2.67-2.87 (m, 4H), 3.25 (q, J=7.1 Hz, 2H), 3.39 (q, J=7.1 Hz, 2H), 4.22 (q, J=7.1 Hz, 2H), 4.74 (d, J=8.03 Hz, 2H), 6.77 (q, J=5.5 Hz, 1H).

LCMS (m/z) 348.0 [M+H]$^+$.

Example 12: Succinic acid 1-acetoxy-ethyl ester diethylcarbamoylmethyl ester

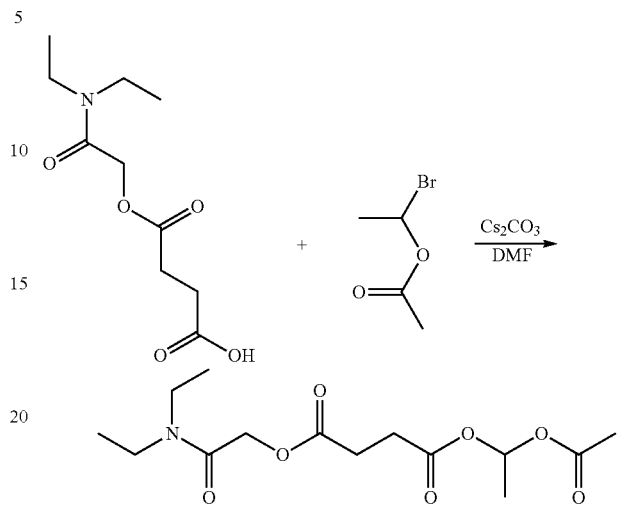

Succinic acid monodiethylcarbamoylmethyl ester (500 mg, 2.16 mmol), acetic acid 1-bromo-ethyl ester (434 mg, 2.60 mmol), caesium carbonate (625 mg, 3.24 mmol) were suspended in DMF (10 mL) and the suspension stirred at 70° C. for 2 hours under an atmosphere of nitrogen. The suspension was cooled down to room temperature, diluted with ethyl acetate (30 mL) and washed with water (3×5 mL). The organics were combined and the volatiles were removed in vacuo. The residue was purified by silica gel chromatography with a continuous gradient of iso-hexane/ethyl acetate 1:0 to 0:1 to afford the title compound (352 mg) as a clear oil.

$^1$H NMR (300 MHz, CDCl$_3$) δ 1.14 (t, J=7.1 Hz, 3H), 1.23 (t, J=7.1 Hz, 3H), 1.48 (d, J=5.5 Hz, 3H), 2.07 (s, 3H), 2.66-2.85 (m, 4H), 3.25 (q, J=7.1 Hz, 2H), 3.39 (q, J=7.1 Hz, 2H), 4.74 (d, J=5.1 Hz, 2H), 6.87 (q, J=5.5 Hz, 1H).

LCMS (m/z) 318.1 [M+H]$^+$.

Example 13: Succinic acid 1-acetoxy-ethyl ester acetoxymethyl ester i) Succinic acid 1-acetoxy-ethyl ester tert-butyl ester

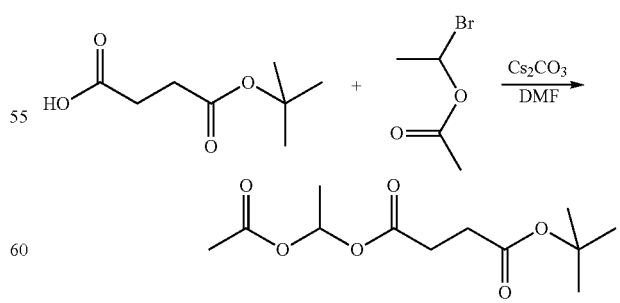

Succinic acid mono-tert-butyl ester (2.0 g, 11.48 mmol), acetic acid 1-bromo-ethyl ester (1.9 g, 11.48 mmol), caesium carbonate (2.6 g, 13.41 mmol) were suspended in DMF (20 mL) and the suspension stirred at 60° C. for 2 hours under an atmosphere of nitrogen. The suspension was cooled down to room temperature, diluted with ethyl acetate (50 mL) and washed with water (3×10 mL). The organics were combined and the volatiles were removed in vacuo. The residue was purified by silica gel chromatography with a continuous gradient of iso-hexane/ethyl acetate 1:0 to 0:1 to afford the title compound (2.21 g) as a clear oil.

$^1$H NMR (300 MHz, CDCl$_3$) δ 1.45 (s, 9H), 1.48 (d, J=5.5 Hz, 3H), 2.07 (s, 3H), 2.50-2.65 (m, 4H), 6.88 (q, J=5.5 Hz, 1H).

ii) Succinic acid mono-(1-acetoxy-ethyl) ester

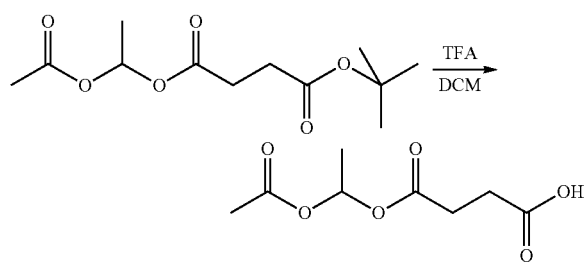

Succinic acid 1-acetoxy-ethyl ester tert-butyl ester (Example 13, step (i), 2.21 g, 8.49 mmol) was dissolved in DCM (10 mL), the solution was cooled to 0° C. and trifluoroacetic acid (2 mL) was added. The solution was allowed to warm to room temperature and stirred for 3 hours under an atmosphere of nitrogen. The volatiles were removed in vacuo the residue azeotroped with toluene (3×20 mL) to afford the title compound (1.52 g) as a clear oil.

$^1$H NMR (300 MHz, CDCl$_3$) δ 1.40 (d, J=5.5 Hz, 3H), 2.03 (s, 3H), 2.40-2.60 (m, 4H), 6.73 (q, J=5.5 Hz, 1H), 10-14 (br, 1H).

Example 13: Succinic acid 1-acetoxy-ethyl ester acetoxymethyl ester

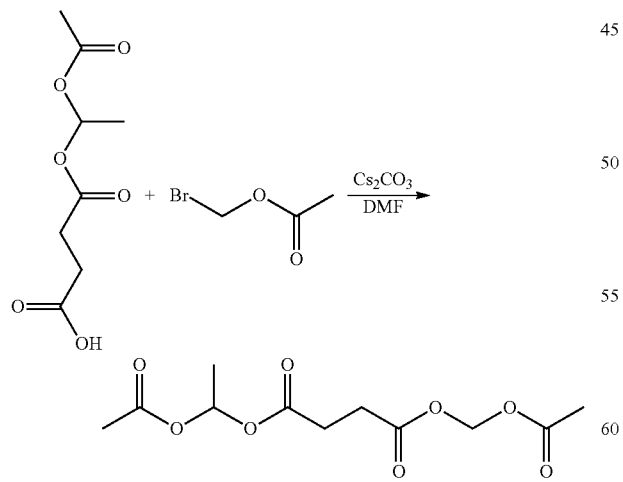

Succinic acid mono-(1-acetoxy-ethyl) ester (Example 13, step (ii), 500 mg, 2.45 mmol), acetic acid bromomethyl ester (450 mg, 2.93 mmol), caesium carbonate (712 mg, 3.67 mmol), were suspended in DMF (10 mL) and the suspension stirred at 60° C. for 3 hours under an atmosphere of nitrogen. The suspension was cooled down to room temperature, diluted with ethyl acetate (30 mL) and washed with water (3×5 mL). The organics were combined and the volatiles were removed in vacuo. The residue was purified by silica gel chromatography with a continuous gradient of iso-hexane/ethyl acetate 1:0 to 0:1 to afford the title compound (267 mg) as a clear oil.

$^1$H NMR (300 MHz, CDCl$_3$) δ 1.49 (d, J=5.5 Hz, 3H), 2.08 (s, 3H), 2.13 (s, 3H), 2.60-2.77 (m, 4H), 5.76 (s, 2H), 6.87 (q, J=5.5 Hz, 1H).

LCMS (m/z) 377.0 [M+H]$^+$.

Example 14: Succinic acid bis-(2,2-dimethyl-5-oxo-[1,3]dioxolan-4-yl) ester

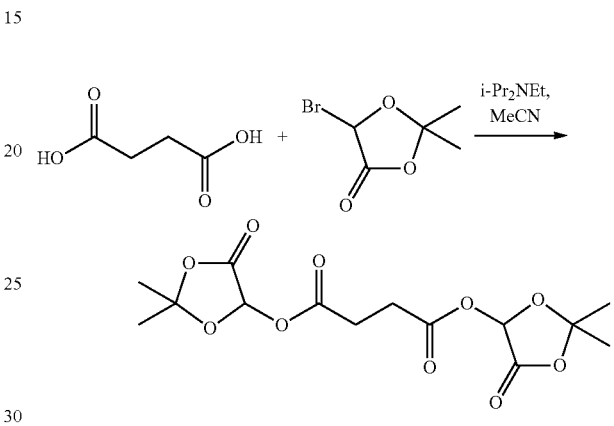

To succinic acid (2.36 g, 20 mmol) and diisopropylethylamine (8.1 mL, 46.5 mmol) in acetonitrile under an atmosphere of nitrogen and cooled in an ice bath was added 5-bromo-2,2-dimethyl-[1,3]dioxolan-4-one (8.27 g, 42.4 mmol). The mixture was allowed to warm to room temperature over 18 h. The solution was re-cooled in an ice bath, diluted with ethyl acetate and washed with 1M HCl, water, aqueous sodium hydrogen carbonate solution and water. The organic phase was dried over magnesium sulphate and concentrated to afford the title compound (3.4 g) as a white solid.

$^1$H NMR (300 MHz, CDCl$_3$) δ 1.15 (m, 12H), 2.41 (m, 4), 5.77 (m, 2H).

Example 15: Succinic acid bis-(methoxy-methoxycarbonyl-methyl) ester

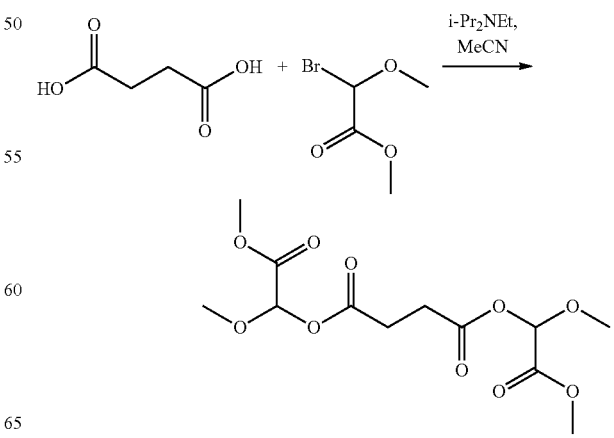

The titled compound was prepared by the method according to Example 14.

$^1$H NMR (300 MHz, CDCl$_3$) δ 2.83 (4H, m), 3.47 (6H s), 3.59 (6H, s), 5.97 (2H, s).

Example 16: Succinic acid 1-acetoxy-ethyl ester 1-ethoxycarbonyloxy-ethyl ester

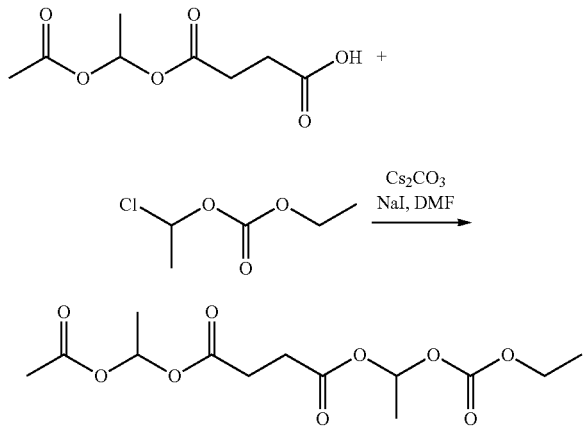

Succinic acid mono-(1-acetoxy-ethyl) ester (Example 13, step (ii), 1 g, 4.90 mmol), 1-chloroethyl ethyl carbonate (895 mg, 5.88 mmol), caesium carbonate (1.4 g, 7.35 mmol) and sodium iodide (73 mg, 0.49 mmol) were dissolved in DMF (15 mL) and the mixture heated to 80° C. for 3 hours. The mixture was allowed to cool to room temperature and then partitioned between water and ethyl acetate. The organic layer was dried over magnesium sulphate and concentrated to afford a crude residue which was purified by chromatography on silica gel chromatography with a continuous gradient of isohexane/ethyl acetate 1:0 to 0:1 to afford the title compound (118 mg).

$^1$H NMR (300 MHz, CDCl$_3$) δ 1.31 (t, J=7.1 Hz, 3H), 1.46 (d, J=5.4 Hz, 3H), 1.51 (d, J=5.4 Hz, 3H), 2.06 (s, 3H), 2.56-2.74 (m, 4H), 4.21 (q, J=7.1 Hz, 2H), 6.76 (q, J=5.4 Hz, 1H), 6.85 (q, J=5.4 Hz, 1H).

Example 17: Succinic acid 3-(1-acetoxy-ethoxycarbonyl)-propionyloxymethyl ester 1-acetoxy-ethyl ester i) Succinic acid 3-tert-butoxycarbonyl-propionyloxymethylester tert-butyl ester

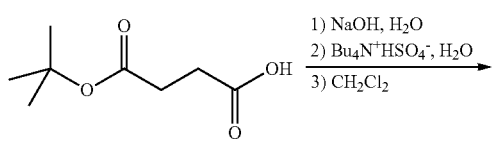

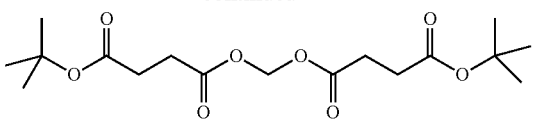

To t-butyl succinate (8.7 g, 50 mmol) was added aqueous sodium hydroxide solution (50 mL, 2M) and the mixture stirred for 10 min. Tetrabutyammonium hydrogen sulphate (17 g) was added and the mixture stirred for a further 30 min. The solution was extracted with dichloromethane (4×100 mL) and the combined extracts dried over magnesium sulphate. The dichloromethane solution was then heated at 40° C. for 5 days. The solution was allowed to cool to room temperature and washed with sulphuric acid (1M), water and sodium hydrogen carbonate solution followed by water. The organic phase was then dried and concentrated to afford the titled compound as crude product (5.7 g).

$^1$H NMR (CDCl$_3$, ppm) δ 1.45 (s, 18H), 2.53-2.67 (m, 8H), 5.79 (m, 2H).

ii) Succinic acid mono-(3-carboxy-propionyloxymethyl) ester

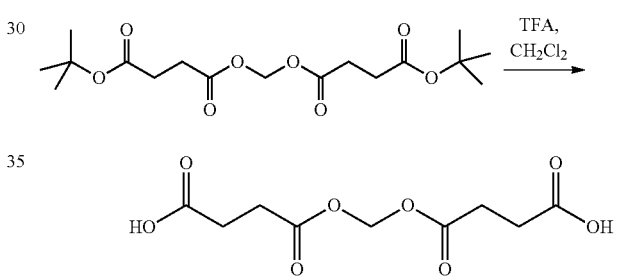

Succinic acid 3-tert-butoxycarbonyl-propionyloxymethylester tert-butyl ester (1.8 g, 5 mmol) was dissolved in dichloromethane (27 mL) and the mixture cooled to −78° C. under nitrogen. Trifluoroacetic acid (0.77 mL, 10 mmol) was added and the mixture allowed to warm to 4° C. after which it was maintained at 4° C. for 18 h. The mixture was evaporated and azeotroped with toluene. Analysis showed incomplete reaction so the crude mixture was subjected to the same reaction conditions for a further 4 days. The mixture was evaporated and azeotroped with toluene and used in the following step as a crude product (1.3 g).

$^1$H NMR (CDCl$_3$, ppm) δ 2.52-2.64 (m, 8H), 5.71 (s, 2H).

Example 17: Succinic acid 3-(1-acetoxy-ethoxycarbonyl)-propionyloxymethyl ester 1-acetoxy-ethyl ester

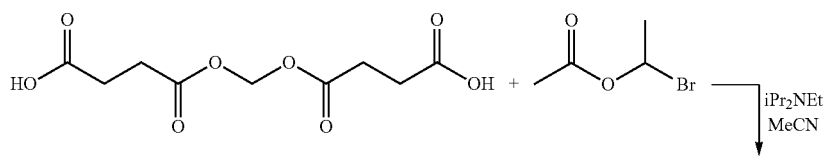

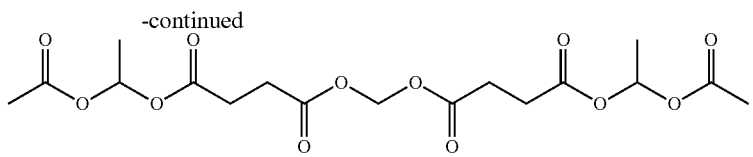

The titled compound was prepared by the method of Example 6 using succinic acid mono-(3-carboxy-propionyloxymethyl) ester (Ex 17ii, 1.3 g) and 1-bromoethyl acetate (1.8 g) to afford 240 mg of product after purification.

$^1$H NMR (CDCl$_3$, ppm) δ 1.50 (d, 6H), 2.09 (s, 6H), 2.60-2.75 (m, 8H), 5.78 (s, 2H), 6.90 (q, 2H).

Example 18: Succinic acid 3-acetoxymethoxycarbonyl-propionyloxymethyl ester acetoxymethyl ester

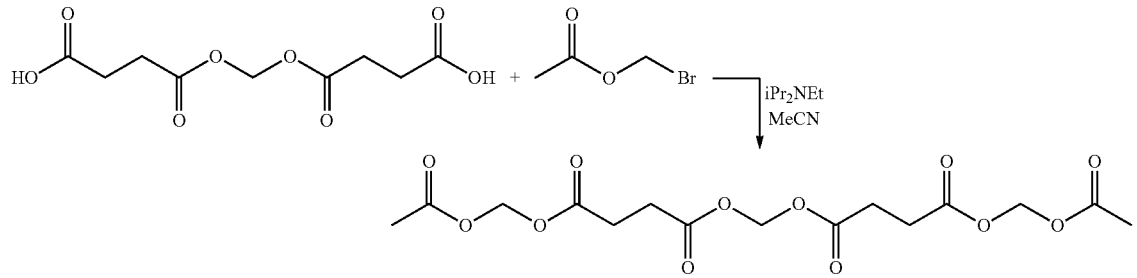

The titled compound was prepared by the method of Example 6 using succinic acid mono-(3-carboxy-propionyloxymethyl) ester (Ex 17ii, 1.0 g, 4.0 mmol) and 1-bromomethyl acetate (1.3 g, 8.5 mmol) to afford 1.4 g of product after purification.

$^1$H NMR (CDCl$_3$, ppm) δ 2.15 (s, 6H), 2.73 (s, 8H), 5.72-5.82 (m, 6H).

Example 19

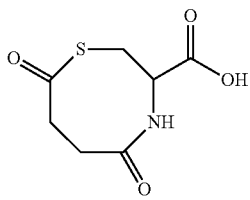

Succinyl chloride (0.1 mol) and triethylamine (0.4 mol) is dissolved in DCM and cysteine is added. The reaction is stirred at room temperature. The reaction is added to aqueous dilute hydrochloric acid and then is washed water and brine. The organic layers are dried over magnesium sulfate and reduced in vacuo. The target compound is the purified by silica gel chromatography.

Example 20—Synthesis of S,S-bis(2-propionamidoethyl) butanebis(thioate) (NV038, 01-038)

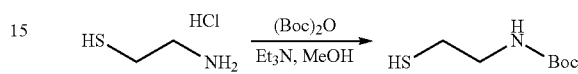

To a solution of cysteamine hydrochloride (5.0 g, 44 mmol) in CH$_3$OH (50 mL) was added Et$_3$N (4.4 g, 44 mmol), followed by (Boc)$_2$O (10.5 g, 48.4 mmol) and the mixture was stirred at room temperature for 1 h. The reaction mixture was concentrated in vacuo. The obtained residue was dissolved in CH$_2$Cl$_2$, washed with 2M HCl aqueous solution and brine, dried over Na$_2$SO$_4$, filtered and evaporated to yield tert-butyl 2-mercaptoethylcarbamate as a colorless oil which was used in the next step without further purification.

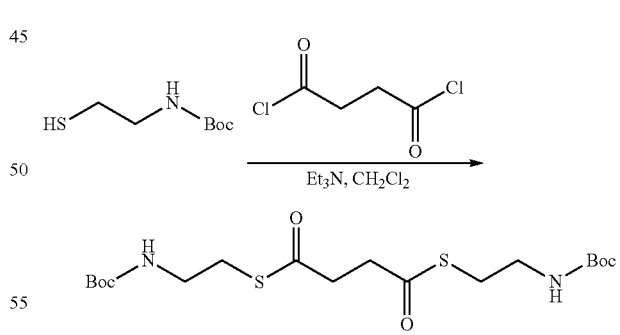

tert-Butyl 2-mercaptoethylcarbamate (9.8 g, 55.0 mmol) and Et$_3$N (5.6 g, 55.0 mmol) were dissolved in CH$_2$Cl$_2$ (100 mL), the mixture cooled to 0° C., succinyl chloride (2.1 g, 13.8 mmol) was added with dropwise. Then the mixture was stirred at room temperature for 2 h. The reaction mixture concentrated and the residue was purified by column chromatography (petrol ether/EtOAc=1/10 to 1/1). S,S-bis(2-(tert-butoxycarbonylamino)ethyl) butanebis(thioate) was obtained as a white solid.

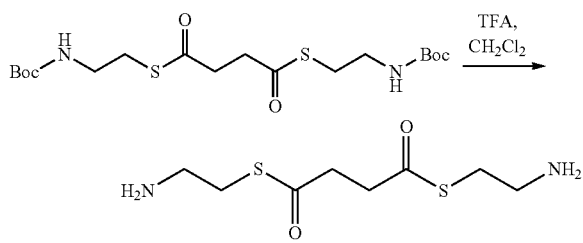

A mixture of S,S-bis(2-(tert-butoxycarbonylamino)ethyl) butanebis(thioate) (2.0 g, 4.58 mmol) and TFA (10 mL) in CH₂Cl₂ (10 mL) was stirred at room temperature for 4 hours. The reaction mixture was concentrated to yield S,S-bis(2-aminoethyl) butanebis(thioate) as a yellow oil which was used in the next step without further purification.

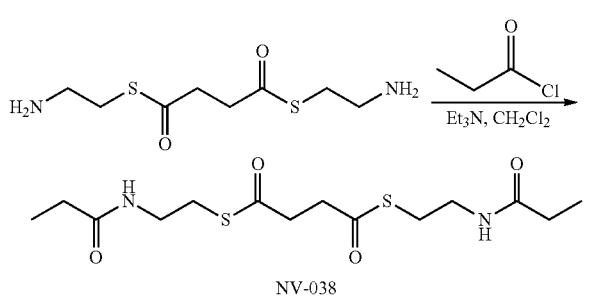

NV-038

S,S-bis(2-aminoethyl) butanebis(thioate) (1.1 g, 4.58 mmol) and Et₃N (1.4 g, 13.74 mmol) were dissolved in CH₂Cl₂ (15 mL), the mixture cooled to 0° C., propionyl chloride (0.9 g, 10.07 mmol) was added with dropwise. Then the mixture was stirred at room temperature for 3 hours. The reaction mixture concentrated and the residue was purified by preparative TLC (CH₂Cl₂/MeOH=15/1). S,S-bis(2-Propionamidoethyl) butanebis(thioate) was obtained as a white solid.

Example 21—Synthesis of (R)-4-(2-carboxy-2-propionamidoethylthio)-4-oxobutanoic acid (NV-041, 01-041)

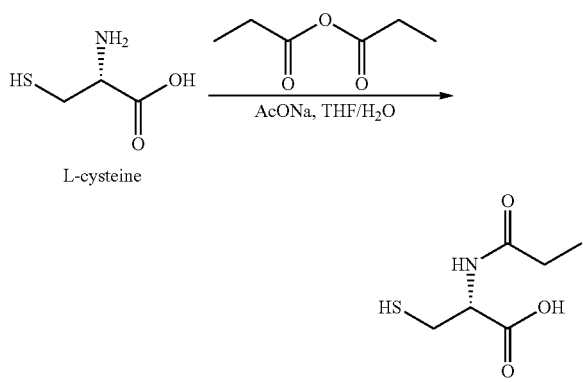

L-cysteine

To a mixture of L-cysteine (2.00 g, 16.5 mmol) in THF/H₂O (8 mL/2 mL) was added NaOAc (2.70 g, 33.0 mmol). The mixture was stirred at room temperature for 20 min. The reaction was cooled to 5° C. before propionic anhydride (2.30 g, 17.6 mmol) was added dropwise. The reaction mixture was stirred at room temperature overnight and then heated to reflux for 4 hours. The reaction mixture was cooled and acidified to pH 5 by adding 4N HCl. The resulting solution was evaporated under reduced pressure to remove THF. The residue was purified by prep-HPLC (eluting with H₂O (0.05% TFA) and CH₃CN) to give 1.00 g of (R)-3-mercapto-2-propionamidopropanoic acid as colourless oil.

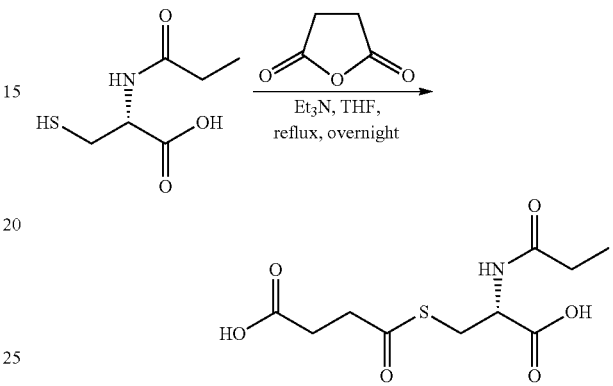

A solution of (R)-3-mercapto-2-propionamidopropanoic acid (1.00 g, 5.65 mmol), succinic anhydride (565 mg, 5.65 mmol) and Et₃N (572 mg, 5.65 mmol) in 10 mL of THF was heated under reflux overnight. The reaction mixture concentrated and the residue was purified by preparative-HPLC (eluting with H₂O (0.05% TFA) and CH₃CN) to yield (R)-4-(2-carboxy-2-propionamidoethylthio)-4-oxobutanoic acid as a colourless oil.

Example 22

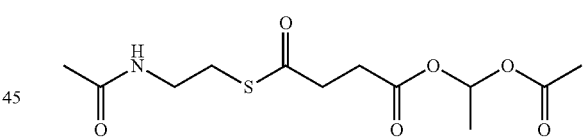

Step 1

Triethylamine (0.24 mol) is added to a solution of N-acetylcysteamine (0.2 mol) in DCM. 4-Chloro-4-oxobutanoic acid (0.1 mol) is added dropwise, and the reaction mixture is stirred at room temperature. The mixture is added to aqueous dilute hydrochloric acid and is extracted with ethyl acetate, and then is washed water and brine. The organic layers are dried over magnesium sulfate and reduced in vacuo.

Step 2

The product of step 3 (0.1 mol), acetic acid 1-bromoethyl ester (0.1 mol) and caesium carbonate (0.12 mol) is suspended in DMF and stirred at 60° C. under an inert atmosphere. The suspension is allowed to cool to room temperature and ethyl acetate added and is washed successively with aqueous dilute hydrochloric acid and water. The organics are dried over magnesium sulfate and reduced in vacuo. The residue is purified by column chromatography.

Example 23

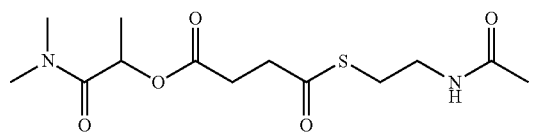 [SMILES: CC(=O)NCCSC(=O)CCC(=O)OC(C)C(=O)N(C)C]

Step 1
Triethylamine (0.24 mol) is added to a solution of N-acetylcysteamine (0.2 mol) in DCM. 4-Chloro-4-oxobutanoic acid (0.1 mol) is added dropwise, and the reaction mixture is stirred at room temperature. The mixture is added to aqueous dilute hydrochloric acid and is extracted with ethyl acetate, and then is washed water and brine. The organic layers are dried over magnesium sulfate and reduced in vacuo.

Step 2
Dimethylamine (0.1 mol) and triethylamine (0.1 mol) are diluted in dichloromethane, the solution is cooled to 0° C. and 2-chloropropionyl chloride (0.1 mol) in DCM is added and the solution is allowed to warm to room temperature and is left to stir under an inert atmosphere. The solution is washed with water. The organics are combined and the volatiles are removed in vacuo. The residue is purified by silica gel chromatography.

Step 3
2-Chloro-N,N-dimethyl-propionamide (0.1 mol), the product of step 1 (0.1 mol), caesium carbonate (0.1 mol), and sodium iodide (0.01 mol) is suspended in DMF and the suspension stirred at 80° C. under an inert atmosphere. The suspension is cooled to room temperature, is diluted with ethyl acetate and is washed with water. The organics are reduced in vacuo. The residue is purified by silica gel chromatography to yield the target compound.

Example 24—Synthesis of 4-oxo-4-(2-propionamidoethylthio)butanoic acid (NV114, 01-114)

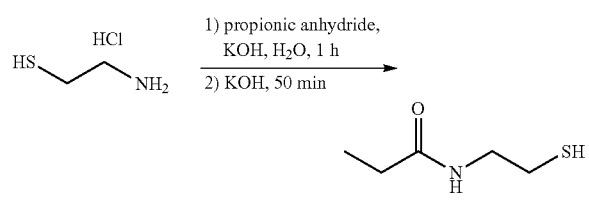

Propionic anhydride (11.7 g, 89.7 mmol) and aqueous KOH (8 M, to maintain pH=8) were added dropwise to a stirred solution of cysteamine hydrochloride (3.40 g, 30.0 mmol) in 24 mL of water. The mixture was neutralized by adding 2N HCl and stirred for 1 hour at room temperature. The solution was cooled with an ice bath and solid KOH (6.00 g, 105 mmol) was added slowly. The mixture was stirred for 50 minutes at room temperature. After saturated with NaCl and neutralized with 6N HCl, the mixture was extracted with $CH_2Cl_2$ (4×30 mL). The combined $CH_2Cl_2$ extracts were dried ($Na_2SO_4$) and concentrated in vacuo to give N-(2-mercaptoethyl)propionamide as colourless oil, which was used for next step without further purification.

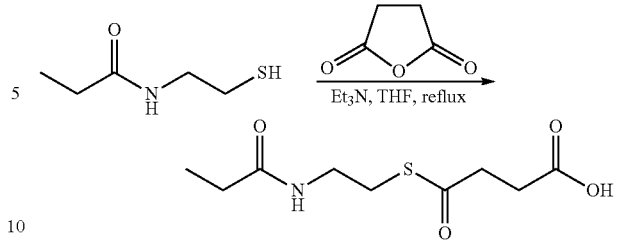

A solution of N-(2-mercaptoethyl)propionamide (2.00 g, 15.0 mmol), succinic anhydride (1.50 g, 15.0 mmol) and $Et_3N$ (1.50 g, 15.0 mmol) in 20 mL of THF was heated under reflux overnight. The reaction mixture was concentrated and the residue was purified by preparative-HPLC (eluting with $H_2O$ (0.05% TFA) and $CH_3CN$) to yield 4-oxo-4-(2-propionamidoethylthio)butanoic acid as colourless oil.

Example 25—Synthesis of 4-(2-acetamidoethylthio)-4-oxobutanoic acid (NV108, 01-108)

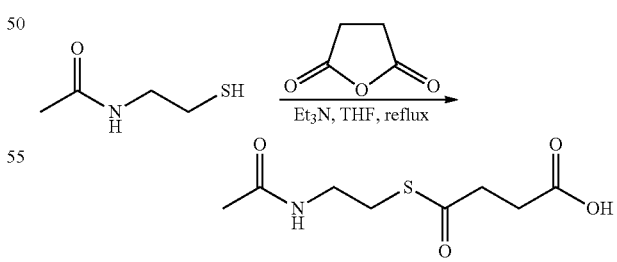

Acetic anhydride (8.48 mL, 90.0 mmol) and aqueous KOH (8 M, to maintain pH=8) were added dropwise to a stirred solution of cysteamine hydrochloride (3.40 g, 30.0 mmol) in 24 mL of water. The pH was then adjusted to 7 with adding 2N HCl. The mixture was stirred for 1 hour at room temperature, and then the solution was cooled with an ice bath. To the above solution, solid KOH (6.0 g, 105 mmol) was added slowly, and the resulting mixture was stirred for 50 minutes at room temperature. After saturated with NaCl and neutralized with 6N HCl, the mixture was extracted with $CH_2Cl_2$ (4×30 mL). The combined $CH_2Cl_2$ extracts were dried ($Na_2SO_4$) and concentrated in vacuo to give N-(2-mercaptoethyl)acetamide as colourless oil, which was used for next step without further purification.

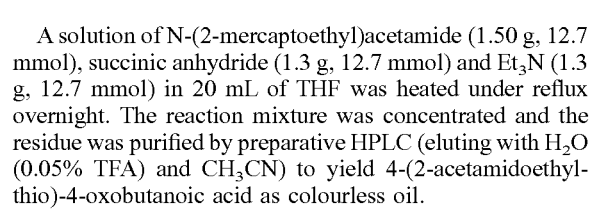

A solution of N-(2-mercaptoethyl)acetamide (1.50 g, 12.7 mmol), succinic anhydride (1.3 g, 12.7 mmol) and $Et_3N$ (1.3 g, 12.7 mmol) in 20 mL of THF was heated under reflux overnight. The reaction mixture was concentrated and the residue was purified by preparative HPLC (eluting with $H_2O$ (0.05% TFA) and $CH_3CN$) to yield 4-(2-acetamidoethylthio)-4-oxobutanoic acid as colourless oil.

Example 26—The synthesis of (R)-3-(4-((R)-2-carboxy-2-propionamidoethylthio)-4-oxobutanoyl-thio)-2-propionamidopropanoic acid (NV099, 01-099)

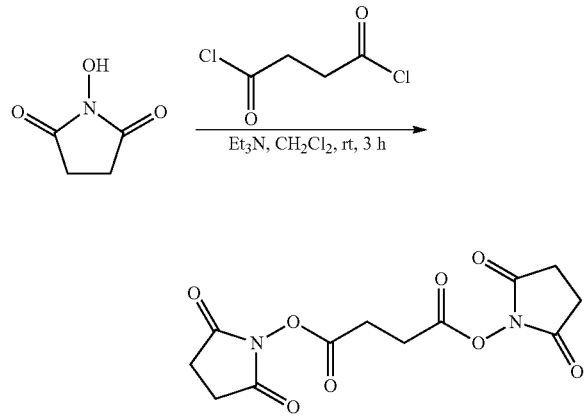 [SMILES: O=C1CCC(=O)N1O ; O=C(Cl)CCC(=O)Cl ; O=C(CCC(=O)ON1C(=O)CCC1=O)ON1C(=O)CCC1=O]

To a mixture of N-hydroxysuccinimide (3.00 g, 26.1 mmol) and Et₃N (3.20 g, 31.3 mmol) in CH₂Cl₂ (60 mL) was added dropwise succinyl chloride (2.00 g, 13.0 mmol). The mixture was stirred at room temperature for 3 hours before diluted with water (60 mL). The resulting suspension was filtered, washed with water and CH₂Cl₂. The cake was collected and dried to give bis(2,5-dioxopyrrolidin-1-yl) succinate as a grey solid.

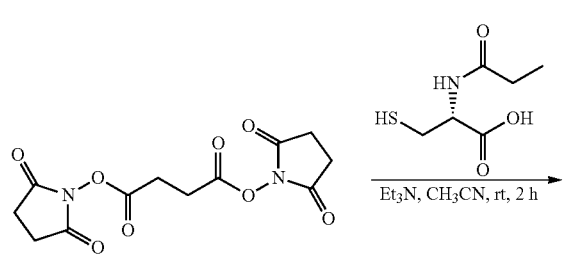

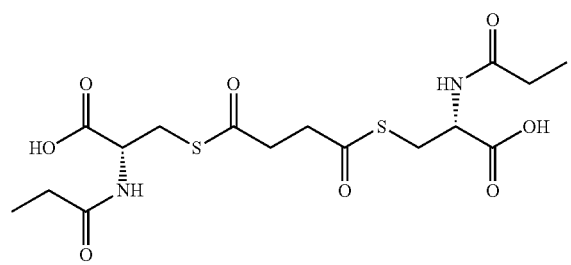

A mixture of N-(2-mercaptoethyl)propionamide (400 mg, 2.26 mmol), bis(2,5-dioxopyrrolidin-1-yl) succinate (353 mg, 1.13 mmol) and TEA (286 mg, 2.83 mmol) in 3.0 mL of CH₃CN was stirred at room temperature for 2 hours. The clear reaction solution was purified by preparative-HPLC (eluting with H₂O (0.05% TFA) and CH₃CN) directly to yield (R)-3-(4-((R)-2-carboxy-2-propionamidoethylthio)-4-oxobutanoylthio)-2-propionamidopropanoic acid as colorless oil.

Example 27—Synthesis of (R)-4-(1-carboxy-2-(propionylthio)ethylamino)-4-oxobutanoic acid (NV122, 01-122)

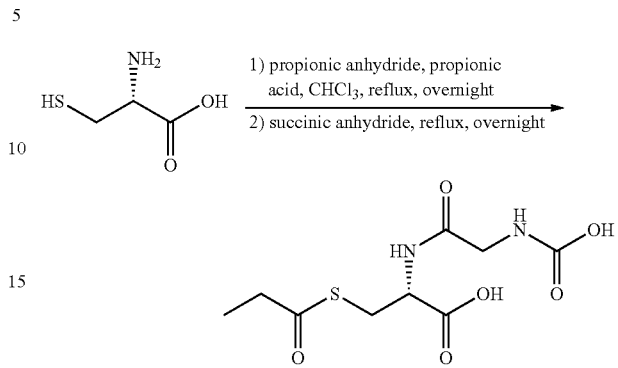

To a mixture of (R)-3-mercapto-2-propionamidopropanoic acid (1.00 g, 8.25 mmol) and propionic acid (1.0 mL) in CHCl₃ (10 mL) were added propionic anhydride (1.13 g, 8.67 mmol) dropwise. The reaction mixture was heated to reflux overnight. The reaction mixture was cooled and succinic anhydride (1.00 g, 9.99 mmol) was added. The mixture was refluxed overnight before concentrated under reduced pressure. The residue was purified by prep-HPLC (eluting with H₂O (0.05% TFA) and CH3CN) to yield (R)-4-(1-carboxy-2-(propionylthio)ethylamino)-4-oxobutanoic acid as an off-white solid.

Example 28—The synthesis of 4-(1-acetamido-2-methylpropan-2-ylthio)-4-oxobutanoic acid (NV188, 01-188)

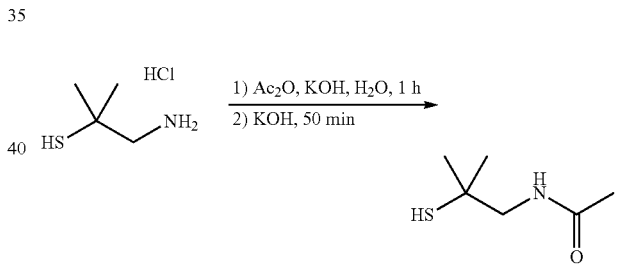

To a stirred solution of cysteamine hydrochloride (2.00 g, 14.1 mmol) in 15 mL of water was added acetic anhydride (4.30 g, 42.4 mmol) and aqueous KOH (8 M, to maintain pH=8) dropwise. The mixture was then neutralized by adding 2N HCl and stirred for 1 hour at room temperature. To the solution cooled with an ice bath was added slowly solid KOH (2.80 g, 49.4 mmol) and the mixture was stirred for 50 minutes at room temperature. After saturated with NaCl and neutralized with 6N HCl, the mixture was extracted with CH₂Cl₂ twice. The combined CH₂Cl₂ extracts were dried (Na₂SO₄) and concentrated in vacuo to yield N-(2-mercapto-2-methylpropyl)acetamide as a white solid which was used for next step without further purification.

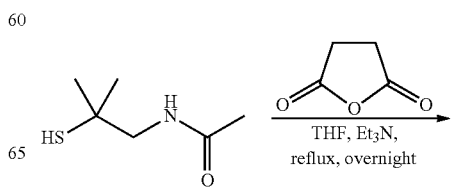

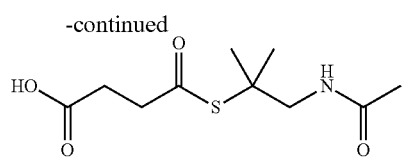

A solution of N-(2-mercapto-2-methylpropyl)acetamide (400 mg, 2.72 mmol), succinic anhydride (326 mg, 3.26 mmol) and Et₃N (330 mg, 3.26 mmol) in 6 mL of THF was heated under overnight. The reaction mixture was concentrated and the residue was purified by preparative-HPLC (eluting with H₂O (0.05% TFA) and CH₃CN) to yield 4-(1-acetamido-2-methylpropan-2-ylthio)-4-oxobutanoic acid as yellow oil.

Example 29—The Synthesis of S,S-bis((R)-3-(diethylamino)-3-oxo-2-propionamidopropyl) butanebis (thioate) (NV185, 01-185)

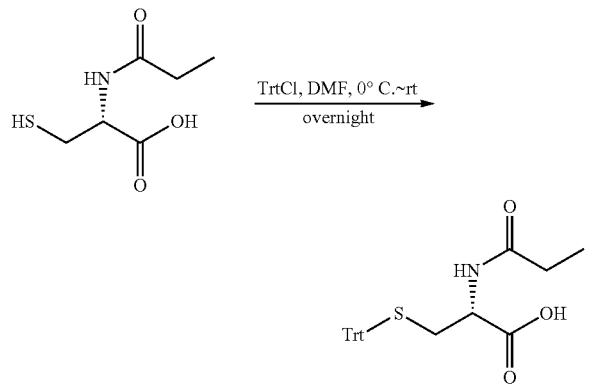

To a solution of (R)-3-mercapto-2-propionamidopropanoic acid (5.00 g, 28.0 mmol) in DMF (50 mL) was added triphenylmethyl chloride (8.70 g, 31.0 mmol) at 0° C. The mixture was stirred at 0° C. for 30 min and then warmed to room temperature overnight. The mixture was treated with water and extracted with EtOAc twice. The combined organic layers were washed with brine, dried over Na₂SO₄ and concentrated under reduced pressure. The residue was purified by silica gel column chromatography (CH₂Cl₂/MeOH=80/1~50/1) to yield (R)-2-propionamido-3-(tritylthio)propanoic acid as a white solid.

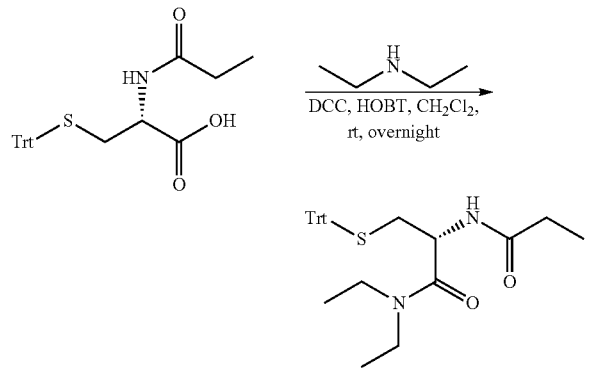

To a stirred solution of (R)-2-propionamido-3-(tritylthio)propanoic acid (1.7 g, 4.0 mmol) in CH₂Cl₂ (50 mL) was added DCC (1.7 g, 8.0 mmol) and HOBT (0.50 g, 4.0 mmol) at room temperature. The mixture was stirred at room temperature for 1 h and then diethylamine (0.80 g, 8.0 mmol) was added. The mixture was stirred at room temperature overnight. The mixture was washed with water, dried over Na₂SO₄ and concentrated under reduced pressure to give the crude product which was purified by silica gel column chromatography (EtOAc/petrol ether=1/6~1/1) to yield (R)—N,N-diethyl-3-mercapto-2-propionamidopropanamide as yellow oil.

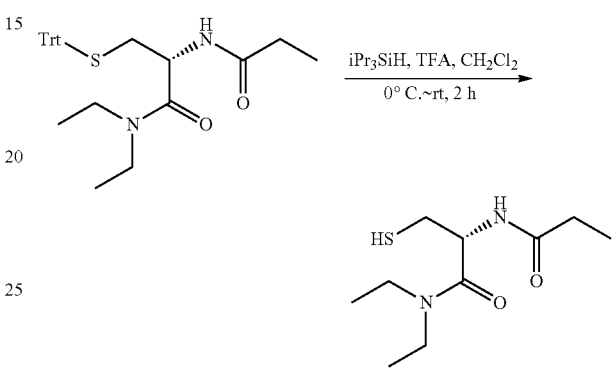

To a solution of (R)—N,N-diethyl-3-mercapto-2-propionamidopropanamide (400 mg, 0.800 mmol) in CH₂Cl₂ (10 mL) at 0° C. was added TFA (1 mL) and i-Pr3SiH (253 mg, 1.60 mmol). The mixture was warmed to room temperature and stirred for 2 hours. The solution was evaporated under reduced pressure. The residue was purified by preparative-HPLC (eluting with H₂O (0.5% TFA) and CH₃CN) to yield (R)—N,N-diethyl-3-mercapto-2-propionamidopropanamide as yellow oil.

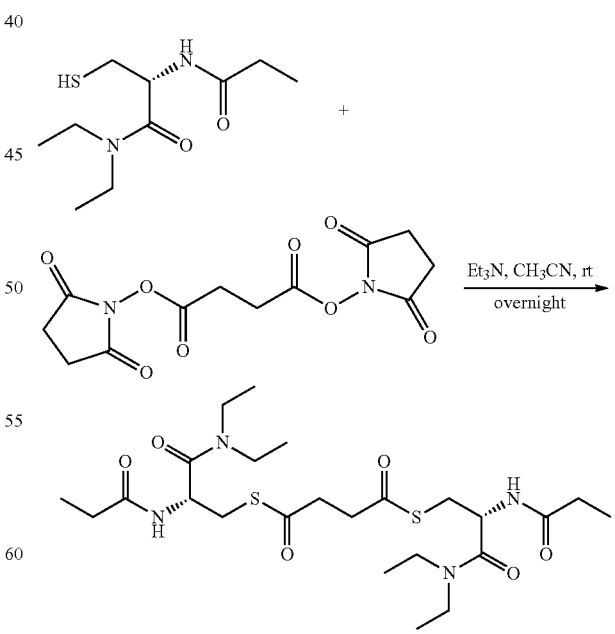

A mixture of (R)—N,N-diethyl-3-mercapto-2-propionamidopropanamide (150 mg, 0.600 mmol), Et₃N (242 mg, 2.40 mmol) and bis(2,5-dioxopyrrolidin-1-yl) succinate (94 mg, 0.30 mmol) in CH$_3$CN (100 mL) was stirred at room temperature overnight. The mixture was evaporated under reduced pressure. The residue was purified by preparative HPLC (eluting with H$_2$O (0.5% TFA) and CH$_3$CN) to yield S,S-bis((R)-3-(diethylamino)-3-oxo-2-propionamidopropyl) butanebis(thioate) (36% yield) as a yellow solid.

Example 30—The Synthesis of 4-(2-(2-(diethyl-amino)-2-oxoethoxy)ethylthio)-4-oxobutanoic acid (NV193, 01-193)

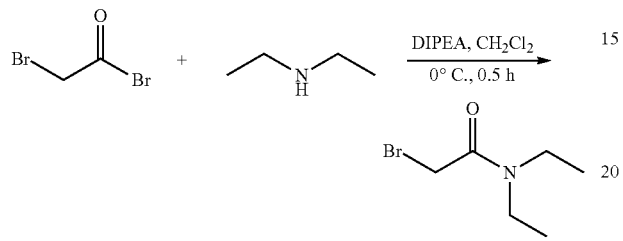

To a solution of 2-bromoacetyl bromide (4.00 g, 20.0 mmol) and DIPEA (2.60 g, 20 mmol) in CH$_2$Cl$_2$ (50 mL) was added dropwise diethylamine (1.60 g, 20.0 mmol) at 0° C. The mixture was stirred at 0° C. for 30 min. The solution was evaporated under reduced pressure to remove CH$_2$Cl$_2$. The residue was purified by silica gel column chromatography (EtOAc/petrol ether=1/5~1/2) to yield 2-bromo-N,N-diethylacetamide as yellow oil.

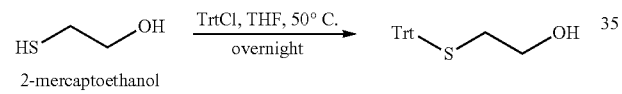

A solution of 2-mercaptoethanol (2.50 g, 32.0 mmol), triphenylmethyl chloride (10.7 g, 38.4 mmol) in 100 mL of THF was heated under reflux overnight. The reaction mixture was concentrated and the residue was purified by silica gel column chromatography (EtOAc/petrol ether=1/5~1/1) to yield 2-(2,2,2-triphenylethylthio)ethanol as a white solid.

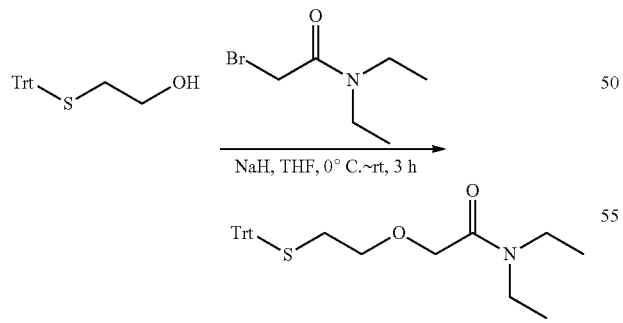

To a solution of 2-(2,2,2-triphenylethylthio)ethanol (3.50 g, 10.9 mmol) in THF (30 mL) was added NaH (0.500 g, 13.0 mmol, 60% in oil) in portions at 0° C. The reaction mixture was stirred at 0° C. for 1 hour. Then a solution of 2-bromo-N,N-diethylacetamide (2.1 g, 10.9 mmol) in THF (5 mL) was added dropwise. The resulting mixture was warmed to room temperature over 2 hours. The mixture was quenched with water and extracted with EtOAc twice. The combined organic layers were washed with brine, dried over Na$_2$SO$_4$ and concentrated under reduced pressure. The residue was purified by silica gel column chromatography (EtOAc/petrol ether=1/5~1/2) to yield N,N-diethyl-2-(2-(tritylthio)ethoxy)acetamide as a white solid.

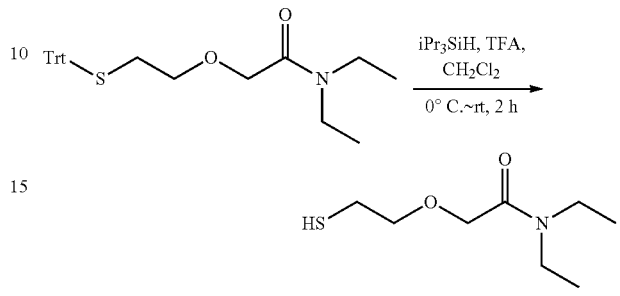

To a solution of N,N-diethyl-2-(2-(tritylthio)ethoxy)acetamide (2.70 g, 6.30 mmol) in CH$_2$Cl$_2$ (20 mL) was added TFA (2 mL) and i-Pr$_3$SiH (2.00 g, 12.6 mmol) at 0° C. The mixture was warmed to room temperature and stirred for 2 hours. The solution was evaporated under reduced pressure to remove CH$_2$Cl$_2$. The residue was purified by silica gel column chromatography (EtOAc/petrol ether=1/5~1/1) to yield N,N-diethyl-2-(2-mercaptoethoxy)acetamide as colorless oil.

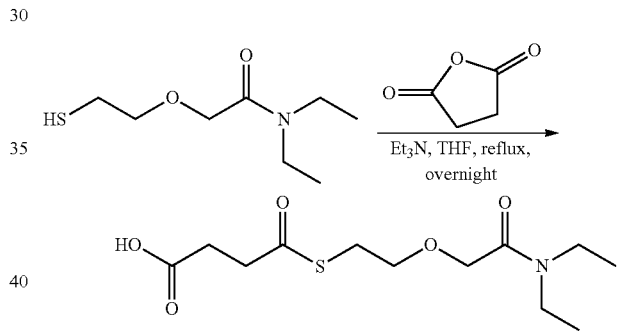

A solution of N,N-diethyl-2-(2-mercaptoethoxy)acetamide (356 mg, 1.90 mmol), succinic anhydride (200 mg, 2.10 mmol) and Et$_3$N (300 mg, 2.90 mmol) in 10 mL of THF was stirred at reflux overnight. The reaction mixture was concentrated in vacuo and the residue was purified by preparative HPLC (eluting with H$_2$O (0.5% TFA) and CH$_3$CN) to yield 4-(2-(2-(diethylamino)-2-oxoethoxy)ethylthio)-4-oxobutanoic acid as colorless oil.

Example 31—The Synthesis of (R)-methyl 3-(4-((R)-3-methoxy-3-oxo-2-propionamidopropylthio)-4-oxobutanoylthio)-2-propionamidopropanoate (NV205, 01-205)

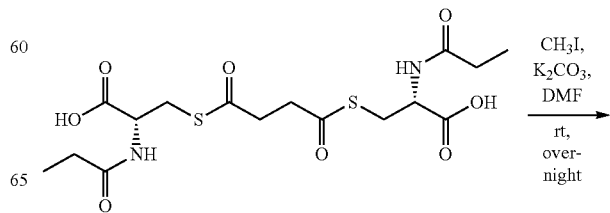

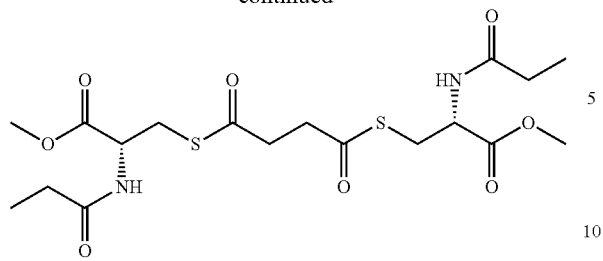

A mixture of (R)-3-(4-((R)-2-carboxy-2-propionamido-ethylthio)-4-oxobutanoylthio)-2-propionamidopropanoic acid (300 mg, 0.69 mmol), CH₃I (293 mg, 2.06 mmol) and K₂CO₃ (475 mg, 3.44 mmol) in 4.0 mL of DMF was stirred at room temperature overnight. The reaction mixture was filtered and the filtrate was purified by preparative-HPLC (eluting with H₂O (0.05% TFA) and CH₃CN) directly to yield (R)-methyl 3-(4-((R)-3-methoxy-3-oxo-2-propionami-dopropylthio)-4-oxobutanoylthio)-2-propionamidopropano-ate as an off-white solid.

Example 32—Synthesis of NV189

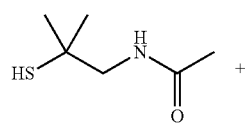 +

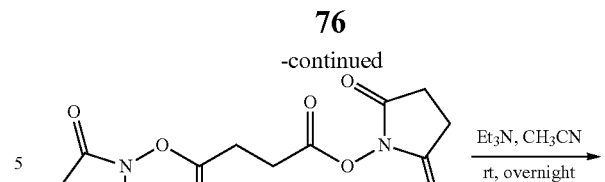

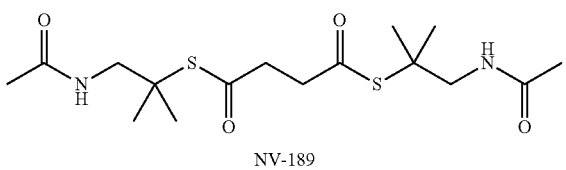

NV-189

A mixture of N-(2-mercapto-2-methylpropyl)acetamide (400 mg, 2.72 mmol), bis(2,5-dioxopyrrolidin-1-yl) succi-nate (339 mg, 1.09 mmol) and Et₃N (550 mg, 5.44 mmol) in 6 mL of CH₃CN was stirred at room temperature overnight. The reaction mixture was concentrated and the residue was purified by preparative HPLC (eluting with H₂O (0.05% TFA) and CH₃CN) to yield NV189 as an off-white solid.

Example 33—Synthesis of S,S-bis(2-(2-(diethyl-amino)-2-oxoethoxy)ethyl) butane-bis(thioate) (NV195, 01-195)

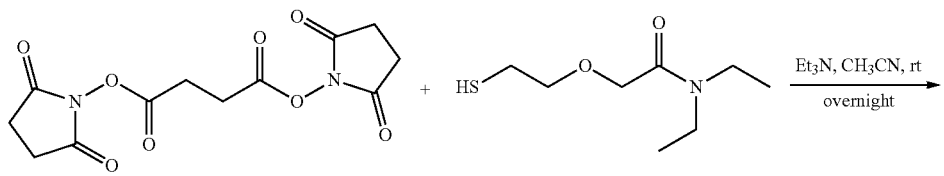

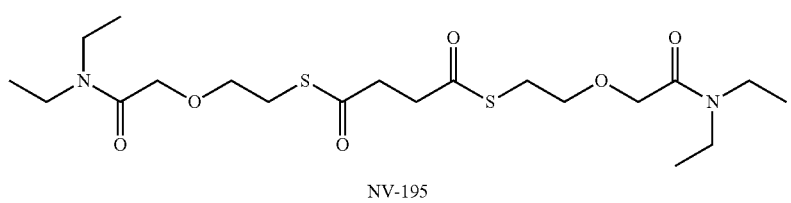

NV-195

To a solution of N,N-diethyl-2-(2-mercaptoethoxy)acetamide (438 mg, 2.3 mmol) in CH₃CN (10 mL) was added bis(2,5-dioxopyrrolidin-1-yl) succinate (374 mg, 1.2 mmol) and Et₃N (232 mg, 2.3 mmol). The mixture was stirred at room temperature overnight. The reaction mixture was concentrated in vacuo and the residue was purified by preparative HPLC (eluting with H₂O (0.5% TFA) and CH₃CN) to yield S,S-bis(2-(2-(diethylamino)-2-oxoethoxy)ethyl) butanebis(thioate) as a colorless oil.

Example 34—Synthesis of NV206

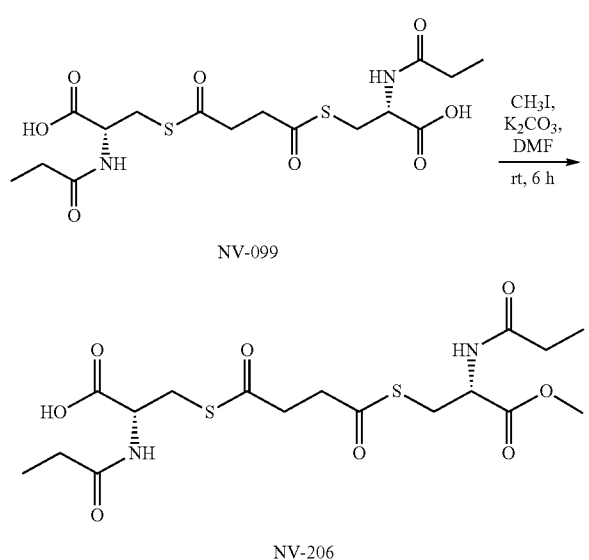

A mixture of (R)-3-(4-((R)-2-carboxy-2-propionamidoethylthio)-4-oxobutanoylthio)-2-propionamidopropanoic acid (400 mg, 0.916 mmol), CH₃I (156 mg, 1.1 mmol) and K₂CO₃ (190 mg, 1.37 mmol) in 4 mL of DMF was stirred at room temperature for 6 hours. The reaction mixture was filtered and the filtrate was purified by prep-HPLC (eluting with H₂O (0.05% TFA) and CH₃CN) directly to yield NV206 as a colorless gum.

Example 35—Synthesis of NV134 (01-134)

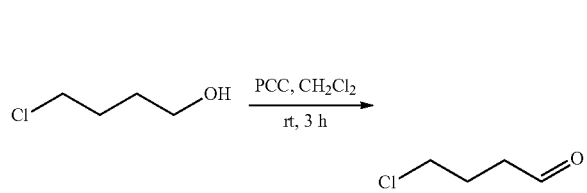

A solution of 4-chlorobutan-1-ol (8.00 g, 73.7 mmol) and PCC (23.8 g, 110.5 mmol) in CH₂Cl₂ (200 mL) was stirred for 3 hours at room temperature. The mixture was then diluted with ether, filtered through a pad of celite and neutral alumina. The black gum was triturated in ether. The filtrate was concentrated to give 5.70 g of 4-chlorobutanal as pale yellow liquid which was used in next step without further purification.

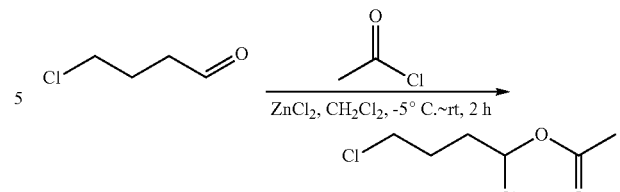

To a mixture of ZnCl₂ (120 mg, 0.9 mmol) and acetyl chloride (3.50 g, 44.1 mmol) at −5° C. under nitrogen was added dropwise a solution of 4-chlorobutanal (4.70 g, 44.1 mmol) in CH₂Cl₂ (7 mL). The mixture was stirred at −5° C. for 1 hour and then at room temperature for 1 hour. The mixture was diluted with water and extracted with CH₂Cl₂ twice. The combined CH₂Cl₂ extracts were washed with water, dried (Na₂SO₄) and concentrated to yield 1,4-dichlorobutyl acetate as yellow oil which was used for next step without further purification.

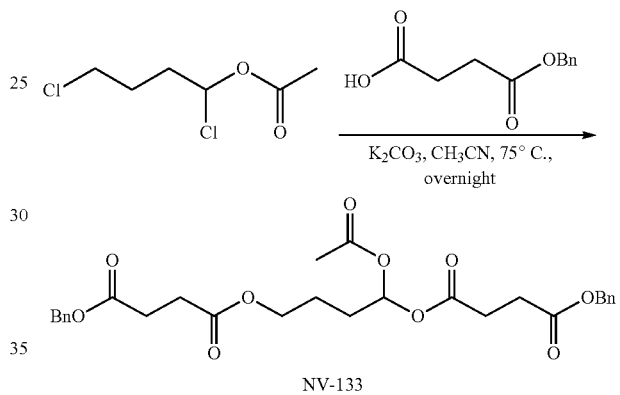

To a solution of 1,4-dichlorobutyl acetate (1.2 g, 6.48 mmol) and succinic acid monobenzyl ester (1.35 g, 6.48 mmol) in CH₃CN (15 mL) was added K₂CO₃ (0.98 g, 7.08 mmol) and NaI (0.09 g, 0.59 mmol). The resulting mixture was stirred at 75° C. overnight. The mixture was diluted with water and extracted with EtOAc twice. The combined organic extracts were dried (Na₂SO₄) and concentrated. The residue was purified by silica gel column chromatography (EtOAc/petrol ether=1/10~1/5) to yield NV-133 as colorless oil.

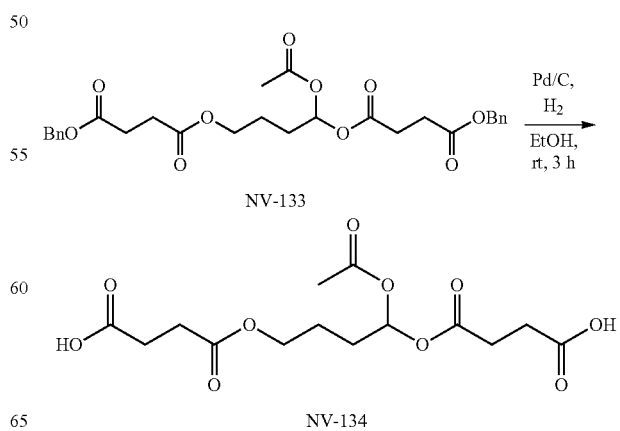

A mixture of NV-133 (450 mg, 0.85 mmol) and Pd/C (10%, 200 mg) in EtOH (20 mL) was stirred at room temperature under hydrogen atmosphere (balloon) for 3 hours. The reaction mixture was filtered and concentrated under reduced pressure to yield NV-134 as colorless oil.

Example 36—Synthesis of 4-(1-acetoxy-4-(1,3-dioxoisoindolin-2-yl)butoxy)-4-oxobutanoic acid (NV150, 01-150)

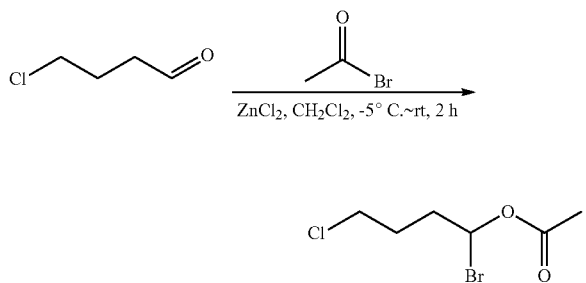

To a mixture of ZnCl₂ (26.0 mg, 0.190 mmol) and acetyl bromide (1.15 g, 9.40 mmol) at −5° C. under nitrogen, was added dropwise a solution of 4-chlorobutanal (1.0 g, 9.4 mmol) in CH₂Cl₂ (1.5 mL). The mixture was stirred at −5° C. for 1 hour and then at room temperature for 1 hour. The mixture was diluted with water and extracted with CH₂Cl₂ twice. The combined CH₂Cl₂ extracts were washed with water, dried (Na₂SO₄) and concentrated under reduced pressure to yield 1-bromo-4-chlorobutyl acetate as yellow oil, which was used for next step without further purification.

To a solution of 1-bromo-4-chlorobutyl acetate (1.3 g, 5.6 mmol) and succinic acid monobenzyl ester (1.1 g, 5.1 mmol) in CH₃CN (15 mL) was added K₂CO₃ (0.85 g, 6.1 mmol). The mixture was stirred at room temperature overnight. The mixture was diluted with water and extracted with EtOAc twice. The combined organic extracts were dried (Na₂SO₄) and concentrated. The residue was purified by silica gel column chromatography (EtOAc/petrol ether=1/10~1/5) to yield 1-acetoxy-4-chlorobutyl benzyl succinate as colorless oil.

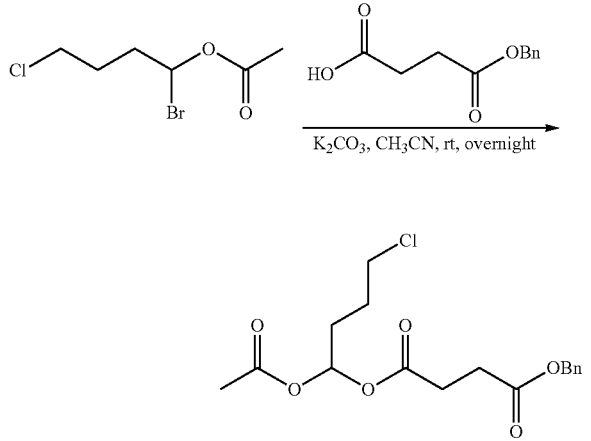

To a solution of compound 1-acetoxy-4-chlorobutyl benzyl succinate (900 mg, 2.50 mmol) and O-phthalimide (371 mg, 2.50 mmol) in DMF (20 mL) was added K₂CO₃ (522 mg, 3.80 mmol). The mixture was stirred at 80° C. overnight. The mixture was diluted with water and extracted with EtOAc twice. The combined organic extracts were dried (Na₂SO₄) and concentrated. The residue was purified by silica gel column chromatography (EtOAc/petrol ether=1/10~1/3) to give 1-acetoxy-4-(1,3-dioxoisoindolin-2-yl)butyl benzyl succinate (550 mg, 46% yield) as a slight yellow solid.

A mixture of 1-acetoxy-4-(1,3-dioxoisoindolin-2-yl)butyl benzyl succinate (400 mg, 0.86 mmol) and Pd/C (10%, 100 mg) in EtOH (20 mL) was stirred at room temperature under hydrogen atmosphere (balloon) for 4 hours. The reaction mixture was filtered and concentrated under reduced pressure. The residue was purified by preparative HPLC (eluting with H$_2$O (0.05% TFA) and CH$_3$CN) to yield 4-(1-acetoxy-4-(1,3-dioxoisoindolin-2-yl)butoxy)-4-oxobutanoic acid as a white solid.

REFERENCES

Al-Abri, S. A., Hayashi, S., Thoren, K. L. & Olson, K. R. 2013. Metformin overdose-induced hypoglycemia in the absence of other antidiabetic drugs. *Clin Toxicol (Phila)*, 51, 444-7.

Bailey, C. J. 1992. Biguanides and NIDDM. *Diabetes Care*, 15, 755-72.

Boyum, A. 1968. Isolation of mononuclear cells and granulocytes from human blood. Isolation of monuclear cells by one centrifugation, and of granulocytes by combining centrifugation and sedimentation at 1 g. *Scand J Clin Lab Invest Suppl*, 97, 77-89.

Brunmair, B., Staniek, K., Gras, F., Scharf, N., Althaym, A., Clara, R., Roden, M., Gnaiger, E., Nohl, H., Waldhausl, W. & Furnsinn, C. 2004. Thiazolidinediones, like metformin, inhibit respiratory complex I: a common mechanism contributing to their antidiabetic actions? *Diabetes*, 53, 1052-9.

Carvalho, C., Correia, S., Santos, M. S., Seica, R., Oliveira, C. R. & Moreira, P. I. 2008. Metformin promotes isolated rat liver mitochondria impairment. *Mol Cell Biochem*, 308, 75-83.

Chan, K., Truong, D., Shangari, N. & O'Brien, P. J. 2005. Drug-induced mitochondrial toxicity. *Expert Opin Drug Metab Toxicol*, 1, 655-69.

Davidson, M. B. & Peters, A. L. 1997. An overview of metformin in the treatment of type 2 diabetes mellitus. *Am J Med*, 102, 99-110.

Dykens, J. A., Jamieson, J., Marroquin, L., Nadanaciva, S., Billis, P. A. & Will, Y. 2008. Biguanide-induced mitochondrial dysfunction yields increased lactate production and cytotoxicity of aerobically-poised HepG2 cells and human hepatocytes in vitro. *Toxicol Appl Pharmacol*, 233, 203-10.

Dykens, J. A. & Will, Y. 2007. The significance of mitochondrial toxicity testing in drug development. *Drug Discov Today*, 12, 777-85.

El-Mir, M. Y. 2000. Dimethylbiguanide Inhibits Cell Respiration via an Indirect Effect Targeted on the Respiratory Chain Complex I. *J Biol Chem*, 275, 223-228.

Farina, J. A., Celotto, A. C., da Silva, M. F. & Evora, P. R. B. 2012. Guanylate cyclase inhibition by methylene blue as an option in the treatment of vasoplegia after a severe burn. A medical hypothesis. *Medical Science Monitor*, 18, Hy13-Hy17.

Fisher, J., Taori, G., Braitberg, G. & Graudins, A. 2014. Methylene blue used in the treatment of refractory shock resulting from drug poisoning. *Clin Toxicol (Phila)*, 52, 63-5.

Gnaiger, E. 2008. Polarographic oxygen sensors, the oxygraph and high-resolution respirometry to assess mitochondrial function. In: DYKENS, J. A., WILL, Y. (Ed.) *Mitochondrial Dysfunction in Drug-Induced Toxicity*. John Wiley & Sons, Inc.

Golan, D. E., Tashjian, A. H., Armstrong, E. J. & Armstrong, A. W. 2012. *Principles of pharmacology: the pathophysiologic basis of drug therapy*/David E. Golan, Philadelphia: Wolters Kluwer/Lippincott Williams & Wilkins, cop. 2012.

Graham, G. G., Punt, J., Arora, M., Day, R. O., Doogue, M. P., Duong, J. K., Furlong, T. J., Greenfield, J. R., Greenup, L. C., Kirkpatrick, C. M., Ray, J. E., Timmins, P. & Williams, K. M. 2011. Clinical pharmacokinetics of metformin. *Clin Pharmacokinet*, 50, 81-98.

Hinke, S. A., Martens, G. A., Cai, Y., Finsi, J., Heimberg, H., Pipeleers, D. & Van de Casteele, M. 2007. Methyl succinate antagonises biguanide-induced AMPK-activation and death of pancreatic beta-cells through restoration of mitochondrial electron transfer. *Br J Pharmacol*, 150, 1031-43.

Kane, D. A., Anderson, E. J., Price Iii, J. W., Woodlief, T. L., Lin, C.-T., Bikman, B. T., Cortright, R. N. & Neufer, P. D. 2010. Metformin selectively attenuates mitochondrial H2O2 emission without affecting respiratory capacity in skeletal muscle of obese rats. *Free Radical Bio Med*, 49, 1082-1087.

Kirpichnikov, D., McFarlane, S. I. & Sowers, J. R. 2002. Metformin: An Update. *Ann Intern Med*, 137, 25-33.

Kwong, S. C. & Brubacher, J. 1998. Phenformin and lactic acidosis: a case report and review. *J Emerg Med*, 16, 881-6.

Lalau, J. D. 2010. Lactic acidosis induced by metformin: incidence, management and prevention. *Drug Saf*, 33, 727-40.

Larsen, S., Rabøl, R., Hansen, C. N., Madsbad, S., Helge, J. W. & Dela, F. 2012. Metformin-treated patients with type 2 diabetes have normal mitochondrial complex I respiration. *Diabetologia*, 55, 443-449.

Livshits, Z., Nelson, L. S., Hernandez, S. H., Smith, S. W., Howland, M. A. & Hoffman, R. S. 2010. Severe Metformin Toxicity: Role of Methylene Blue and CVVHD as Therapeutic Adjuncts. *Clin Toxicol*, 48, 611-612.

Owen, M. R., Doran, E. & Halestrap, A. P. 2000. Evidence that metformin exerts its anti-diabetic effects through inhibition of complex 1 of the mitochondrial respiratory chain. *Biochem J*, 348 Pt 3, 607-14.

Pesta, D. & Gnaiger, E. 2012. High-resolution respirometry: OXPHOS protocols for human cells and permeabilized fibers from small biopsies of human muscle. *Methods Mol Biol*, 810, 25-58.

Plumb, B., Parker, A. & Wong, P. 2013. Feeling blue with metformin-associated lactic acidosis. *BMJ Case Rep*, 2013.

Protti, A., Fortunato, F., Monti, M., Vecchio, S., Gatti, S., Comi, G. P., De Giuseppe, R. & Gattinoni, L. 2012a. Metformin overdose, but not lactic acidosis per se, inhibits oxygen consumption in pigs. *Crit Care*, 16, R75.

Protti, A., Lecchi, A., Fortunato, F., Artoni, A., Greppi, N., Vecchio, S., Fagiolari, G., Moggio, M., Comi, G. P., Mistraletti, G., Lanticina, B., Faraldi, L. & Gattinoni, L. 2012b. Metformin overdose causes platelet mitochondrial dysfunction in humans. *Crit Care*, 16, R180.

Protti, A., Russo, R., Tagliabue, P., Vecchio, S., Singer, M., Rudiger, A., Foti, G., Rossi, A., Mistraletti, G. & Gattinoni, L. 2010. Oxygen consumption is depressed in patients with lactic acidosis due to biguanide intoxication. *Crit Care*, 14, R22.

Regenthal, R., Krueger, M., Koeppel, C. & Preiss, R. 1999. Drug Levels: Therapeutic and Toxic Serum/Plasma Concentrations of Common Drugs. *J Clin Monit Comput*, 15, 529-544.

Salpeter, S. R., Greyber, E., Pasternak, G. A. & Salpeter, E. E. 2010. Risk of fatal and nonfatal lactic acidosis with metformin use in type 2 diabetes mellitus. *Cochrane Data-base Syst Rev*, CD002967.

Scheen, A. J. 1996. Clinical pharmacokinetics of metformin. *Clin Pharmacokinet*, 30, 359-71.

Schulz, M. & Schmoldt, A. 2003. Therapeutic and toxic blood concentrations of more than 800 drugs and other xenobiotics. *Pharmazie,* 58, 447-74.

Sjövall, F., Ehinger, J. K., Marelsson, S. E., Morota, S., Frostner, E. A., Uchino, H., Lundgren, J., Arnbjornsson, E., Hansson, M. J., Fellman, V. & Elmer, E. 2013a. Mitochondrial respiration in human viable platelets—methodology and influence of gender, age and storage. *Mitochondrion,* 13, 7-14.

Sjövall, F., Morota, S., Persson, J., Hansson, M. J. & Elmer, E. 2013b. Patients with sepsis exhibit increased mitochondrial respiratory capacity in peripheral blood immune cells. *Crit Care,* 17, R152.

Sogame, Y., Kitamura, A., Yabuki, M. & Komuro, S. 2009. A comparison of uptake of metformin and phenformin mediated by hOCT1 in human hepatocytes. *Biopharm Drug Dispos,* 30, 476-84.

Tanner, R. K., Fuller, K. L. & Ross, M. L. 2010. Evaluation of three portable blood lactate analysers: Lactate Pro, Lactate Scout and Lactate Plus. *Eur J Appl Physiol,* 109, 551-9.

Wen, Y., Li, W. J., Poteet, E. C., Xie, L. K., Tan, C., Yan, L. J., Ju, X. H., Liu, R., Qian, H., Marvin, M. A., Goldberg, M. S., She, H., Mao, Z. X., Simpkins, J. W. & Yang, S. H. 2011. Alternative Mitochondrial Electron Transfer as a Novel Strategy for Neuroprotection. *J biol chem,* 286.

The invention claimed is:

1. A method for treating or preventing lactic acidosis, said method comprising administering an effective amount of a succinate prodrug to the subject,
wherein said succinate prodrug is a compound of Formula (I)

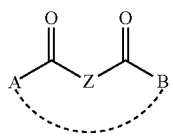
(I)

or a pharmaceutically acceptable salt thereof, wherein the dotted bond between A and B denotes an optional bond so as to form a ring closed structure, and wherein
Z is —$CH_2$—$CH_2$—,
A is —SR, and R is

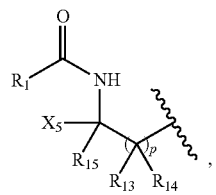

B is selected from the group consisting of —O—R', —SR''' and —OH; and R' is:

(IX)

R''' is:

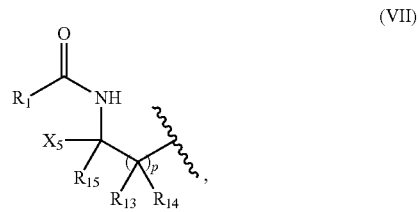
(VII)

$R_1$ and $R_3$ are independently different or identical and are selected from the group consisting of H, Me, Et, propyl, i-propyl, butyl, iso-butyl, and t-butyl,
X is selected from the group consisting of O, NH, and S,
p is an integer and is 1 or 2,
$X_5$ is selected from the group consisting of —H, —COOH, —C(=O)$XR_6$, and $CONR_1R_3$,
$R_6$ is selected from the group consisting of H, Me, Et, propyl, i-propyl, butyl, iso-butyl, t-butyl, acetyl, acyl, propionyl, and benzoyl,
$R_{13}$, $R_{14}$ and $R_{15}$ are independently different or identical and are selected from the group consisting of H, Me, Et, propyl, i-propyl, butyl, iso-butyl, t-butyl, —COOH, O-acyl, O-alkyl, N-acyl, N-alkyl, Xacyl, and $CH_2$Xalkyl,
$R_f$, $R_g$ and $R_h$ are independently different or identical and are selected from the group consisting of Xacyl, —$CH_2$Xalkyl, —$CH_2$X-acyl and $R_9$,
$R_9$ is selected from the group consisting of H, Me, Et and $O_2CCH_2CH_2COXR_8$, wherein $R_8$ is selected from the group consisting of H, alkyl, Me, Et, propyl, i-propyl, butyl, iso-butyl, t-butyl, acetyl, acyl, propionyl, and benzoyl,
alkyl is selected from the group consisting of Me, Et, propyl, i-propyl, butyl, iso-butyl, and t-butyl, and
acyl is selected from the group consisting of formyl, acetyl, propionyl, isopropionyl, butyryl, tert-butyryl, pentanoyl, and benzoyl.

2. The method of claim 1, wherein said subject is suffering from a disease that is treated with a drug substance, which potentially induces lactic acidosis,
the method comprises administering an effective amount of said succinate prodrug to the subject before, during or after treatment with said drug substance.

3. The method according to claim 2, wherein the drug substance is an anti-diabetic substance.

4. The method according to claim 3, wherein the anti-diabetic substance is metformin.

* * * * *